(12) United States Patent
Xi et al.

(10) Patent No.: US 9,326,975 B2
(45) Date of Patent: May 3, 2016

(54) SUBSTITUTED PYRAZOLONE COMPOUNDS AND METHODS OF USE

(71) Applicants: CALITOR SCIENCES, LLC, Newbury Park, CA (US); SUNSHINE LAKE PHARMA CO., LTD., Dongguan, Guangdong (CN)

(72) Inventors: Ning Xi, Newbury Park, CA (US); Yanjun Wu, Dongguan (CN); Min Liao, Dongguan (CN); Yanming Feng, Dongguan (CN)

(73) Assignees: SUNSHINE LAKE PHARMA CO., LTD, Dongguan, Guangdong (CN); CALITOR SCIENCES, LLC, Newbury Park, CA (US)

( * ) Notice: Subject to any disclaimer, the term of this patent is extended or adjusted under 35 U.S.C. 154(b) by 0 days.

(21) Appl. No.: 14/601,207

(22) Filed: Jan. 20, 2015

(65) Prior Publication Data

US 2015/0141463 A1    May 21, 2015

Related U.S. Application Data

(62) Division of application No. 13/945,924, filed on Jul. 19, 2013, now Pat. No. 8,975,282.

(60) Provisional application No. 61/676,944, filed on Jul. 28, 2012, provisional application No. 61/679,416, filed on Aug. 3, 2012.

(51) Int. Cl.
| | | |
|---|---|---|
| *C07D 401/14* | (2006.01) | |
| *A61K 31/444* | (2006.01) | |
| *A61K 31/4439* | (2006.01) | |
| *C07D 401/12* | (2006.01) | |
| *A61K 45/06* | (2006.01) | |

(52) U.S. Cl.
CPC ........... *A61K 31/4439* (2013.01); *A61K 31/444* (2013.01); *A61K 45/06* (2013.01); *C07D 401/12* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 7,459,562 B2 | 12/2008 | Borzilleri et al. | |
| 7,714,138 B2 | 5/2010 | Borzilleri et al. | |
| 7,851,489 B2 | 12/2010 | Borzilleri et al. | |
| 7,858,623 B2 | 12/2010 | Kim et al. | |
| 7,989,477 B2 | 8/2011 | Borzilleri et al. | |
| 8,088,794 B2 | 1/2012 | Kim et al. | |
| 8,124,768 B2 | 2/2012 | Borzilleri et al. | |
| 8,232,294 B2 | 7/2012 | Xi | |
| 8,258,118 B2 | 9/2012 | Borzilleri et al. | |
| 8,293,897 B2 | 10/2012 | Xi | |
| 8,426,585 B2 | 4/2013 | Xi | |
| 8,536,200 B2 | 9/2013 | Borzilleri et al. | |
| 8,558,000 B2 | 10/2013 | Livingston et al. | |
| 8,569,295 B2 | 10/2013 | Chen et al. | |
| 8,975,282 B2 * | 3/2015 | Xi ..................... | C07D 401/10 514/333 |
| 2008/0255155 A1 | 10/2008 | Raeppel et al. | |
| 2011/0053906 A1 | 3/2011 | Huck et al. | |
| 2011/0183983 A1 | 7/2011 | Kim et al. | |
| 2012/0070413 A1 | 3/2012 | Kim et al. | |
| 2012/0172382 A1 | 7/2012 | Flynn et al. | |
| 2012/0219522 A1 | 8/2012 | Xi | |
| 2012/0289509 A1 | 11/2012 | Kim et al. | |
| 2013/0123286 A1 | 5/2013 | Hu et al. | |
| 2013/0225569 A1 | 8/2013 | Burgdorf et al. | |
| 2013/0317066 A1 | 11/2013 | Flynn et al. | |

FOREIGN PATENT DOCUMENTS

| | | | |
|---|---|---|---|
| WO | WO 2006/116713 A1 * | 11/2006 | |
| WO | 2011095045 | 8/2011 | |
| WO | 2012167600 | 12/2012 | |
| WO | 2013022766 | 2/2013 | |
| WO | 2013180949 | 12/2013 | |

OTHER PUBLICATIONS

Wu et al., Toxicology, 236, pp. 1-6, 2007.*
Liu et al., Discovery of a Potent, Selective, and Orally Bioavailable c-Met Inhibitor: 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458), J. Med. Chem., 2008, vol. 51, Issue 13, p. 3688-3691.
Teffera et al., Chemical Reactivity of Methoxy 4-O-Aryl Quinolines: Identification of Glutathione Displacement Products in Vitro and in Vivo, Chem. Res. Toxicol., 2008, vol. 21, Issue 11, p. 2216-2222.
Zhang et al., Identification of a Novel Recepteur d'Origine Nantais/c-Met Small-Molecule Kinase Inhibitor with Antitumor Activity In vivo, Cancer Res., 2008, vol. 68, Issue 16, p. 6680-6687.
Liu et al., Structure-Based Design of Novel Class II c-Met Inhibitors: 2. SAR and Kinase Selectivity Profiles of the Pyrazolone Series, J. Med. Chem., 2012, vol. 55, Issue 5, p. 1868-1897.
Norman et al., Structure-Based Design of Novel Class II c-Met Inhibitors: 1. Identification of Pyrazolone-Based Derivatives, J. Med. Chem., 2012, vol. 55, Issue 5, p. 1858-1867.

* cited by examiner

*Primary Examiner* — Zinna Northington Davis
(74) *Attorney, Agent, or Firm* — Kam W. Law; Squire Patton Boggs (US) LLP

(57) ABSTRACT

The present invention provides novel substituted pyrazolone compounds, pharmaceutical acceptable salts and formulations thereof useful in modulating the protein tyrosine kinase activity, and in modulating cellular activities such as proliferation, differentiation, apoptosis, migration and invasion. The invention also provides pharmaceutically acceptable compositions comprising such compounds and methods of using the compositions in the treatment of hyperproliferative disorders in mammals, especially humans.

6 Claims, No Drawings

SUBSTITUTED PYRAZOLONE COMPOUNDS AND METHODS OF USE

CROSS-REFERENCE TO RELATED APPLICATIONS

This application is a divisional application of U.S. application Ser. No. 13/945,924 filed Jul. 19, 2013, now U.S. Pat. No. 8,975,282, which claims the benefits of U.S. Provisional Application No. 61/676,944, filed on Jul. 28, 2012, and U.S. Provisional Application No. 61/679,416, filed on Aug. 3, 2012, all of which are hereby incorporated by reference in their entirety.

FIELD OF THE INVENTION

This invention relates to novel substituted pyrazolone compounds, and salts thereof, which are useful in the treatment of hyperproliferative diseases, such as cancers, in mammals. In particular, the invention relates to compounds that inhibit the protein tyrosine kinase activity, resulting in the inhibition of inter- and/or intra-cellular signaling. This invention also relates to a method of using such compounds in the treatment of hyperproliferative diseases in mammals, especially humans, and to pharmaceutical compositions containing such compounds.

BACKGROUND OF THE INVENTION

Protein kinases represent a large family of proteins that play a central role in the regulation of a wide variety of cellular processes. Through regulating an array of signaling pathways, protein kinases control cell metabolism, cell cycle progression, cell proliferation and cell death, differentiation and survival. There are over 500 kinases in the human kinome, and over 150 of these have been shown or are proposed to be involved in the onset and/or progression of various human diseases including inflammatory diseases, cardiovascular diseases, metabolic diseases, neurodegenerative diseases and cancer.

A partial list of such kinases include abl, AATK, ALK, Akt, Axl, bmx, bcr-abl, Blk, Brk, Btk, csk, c-kit, c-Met, c-src, c-fms, CDK1, CDK2, CDK3, CDK4, CDK5, CDK6, CDK7, CDK8, CDK9, CDK10, cRaf1, CSF1R, CSK, DDR1, DDR2, EPHA, EPHB, EGFR, ErbB2, ErbB3, ErbB4, Erk, Fak, fes, FER, FGFR1, FGFR2, FGFR3, FGFR4, FGFR5, Fgr, flt-1, Fps, Frk, Fyn, GSG2, GSK, Hck, ILK, INSRR, IRAK4, ITK, IGF-1R, INS-R, Jak, KSR1, KDR, LMTK2, LMTK3, LTK, Lck, Lyn, MATK, MERTK, MLTK, MST1R, MUSK, NPR1, NTRK, MEK, MER, PLK4, PTK, p38, PDGFR, PIK, PKC, PYK2, RET, ROR1, ROR2, RYK, ros, Ron, SGK493, SRC, SRMS, STYK1, SYK, TEC, TEK, TEX14, TNK1, TNK2, TNNI3K, TXK, TYK2, Tyro-3, tie, tie2, TRK, Yes, and Zap70.

Protein tyrosine kinases are a subclass of protein kinase. They also may be classified as growth factor receptor (e.g., Axl, VEGFR, c-Met (HGFR), Ron, EGFR, PDGFR, and FGFR) or non-receptor (e.g., c-src and bcr-abl) kinases. Receptor tyrosine kinases are transmembrane proteins that possess an extracellular binding domain for growth factors, a transmembrane domain, and an intracellular portion that functions as a kinase to phosphorylate a specific tyrosine residue in proteins. Abnormal expression or activity of protein kinases has been directly implicated in the pathogenesis of myriad human cancers.

Angiogenesis, the formation of new capillaries from pre-existing blood vessels, is a necessary process for organ development during embryogenesis and is critical for the female reproductive cycle, inflammation, and wound healing in the adult. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example, so-called solid tumors and liquid tumors (such as leukemias). Solid tumors, in particular, are dependent on angiogenesis to grow beyond a certain critical size by inducing new capillaries sprouting from existing blood vessels to secure their nutrition, oxygen supply, and waste removal. In addition, angiogenesis also promotes metastasis of tumor cells to other sites.

The new vessel growth and maturation are highly complex and coordinated processes, requiring the stimulation by a number of growth factors, but vascular endothelial growth factor (VEGF) signaling often represents a critical rate-limiting step in physiological angiogenesis and pathological angiogenesis. VEGF binds to and activates the receptor tyrosine kinase, VEGFR. Three VEGFR isoforms have been identified in humans: VEGFR-1 (Flt-1), VEGFR-2 (KDR/Flk-1) and VEGFR-3 (Flt-4). VEGFR-2 mediates the majority of cellular responses to VEGF, in particular its mitogenic and angiogenic effects. VEGFR-1 is thought to modulate VEGFR-2 signaling or to act as a dummy/decoy receptor to sequester VEGF away from VEGFR-2. The expression of VEGFR-1 is also up-regulated by hypoxia, in a similar mechanism to VEGF, via HIF-1; its functions may vary depending on cell type and developmental stage. (Stuttfeld E, Ballmer-Hofer K (September 2009), "Structure and function of VEGF receptors," *IUBMB Life* 61 (9): 915-22.)

Since VEGFR-2 is the major mediator of vascular endothelial cell (EC) mitogenesis and survival, as well as angiogenesis and microvascular permeability, it is expected that direct inhibition of the kinase activity of VEGFR-2 will result in the reduction of angiogenesis and the suppression of tumor growth. Furthermore, inhibition of VEGFR-2 targeting the genetically more stable host endothelial cells, instead of labile tumor tissues, may decrease the chance of resistance development. Several agents targeting VEGFR signaling, administered either as single agents or in combination with chemotherapy, have been shown to benefit patients with advanced-stage malignancies. ("VEGF-targeted therapy: mechanisms of anti-tumor activity," *Nature Reviews Cancer*, 2008, 8, 579; "Molecular basis for sunitinib efficacy and future clinical development," *Nature Reviews Drug Discovery*, 2007, 6, 734; and "Angiogenesis: an organizing principle for drug discovery?" *Nature Reviews Drug Discovery*, 2007, 6, 273).

c-Met, also referred to as hepatocyte growth factor receptor (HGFR), is expressed predominantly in epithelial cells but has also been identified in endothelial cells, myoblasts, hematopoietic cells and motor neurons. The natural ligand for c-Met is hepatocyte growth factor (HGF), also known as scatter factor (SF). In both embryos and adults, activated c-Met promotes a morphogenetic program, known as invasive growth, which induces cell spreading, the disruption of inter-cellular contacts, and the migration of cells towards their surroundings. ("From Tpr-Met to Met, tumorigenesis and tubes," Oncogene, 2007, 26, 1276; and "Met Receptor Tyrosine Kinase as a Therapeutic Anticancer Target," Cancer Letter, 2009, 280, 1-14).

A wide variety of human malignancies exhibit sustained c-Met stimulation, overexpression, or mutation, including carcinomas of the breast, liver, lung, ovary, kidney, thyroid, colon, renal, glioblastomas, and prostate, etc. c-Met is also implicated in atherosclerosis and lung fibrosis. Invasive growth of certain cancer cells is drastically enhanced by tumor-stromal interactions involving the HGF/c-Met pathway. Thus, extensive evidence that c-Met signaling is involved in the progression and spread of several cancers and an enhanced understanding of its role in disease have generated considerable interest in c-Met as major targets in cancer drug development. ("Molecular cancer therapy: can our expectation be MET," Euro. J. Cancer, 2008, 44, 641-651; and "Targeting the c-Met Signaling Pathway in Cancer," Clin. Cancer Res., 2006, 12, 3657). Agents targeting c-Met signaling pathway are now under clinical investigation. ("Novel Therapeutic Inhibitors of the c-Met Signaling Pathway in Cancer," Clinical Cancer Research, 2009, 15, 2207), and "Drug development of MET inhibitors: targeting oncogene addiction and expedience," Nature Review Drug Discovery, 2008, 7, 504).

Axl belongs to the subfamily of receptor tyrosine kinases (RTKs) that also includes Tyro3 and Mer (TAM). The TAM receptors are characterized by a combination of two immunoglobin-like domains and dual fibronectin type III repeats in the extracellular region and a cytoplasmic kinase domain. The ligands for TAM receptors are Gas6 (growth arrest-specific 6) and protein S, two vitamin K-dependent proteins that exhibit 43% amino-acid sequence identity and share similar domain structures ("The anticoagulation factor protein S and its relative, Gas6, are ligands for the Tyro 3/Axl family of receptor tyrosine kinases," Cell, 1995, 80, 661-670; and "Axl receptor tyrosine kinase stimulated by the vitamin K-dependent protein encoded by growth-arrest-specific gene 6," Nature, 1995, 373, 623-626).

Adequate evidence supports the role of the Gas6/Axl system in driving cell growth and survival in normal and cancer cells ("TAM receptor tyrosine kinases: biologic functions, signaling, and potential therapeutic targeting in human cancer," Adv Cancer Res, 2008, 100, 35-83). Axl overexpression and signaling has been implicated in several human malignancies, such as colon, breast, glioma, thyroid, gastric, melanoma, lung cancer, and in renal cell carcinoma (RCC). A more detailed role of Axl biology has been proven in glioma, where loss of Axl signaling diminished glioma tumor growth, and in breast cancer, where Axl drive cell migration, tube formation, neovascularization, and tumor growth. Axl has been shown to play multiple roles in tumorigenesis and that therapeutic antibodies against Axl may block Axl functions not only in malignant tumor cells but also in the tumor stroma. The additive effect of Axl inhibition with anti-VEGF suggests that blocking Axl function could be an effective approach for enhancing antiangiogenic therapy. ("Axl as a potential therapeutic target in cancer: role of Axl in tumor growth, metastasis and angiogenesis," Oncogene, 2009, 28, 3442-3455; and "TAM Receptor Tyrosine Kinases: Biologic Functions, Signaling, and Potential Therapeutic Targeting in Human Cancer," Adv Cancer Res., 2008, 100, 35-83).

RON (MST1R, recepteur d'origine nantais), the other member of the MET family, is a receptor tyrosine kinase for the ligand macrophage-stimulating protein (MSP, also known as MST1, and hepatocyte growth factor-like (HGFL)), which is associated with in vitro and in vivo cell dissociation, motility and matrix invasion—all of which are surrogate markers of an aggressive cancer phenotype with metastatic potential. RON mediates oncogenic phenotypes in lung, thyroid, pancreas, prostate, colon and breast cancer cells and predicts a poor prognosis in human breast cancer. Co-expression of RON with MET and the induction of RON expression by HGF-MET signaling have both been described in hepatocellular carcinoma. Furthermore, co-expression of MET and RON portends a worse prognosis in ovary, breast and bladder cancers. Given RON and MET signaling redundancy, it is possible that resistance to MET inhibition is mediated by RON signaling ("RON (MST1R) is a novel prognostic marker and therapeutic target for gastroesophageal adenocarcinoma." Cancer Biol Ther. 2011 Jul. 1; 12(1): 9-46.).

The roles of MSP-RON signaling axis in cancer pathogenesis has also been extensively studied in various model systems. Both in vitro and in vivo evidence has revealed that MSP-RON signalling is important for the invasive growth of different types of cancers. Aberrant RON activation, which is induced by overexpression of protein and the generation of oncogenic isoforms and is indicated by the persistent activation of multi-intracellular signaling cascades, occurs in various types of cancers. RON signaling is also necessary for cancer cell growth and survival. These features render RON as a drug target for cancer therapy ("MSP-RON signalling in cancer: pathogenesis and therapeutic potential." Nature Reviews Cancer, 2013, 13, 466-481).

It is widely known that cancer cells employ multiple mechanisms to evade tightly regulated cellular processes such as proliferation, apoptosis, and senescence. Thus, most tumors can escape from the inhibition of any single kinase. System-wide analyses of tumors identified receptor tyrosine kinase (RTK) coactivation as an important mechanism by which cancer cells achieve chemoresistance. One of the strategies to overcome RTK coactivation may involve therapeutically targeting multiple RTKs simultaneously in order to shut down oncogenic RTK signaling and overcome compensatory mechanisms. ("Receptor Tyrosine Kinas Coactivation Networks in Cancer," Cancer Research, 2010, 70, 3857). Anti-tumor approaches in targeting VEGFR, c-Met, Ron and/or Axl signaling may circumvent the ability of tumor cells to overcome VEGFR, c-Met (HGFR), Ron and/or Axl inhibition alone and thus may represent improved cancer therapeutics.

SUMMARY OF THE INVENTION

Provided herein are new compounds and methods for treating cell proliferative diseases. The compounds disclosed herein are inhibitors of protein tyrosine kinases. Preferably, the compounds disclosed herein are multiple function inhibitors, capable of inhibiting, for example, VEGFR, c-Met (HGFR), Ron and/or Axl. Accordingly, provided herein are new inhibitors of protein tyrosine kinase receptor signaling, such as VEGF receptor signaling, HGF receptor signaling, Ron signaling and/or Axl signaling.

Specifically, it has been found that compounds disclosed herein, and pharmaceutically acceptable compositions thereof, are effective as inhibitors of receptor tyrosine kinases such as VEGFR, c-Met, Ron and/or Axl.

In one aspect, provided herein is a compound having Formula (I):

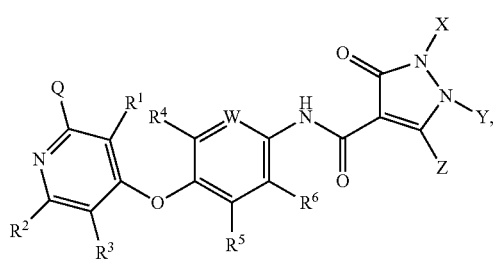

or a stereoisomer, a geometric isomer, a tautomer, an N-oxide, a solvate, a hydrate, a metabolite, a pharmaceutically acceptable salt or a prodrug thereof, wherein each of Q, $R^1$, $R^2$, $R^3$, $R^4$, $R^5$, $R^6$, W, X, Y and Z is as defined herein.

In some embodiments, the compound disclosed herein has formula (II):

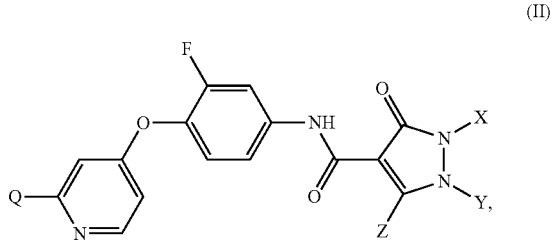

(II)

wherein each of Q, X, Y and Z is as defined herein.

In some embodiments, Q is D, —N($R^c$)C(=O)N$R^aR^b$, —N($R^c$)C(=O)$R^d$, —C(=O)N$R^aR^b$, —N($R^c$)S(=O) N$R^aR^b$, —N($R^c$)S(=O)$R^a$, —N($R^c$)S(=O)$_2$N$R^aR^b$ or —N($R^c$)S(=O)$_2R^a$;

W is $CR^7$ or N;

each of X, Y and Z is independently H, D, $(C_1-C_6)$alkyl, $(C_3-C_8)$cycloalkyl, —$(C_1-C_4)$alkylene-$(C_3-C_8)$cycloalkyl, $(C_3-C_7)$heterocyclyl, —$(C_1-C_4)$alkylene-$(C_3-C_7)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$alkyl, $(C_3-C_8)$cycloalkyl, —$(C_1-C_4)$alkylene-$(C_3-C_8)$cycloalkyl, $(C_3-C_7)$heterocyclyl, —$(C_1-C_4)$alkylene-$(C_3-C_7)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3, 4 or 5 substituents independently selected from D, F, Cl, Br, CN, $(C_2-C_6)$alkenyl, $(C_2-C_6)$alkynyl, O$R^a$, N$R^aR^b$, —$(C_1-C_4)$alkylene-O$R^a$ and —$(C_1-C_4)$alkylene-N$R^aR^b$;

each of $R^1$, $R^2$, $R^3$, $R^4$, $R^5$, $R^6$ and $R^7$ is independently H, D, F, Cl, Br, CN, $N_3$, O$R^a$, $(C_1-C_6)$alkyl, $(C_1-C_6)$haloalkyl, $(C_2-C_6)$alkenyl or $(C_2-C_6)$alkynyl;

each of $R^a$, $R^b$ and $R^c$ is independently H, $(C_1-C_6)$aliphatic, $(C_1-C_6)$haloalkyl, $(C_3-C_6)$cycloalkyl, —$(C_1-C_4)$alkylene-$(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$aliphatic, $(C_1-C_6)$haloalkyl, $(C_3-C_6)$cycloalkyl, —$(C_1-C_4)$alkylene-$(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3 or 4 substituents independently selected from D, F, Cl, CN, $N_3$, OH, $NH_2$, $(C_1-C_6)$haloalkyl, $(C_1-C_6)$alkoxy and $(C_1-C_6)$alkylamino; and $R^d$ is D, $(C_3-C_8)$cycloalkyl, —$(C_1-C_4)$alkylene-$(C_6-C_{10})$aryl, 5-10 membered heteroaryl comprising 1, 2, 3 or 4 heteroatoms independently selected from O, S and N or —$(C_1-C_4)$alkylene-(5-10 membered heteroaryl), wherein each of the $(C_3-C_8)$cycloalkyl, —$(C_1-C_4)$alkylene-$(C_6-C_{10})$aryl, 5-10 membered heteroaryl and —$(C_1-C_4)$alkylene-(5-10 membered heteroaryl) is unsubstituted or optionally substituted with 1, 2, 3 or 4 substituents independently selected from D, F, Cl, Br, CN, O$R^a$, N$R^aR^b$, $(C_1-C_6)$alkyl, $(C_2-C_6)$alkenyl, $(C_2-C_6)$alkynyl, —$(C_1-C_4)$alkylene-O$R^a$ and —$(C_1-C_4)$alkylene-N$R^aR^b$.

In other embodiments, each of $R^a$, $R^b$ and $R^c$ is independently H, $(C_1-C_6)$aliphatic, $(C_1-C_6)$haloalkyl, $(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$aliphatic, $(C_1-C_6)$haloalkyl, $(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl, —$(C_1-C_4)$ alkylene-$(C_6-C_{10})$aryl and —$(C_1-C_4)$alkylene-(5-10 membered heteroaryl) is unsubstituted or optionally substituted with 1, 2, 3 or 4 substituents independently selected from D, F, Cl, CN, $N_3$, OH, $NH_2$, $(C_1-C_6)$haloalkyl, $(C_1-C_6)$alkoxy and $(C_1-C_6)$alkylamino; and $R^d$ is D, $(C_3-C_8)$cycloalkyl, —$(C_1-C_4)$alkylene-$(C_6-C_{10})$aryl, 5-10 membered heteroaryl comprising 1, 2, 3 or 4 heteroatoms independently selected from O, S and N or —$(C_1-C_4)$alkylene-(5-10 membered heteroaryl), wherein each of the $(C_3-C_8)$cycloalkyl, —$(C_1-C_4)$alkylene-$(C_6-C_{10})$aryl, 5-10 membered heteroaryl and —$(C_1-C_4)$alkylene-(5-10 membered heteroaryl) is unsubstituted or optionally substituted with 1, 2, 3 or 4 substituents independently selected from D, F, Cl, Br, CN, O$R^a$, N$R^aR^b$, $(C_2-C_6)$alkenyl, $(C_2-C_6)$alkynyl, —$(C_1-C_4)$alkylene-O$R^a$ and —$(C_1-C_4)$alkylene-N$R^aR^b$.

In other embodiments, Q is —N($R^c$)C(=O)N$R^aR^b$, —N($R^c$)C(=O)$R^d$ or —C(=O)N$R^aR^b$.

In other embodiments, each of X, Y and Z is independently $(C_1-C_4)$alkyl, $(C_3-C_6)$cycloalkyl, —$(C_1-C_2)$alkylene-$(C_3-C_6)$cycloalkyl, $(C_3-C_6)$heterocyclyl, —$(C_1-C_2)$alkylene-$(C_3-C_6)$heterocyclyl, phenyl, 5-10 membered heteroaryl comprising 1, 2, 3 or 4 heteroatoms independently selected from O, S and N, —$(C_1-C_2)$alkylene-phenyl or —$(C_1-C_2)$alkylene-(5-10 membered heteroaryl), wherein each of the $(C_1-C_4)$alkyl, $(C_3-C_6)$cycloalkyl, —$(C_1-C_2)$alkylene-$(C_3-C_6)$cycloalkyl, $(C_3-C_6)$heterocyclyl, —$(C_1-C_2)$alkylene-$(C_3-C_6)$heterocyclyl, phenyl, 5-10 membered heteroaryl, —$(C_1-C_2)$alkylene-phenyl and —$(C_1-C_2)$alkylene-(5-10 membered heteroaryl) is unsubstituted or optionally substituted with 1, 2, 3 or 4 substituents independently selected from D, F, Cl, CN, $(C_2-C_4)$alkenyl, $(C_2-C_4)$alkynyl, O$R^a$, N$R^aR^b$, —$(C_1-C_2)$alkylene-O$R^a$ and —$(C_1-C_2)$alkylene-N$R^aR^b$.

In other embodiments, each of $R^1$, $R^2$, $R^3$, $R^4$, $R^5$, $R^6$ and $R^7$ is independently H, D, F or Cl.

In others embodiment, each of $R^a$, $R^b$ and $R^c$ is independently H, $(C_1-C_4)$alkyl, $(C_1-C_4)$haloalkyl, $(C_3-C_6)$cycloalkyl, —$(C_1-C_2)$alkylene-$(C_3-C_6)$cycloalkyl, $(C_3-C_6)$heterocyclyl or —$(C_1-C_2)$alkylene-$(C_3-C_6)$heterocyclyl, wherein each of the $(C_1-C_4)$alkyl, $(C_1-C_4)$haloalkyl, $(C_3-C_6)$cycloalkyl, —$(C_1-C_2)$alkylene-$(C_3-C_6)$cycloalkyl, $(C_3-C_6)$heterocyclyl and —$(C_1-C_2)$alkylene-$(C_3-C_6)$heterocyclyl is unsubstituted or optionally substituted with 1, 2, 3 or 4 substituents independently selected from D, F, Cl, CN, $N_3$, OH, $NH_2$, $(C_1-C_3)$haloalkyl, $(C_1-C_3)$alkoxy and $(C_1-C_3)$alkylamino.

In other embodiments, $R^d$ is $(C_3-C_6)$cycloalkyl, wherein the $(C_3-C_6)$cycloalkyl is unsubstituted or optionally substituted with 1, 2, 3 or 4 substituents independently selected from D, F, CN, O$R^a$, N$R^aR^b$, $(C_1-C_3)$alkyl, $(C_2-C_4)$alkenyl, $(C_2-C_4)$alkynyl, —$(C_1-C_2)$alkylene-O$R^a$ and —$(C_1-C_2)$alkylene-N$R^aR^b$.

In other embodiments, each of X, Y and Z is independently H, D, $CH_3$, methyl group substituted with 1, 2 or 3 deuterium atoms, ethyl, propyl, isopropyl, phenyl or phenyl group substituted with 1, 2, 3, 4 or 5 substituents independently selected from D, F and Cl.

In other embodiments, Q is:

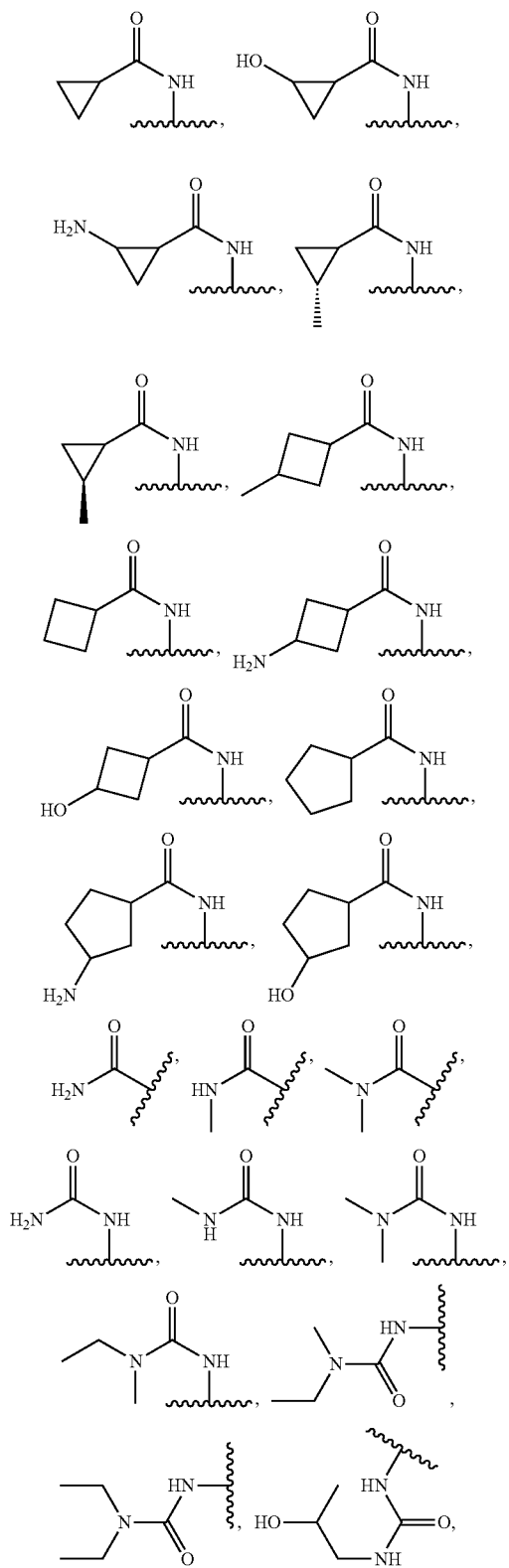

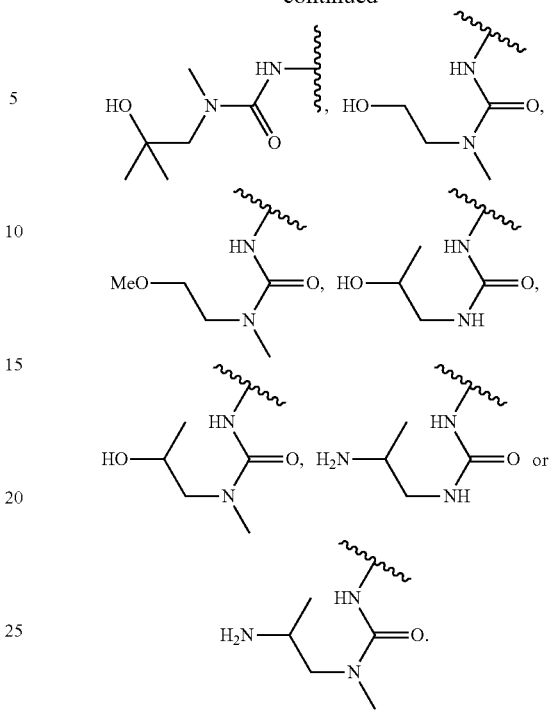

In another aspect, provided herein is a pharmaceutical composition comprising the compound disclosed herein that is an inhibitor of receptor tyrosine kinase, or a stereoisomer, geometric isomer, tautomer, solvate, metabolite, pharmaceutically acceptable salt thereof, and a pharmaceutically acceptable carrier, excipient, diluent, adjuvant, vehicle or a combination thereof. In some embodiments, the pharmaceutical composition comprise the compound disclosed herein that is an inhibitor of VEGF receptor signaling, HGF receptor signaling, Ron signaling and/or Axl signaling. or a stereoisomer, geometric isomer, tautomer, solvate, metabolite, pharmaceutically acceptable salt thereof, and a pharmaceutically acceptable carrier, excipient, diluent, adjuvant, vehicle or a combination thereof.

In other embodiments, the pharmaceutical composition disclosed herein further comprises a therapeutic agent.

In other embodiments, the therapeutic agent is a chemotherapeutic agent, an anti-proliferative agent, an agent for treating atherosclerosis, an agent for treating lung fibrosis, or combinations thereof.

In other embodiments, the therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, ramucirumab, rituximab, tositumomab, trastuzumab, or a combination thereof.

In another aspect, provided herein is the compound disclosed herein or the pharmaceutical composition disclosed herein for use in preventing, managing, treating or lessening the severity of a proliferative disorder in a patient.

In another aspect, provided herein is a method of preventing, managing, treating or lessening the severity of a proliferative disorder in a patient by administering to the patient the compound disclosed herein.

In another aspect, provided herein is a method of preventing, managing, treating or lessening the severity of a proliferative disorder in a patient by administering to the patient the pharmaceutical composition disclosed herein.

In some embodiments, the proliferative disorder is metastatic cancer. In other embodiments, the proliferative disorder is colon cancer, gastric adenocarcinoma, bladder cancer, breast cancer, kidney cancer, liver cancer, lung cancer, skin cancer, thyroid cancer, a cancer of the head and neck, prostate cancer, pancreatic cancer, a cancer of the CNS, glioblastoma or a myeloproliferative disorder, In further embodiments, the proliferative disorder is atherosclerosis or lung fibrosis.

In another aspect, provided herein is the compound disclosed herein or the pharmaceutical composition disclosed herein for use in inhibiting or modulating the activity of a protein kinase in a biological sample comprising contacting a biological sample with the compound disclosed herein or the pharmaceutical composition disclosed herein.

In another aspect, provided herein is a method of inhibiting or modulating the activity of a protein kinase in a biological sample comprising contacting a biological sample with the compound disclosed herein.

In another aspect, provided herein is a method of inhibiting or modulating the activity of a protein kinase in a biological sample comprising contacting a biological sample with the pharmaceutical composition disclosed herein.

In some embodiments, the protein kinase is a receptor tyrosine kinase. In other embodiments, the receptor tyrosine kinase is VEGFR, c-Met, Ron, Axl or a combination thereof.

In some embodiments, inhibition of the activity of a receptor protein kinase, preferably VEGF receptor signaling, HGF receptor signaling, Ron signaling or Axl receptor signaling, can be in a cell or a multicellular organism. If in a multicellular organism, the method according to this aspect of the invention comprises administering to the organism the compound disclosed herein, or the pharmaceutical composition disclosed herein. In some embodiments, the organism is a mammal. In other embodiments is a human. In yet another embodiment, the method further comprises contacting the kinase with a therapeutic agent.

In another aspect, provided herein are methods of inhibiting proliferative activity of a cell, the method comprising contacting the cell with an effective proliferative inhibiting amount of a compound according to the present invention or a composition thereof. In some embodiments, the method further comprises contacting the cell with a therapeutic agent.

In another aspect, provided herein are methods of treating a cell proliferative disease in a patient, the method comprising administering to the patient in need of such treatment an effective therapeutic amount of a compound according to the present invention or a composition thereof. In some embodiments, the method further comprises administering a therapeutic agent.

In another aspect, provided herein are methods of inhibiting tumor growth in a patient, the method comprising administering to the patient in need thereof an effective therapeutic amount of a compound according to the present invention or a composition thereof. In some embodiments, the method further comprises administering a therapeutic agent.

In another aspect, provided herein are methods of preparing, methods of separating, and methods of purifying compounds of Formula (I) or (II).

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry," by Michael B. Smith and Jerry March, John Wiley & Sons, New York: 2007, the entire contents of which are hereby incorporated by reference.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-3 carbon atoms. Suitable aliphatic groups include, but are not limited to, linear or branched, substituted or unsubstituted alkyl, alkenyl, or alkynyl groups. For example, ($C_1$-$C_6$)aliphatic groups include unbranched or branched, unsubstituted or suitably substituted ($C_1$-$C_6$)alkyl, ($C_2$-$C_6$)alkenyl, or ($C_2$-$C_6$)alkynyl groups. The aliphatic radicals are optionally substituted independently with one or more substituents described herein.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, alkyl groups contain 1-20 carbon atoms. In some embodiments, alkyl groups contain 1-10 carbon atoms. In other embodiments, alkyl groups contain 1-8 carbon atoms. In other embodiments, alkyl groups contain 1-6 carbon atoms. In still other embodiments, alkyl groups contain 1-4 carbon atoms, and in yet other embodiments, alkyl groups contain 1-3 carbon atoms.

Some non-limiting examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The terms "alkyl" and the prefix "alk-" are inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, alkylene groups contain 1-10 carbon atoms. In some embodiments, alkylene groups contain 1-6 carbon atoms. In other embodiments, alkylene groups contain 1-4 carbon atoms. In still other embodiments, alkylene groups contain 1-2 carbon atoms, and is exemplified by methylene (—$CH_2$—), ethylene (—$CH_2CH_2$—), isopropylene (—$CH(CH_3)CH_2$—), and the like.

The term "alkenyl" refers to linear or branched-chain monovalent hydrocarbon radical of 2 to 12 carbon atoms with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Preferably, alkenyl group contains 2 to 8 carbon atoms, and more preferably, 2 to 6 carbon atoms. Examples include, but are not limited to, ethylenyl or vinyl (—$CH=CH_2$), allyl (—$CH_2CH=CH_2$), and the like.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. Preferably, alkynyl group contains 2 to 8 carbon atoms, and more preferably 2 to 6 carbon atoms. Examples include, but are not limited to, ethynyl (—$C\equiv CH$), propynyl (propargyl, —$CH_2C\equiv CH$), —$C\equiv C$—$CH_3$, and the like.

The term "alkoxy" refers to an alkyl group, as previously defined, attached to the principal carbon atom through an oxygen atom. Unless otherwise specified, alkoxy groups contain 1-20 carbon atoms. In some embodiments, alkoxy groups contain 1-10 carbon atoms. In other embodiments, alkoxy groups contain 1-8 carbon atoms. In still other embodiments, alkoxy groups contain 1-6 carbon atoms. In yet other embodiments, alkoxy groups contain 1-4 carbon atoms. In further embodiments, alkoxy groups contain 1-3 carbon atoms. The alkoxy radicals are optionally substituted independently with one or more substituents described herein.

Some non-limiting examples of alkoxy groups include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The terms "haloalkyl", "haloalkenyl" or "haloalkoxy" refers to alkyl, alkenyl, or alkoxy, as the case may be, substituted with one or more halogen atoms.

The term "carbocycle", "carbocyclyl", "carbocyclic ring" or "cycloaliphatic" refers to a monovalent or multivalent non-aromatic, saturated or partially unsaturated ring having 3 to 12 carbon atoms as a monocyclic, bicyclic, or tricyclic ring system. Suitable cycloaliphatic groups include, but are not limited to, cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like.

The term "cycloalkyl" refers to a monovalent or multivalent saturated ring having 3 to 12 carbon atoms as a monocyclic, bicyclic, or tricyclic ring system. A bicyclic ring system includes a spiro bicyclyl or a fused bicyclyl. In some embodiments, a cycloalkyl contains 3 to 10 carbon atoms. In still other embodiments, a cycloalkyl contains 3 to 8 carbon atoms, and in yet other embodiments, a cycloalkyl contains 3 to 6 carbon atoms. The cycloalkyl radicals are optionally substituted independently with one or more substituents described herein.

The term "heterocycle", "heterocyclyl", or "heterocyclic" as used interchangeably herein refers to a monocyclic, bicyclic, or tricyclic ring system in which one or more ring members are independently selected from heteroatoms and that is completely saturated or that contains one or more units of unsaturation, but which is not aromatic, that has a single point of attachment to the rest of the molecule. A bicyclic ring system includes a spiro bicyclyl or a fused bicyclyl, and one of the rings can be either a monocarbocycle or a monoheterocycle. One or more ring atoms are optionally substituted independently with one or more substituents described herein. In some embodiments, the "heterocycle", "heterocyclyl", or "heterocyclic" group is a monocycle having 3 to 7 ring members (2 to 6 carbon atoms and 1 to 3 heteroatoms selected from N, O, P, and S, wherein the S or P is optionally substituted with one or more oxo to provide the group SO or $SO_2$, PO or $PO_2$). In other embodiments, the "heterocycle", "heterocyclyl", or "heterocyclic" group is a monocycle having 3 to 6 ring members (2 to 5 carbon atoms and 1 to 3 heteroatoms selected from N, O, P, and S, wherein the S or P is optionally substituted with one or more oxo to provide the group SO or $SO_2$, PO or $PO_2$), or a bicycle having 7 to 10 ring members (4 to 9 carbon atoms and 1 to 3 heteroatoms selected from N, O, P, and S, wherein the S or P is optionally substituted with one or more oxo to provide the group SO or $SO_2$, PO or $PO_2$).

The heterocyclyl may be a carbon radical or heteroatom radical. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homo-piperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 1,2,3,4-tetrahydroiso-quinolinyl. Examples of a heterocyclic group wherein 2 ring carbon atoms are substituted with oxo (=O) moieties are pyrimidindionyl and 1,1-dioxo-thiomorpholinyl.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to F, Cl, Br, or I.

The term "H" refers to a single hydrogen atom. This radical may be attached, for example, to an oxygen atom to form a hydroxyl radical.

The term "D" or "$^2$H" refers to a single deuterium atom. One of this radical may be attached, for example, to a methyl group to form a mono-deuterated methyl group (—$CDH_2$), two of deuterium atoms may attached to a methyl group to form a di-deuterated methyl (—$CD_2H$), and three of deuterium atoms may attached to a methyl group to form a tri-deuterated methyl group (—$CD_3$).

The term "$N_3$" refers to an azide moiety. This radical may be attached, for example, to a methyl group to form azidomethane (methyl azide, $MeN_3$); or attached to a phenyl group to form phenyl azide ($PhN_3$).

The term "aryl" used alone or as part of a larger moiety as in "aralkyl", "aralkoxy" or "aryloxyalkyl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene. The aryl radicals are optionally substituted independently with one or more substituents described herein.

The term "heteroaryl" used alone or as part of a larger moiety as in "heteroaralkyl" or "heteroarylalkoxy" refers to monocyclic, bicyclic, and tricyclic ring systems having a total of 5 to 14 ring members, preferably, 5 to 12 ring members, and more preferably 5 to 10 ring members, wherein at least one ring in the system is aromatic, at least one ring in the system contains one or more heteroatoms, wherein each ring in the system contains 5 to 7 ring members and that has a single point of attachment to the rest of the molecule. The term "heteroaryl" may be used interchangeably with the term "heteroaryl ring" or the term "heteroaromatic". The heteroaryl radicals are optionally substituted independently with one or more substituents described herein.

Some non-limiting examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The terms "carboxy" or "carboxyl", whether used alone or with other terms, such as "carboxyalkyl", refers to —$CO_2H$. The term "carbonyl", whether used alone or with other terms, such as "aminocarbonyl", denotes —(C=O)—.

The term "alkylamino" embraces "N-alkylamino" and "N,N-dialkylamino" where amino groups are independently substituted with one alkyl radical or with two alkyl radicals, respectively. Some non-limiting examples of alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N, N-diethylamino and the like.

The term "arylamino" refers to amino groups, which have been substituted with one or two aryl radicals, such as N-phenylamino. The arylamino radicals may be further substituted on the aryl ring portion of the radical.

The term "aminoalkyl" refers to linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl.

The term "unsaturated" refers to a moiety having one or more units of unsaturation.

The term "comprising" is meant to be open ended, including the indicated component but not excluding other elements.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The term "prodrug" refers to a compound that is transformed in vivo into a compound of formula (I) or (II). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, each of which is incorporated herein by reference.

A "metabolite" refers to a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A "pharmaceutically acceptable salt" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 66: 1-19, 1977, which is incorporated herein by reference. Examples of pharmaceutically acceptable, nontoxic salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxy-methy-1, 2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

Description of Compounds of the Invention

The present invention provides substituted pyrazolone compounds, salts, and pharmaceutical formulations thereof, which are potentially useful in the treatment of diseases, conditions and disorders modulated by receptor tyrosine kinases, especially VEGFR, c-Met, Ron and/or Axl receptor. More specifically, the present invention provides compounds of Formula (I):

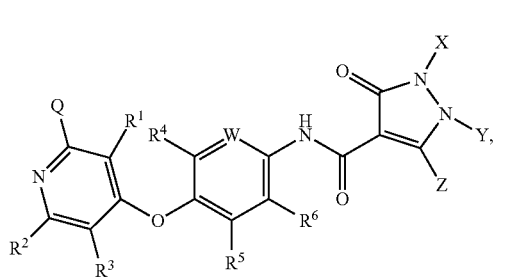

or a stereoisomer, a geometric isomer, a tautomer, an N-oxide, a solvate, a hydrate, a metabolite, a pharmaceutically acceptable salt or a prodrug thereof, wherein each of Q, $R^1$, $R^2$, $R^3$, $R^4$, $R^5$, $R^6$, W, X, Y and Z is as defined herein.

In certain embodiments, Q in formula (I) is D, —$N(R^c)C(=O)NR^aR^b$, —$N(R^c)C(=O)R^d$, —$C(=O)NR^aR^b$, —$N(R^c)S(=O)NR^aR^b$, —$N(R^c)S(=O)R^a$, —$N(R^c)S(=O)_2NR^aR^b$ or —$N(R^c)S(=O)_2R^a$;
W in formula (I) is $CR^7$ or N;
each of X, Y and Z in formula (I) is independently H, D, $(C_1-C_6)$alkyl, $(C_3-C_8)$cycloalkyl, —$(C_1-C_4)$alkylene-$(C_3-C_8)$cycloalkyl, $(C_3-C_7)$heterocyclyl, —$(C_1-C_4)$alkylene-$(C_3-C_7)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$alkyl, $(C_3-C_8)$cycloalkyl, —$(C_1-C_4)$alkylene-$(C_3-C_8)$cycloalkyl, $(C_3-C_7)$heterocyclyl, —$(C_1-C_4)$alkylene-$(C_3-C_7)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3, 4 or 5 substituents independently selected from D, F, Cl, Br, CN, $(C_2-C_6)$alkenyl, $(C_2-C_6)$alkynyl, $OR^a$, $NR^aR^b$, —$(C_1-C_4)$alkylene-$OR^a$ and —$(C_1-C_4)$alkylene-$NR^aR^b$;
each of $R^1$, $R^2$, $R^3$, $R^4$, $R^5$, $R^6$ and $R^7$ in formula (I) is independently H, D, F, Cl, Br, CN, $N_3$, $OR^a$, $(C_1-C_6)$alkyl, $(C_1-C_6)$haloalkyl, $(C_2-C_6)$alkenyl or $(C_2-C_6)$alkynyl;

each of $R^a$, $R^b$ and $R^c$ in formula (I) is independently H, $(C_1-C_6)$aliphatic, $(C_1-C_6)$haloalkyl, $(C_3-C_6)$cycloalkyl, —$(C_1-C_4)$alkylene-$(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$aliphatic, $(C_1-C_6)$haloalkyl, $(C_3-C_6)$cycloalkyl, —$(C_1-C_4)$alkylene-$(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3 or 4 substituents independently selected from D, F, Cl, CN, $N_3$, OH, $NH_2$, $(C_1-C_6)$haloalkyl, $(C_1-C_6)$alkoxy and $(C_1-C_6)$alkylamino; and
$R^d$ in formula (I) is D, $(C_3-C_8)$cycloalkyl, —$(C_1-C_4)$alkylene-$(C_6-C_{10})$aryl, 5-10 membered heteroaryl comprising 1, 2, 3 or 4 heteroatoms independently selected from O, S and N or —$(C_1-C_4)$alkylene-(5-10 membered heteroaryl), wherein each of the $(C_3-C_8)$cycloalkyl, —$(C_1-C_4)$alkylene-$(C_6-C_{10})$aryl, 5-10 membered heteroaryl and —$(C_1-C_4)$alkylene-(5-10 membered heteroaryl) is unsubstituted or optionally substituted with 1, 2, 3 or 4 substituents independently selected from D, F, Cl, Br, CN, $OR^a$, $NR^aR^b$, $(C_1-C_6)$alkyl, $(C_2-C_6)$alkenyl, $(C_2-C_6)$alkynyl, —$(C_1-C_4)$alkylene-$OR^a$ and —$(C_1-C_4)$alkylene-$NR^aR^b$.

In another embodiment, each of $R^a$, $R^b$ and $R^c$ in formula (I) is independently H, $(C_1-C_6)$aliphatic, $(C_1-C_6)$haloalkyl, $(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$aliphatic, $(C_1-C_6)$haloalkyl, $(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3 or 4 substituents independently selected from D, F, Cl, CN, $N_3$, OH, $NH_2$, $(C_1-C_6)$haloalkyl, $(C_1-C_6)$alkoxy and $(C_1-C_6)$alkylamino; and
$R^d$ in formula (I) is D, $(C_3-C_8)$cycloalkyl, —$(C_1-C_4)$alkylene-$(C_6-C_{10})$aryl, 5-10 membered heteroaryl comprising 1, 2, 3 or 4 heteroatoms independently selected from O, S and N or —$(C_1-C_4)$alkylene-(5-10 membered heteroaryl), wherein each of the $(C_3-C_8)$cycloalkyl, —$(C_1-C_4)$alkylene-$(C_6-C_{10})$aryl, 5-10 membered heteroaryl and —$(C_1-C_4)$alkylene-(5-10 membered heteroaryl) is unsubstituted or optionally substituted with 1, 2, 3 or 4 substituents independently selected from D, F, Cl, Br, CN, $OR^a$, $NR^aR^b$, $(C_2-C_6)$alkenyl, $(C_2-C_6)$alkynyl, —$(C_1-C_4)$alkylene-$OR^a$ and —$(C_1-C_4)$alkylene-$NR^aR^b$.

In another embodiment, Q in formula (I) is —$N(R^c)C(=O)NR^aR^b$, —$N(R^c)C(=O)R^d$ or —$C(=O)NR^aR^b$.

In another embodiment, each of X, Y and Z in formula (I) is independently $(C_1-C_4)$alkyl, $(C_3-C_6)$cycloalkyl, —$(C_1-C_2)$alkylene-$(C_3-C_6)$cycloalkyl, $(C_3-C_6)$heterocyclyl, —$(C_1-C_2)$alkylene-$(C_3-C_6)$heterocyclyl, phenyl, 5-10 membered heteroaryl comprising 1, 2, 3 or 4 heteroatoms independently selected from O, S and N, —$(C_1-C_2)$alkylene-phenyl or —$(C_1-C_2)$alkylene-(5-10 membered heteroaryl), wherein each of the $(C_1-C_4)$alkyl, $(C_3-C_6)$cycloalkyl, —$(C_1-C_2)$alkylene-$(C_3-C_6)$cycloalkyl, $(C_3-C_6)$heterocyclyl, —$(C_1-C_2)$alkylene-$(C_3-C_6)$heterocyclyl, phenyl, 5-10 membered heteroaryl, —$(C_1-C_2)$alkylene-phenyl and —$(C_1-C_2)$alkylene-(5-10 membered heteroaryl) is unsubstituted or optionally substituted with 1, 2, 3 or 4 substituents independently selected from D, F, Cl, CN, $(C_2-C_4)$alkenyl, $(C_2-C_4)$alkynyl, $OR^a$, $NR^aR^b$, —$(C_1-C_2)$alkylene-$OR^a$ and —$(C_1-C_2)$alkylene-$NR^aR^b$.

In another embodiment, each of $R^1$, $R^2$, $R^3$, $R^4$, $R^5$, $R^6$ and $R^7$ in formula (I) is independently H, D, F or Cl.

In another embodiment, each of $R^a$, $R^b$ and $R^c$ in formula (I) is independently H, $(C_1-C_4)$alkyl, $(C_1-C_4)$haloalkyl, $(C_3-C_6)$cycloalkyl, —$(C_1-C_2)$alkylene-$(C_3-C_6)$cycloalkyl, $(C_3-C_6)$heterocyclyl or —$(C_1-C_2)$alkylene-$(C_3-C_6)$heterocyclyl, wherein each of the $(C_1-C_4)$alkyl, $(C_1-C_4)$haloalkyl, $(C_3-C_6)$cycloalkyl, —$(C_1-C_2)$alkylene-$(C_3-C_6)$cycloalkyl, $(C_3-C_6)$heterocyclyl and —$(C_1-C_2)$alkylene-$(C_3-C_6)$heterocyclyl is unsubstituted or optionally substituted with 1, 2, 3 or 4 substituents independently selected from D, F, Cl, CN, $N_3$, OH, $NH_2$, $(C_1-C_3)$haloalkyl, $(C_1-C_3)$alkoxy and $(C_1-C_3)$alkylamino.

In another embodiment, $R^d$ in formula (I) is $(C_3-C_6)$cycloalkyl, wherein the $(C_3-C_6)$cycloalkyl is unsubstituted or optionally substituted with 1, 2, 3 or 4 substituents independently selected from D, F, CN, $OR^a$, $NR^aR^b$, $(C_1-C_3)$alkyl, $(C_2-C_4)$alkenyl, $(C_2-C_4)$alkynyl, —$(C_1-C_2)$alkylene-$OR^a$ and —$(C_1-C_2)$alkylene-$NR^aR^b$.

In another embodiment, each of X, Y and Z in formula (I) is independently H, D, $CH_3$, methyl group substituted with 1, 2 or 3 deuterium atoms, ethyl, propyl, isopropyl, phenyl or phenyl group substituted with 1, 2, 3, 4 or 5 substituents independently selected from D, F and Cl.

In another embodiment, Q in formula (I) is:

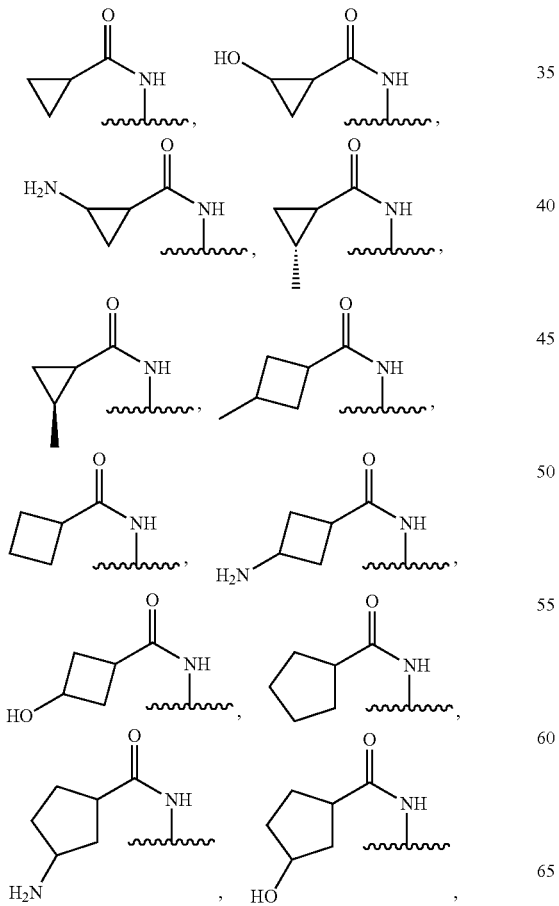

-continued

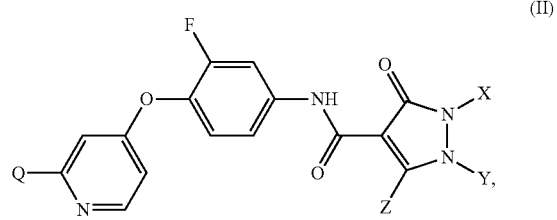

In another embodiment, the invention provides compounds having the formula (II):

(II)

wherein each of Q, X, Y and Z is as defined herein.

In certain embodiments, Q in formula (II) is —$N(R^c)C(=O)NR^aR^b$, —$N(R^c)C(=O)R^d$, —$N(R^c)S(=O)NR^aR^b$, —N(R$^c$)S(=O)R$^a$, —N(R$^c$)S(=O)$_2$NR$^a$R$^b$, —N(R$^c$)S(=O)$_2$R$^a$ or —C(=O)NR$^a$R$^b$;

each of X, Y and Z in formula (II) is independently H, D, (C$_1$-C$_6$)alkyl, (C$_3$-C$_8$)cycloalkyl, (C$_3$-C$_7$)heterocyclyl, (C$_6$-C$_{10}$)aryl, 5-10 membered heteroaryl comprising 1, 2, 3 or 4 heteroatoms independently selected from O, S and N, —(C$_1$-C$_4$)alkylene-(C$_3$-C$_8$)cycloalkyl, —(C$_1$-C$_4$)alkylene-(C$_3$-C$_7$)heterocyclyl, —(C$_1$-C$_4$)alkylene-(C$_6$-C$_{10}$)aryl or —(C$_1$-C$_4$)alkylene-(5-10 membered heteroaryl), wherein each of the (C$_1$-C$_6$)alkyl, (C$_3$-C$_8$)cycloalkyl, (C$_3$-C$_7$)heterocyclyl, (C$_6$-C$_{10}$)aryl, 5-10 membered heteroaryl, —(C$_1$-C$_4$)alkylene-(C$_3$-C$_8$)cycloalkyl, —(C$_1$-C$_4$)alkylene-(C$_3$-C$_7$)heterocyclyl, —(C$_1$-C$_4$)alkylene-(C$_6$-C$_{10}$)aryl and —(C$_1$-C$_4$)alkylene-(5-10 membered heteroaryl) is optionally substituted with 1, 2, 3, 4 or 5 substituents independently selected from D, F, Cl, Br, CN, (C$_2$-C$_6$)alkenyl, (C$_2$-C$_6$)alkynyl, OR$^a$, NR$^a$R$^b$, —(C$_1$-C$_4$)alkylene-OR$^a$ and —(C$_1$-C$_4$)alkylene-NR$^a$R$^b$;

each of R$^a$, R$^b$ and R$^c$ in formula (II) is independently H, (C$_1$-C$_6$)alkyl, (C$_3$-C$_6$)cycloalkyl, (C$_3$-C$_6$)heterocyclyl, (C$_6$-C$_{10}$)aryl, 5-10 membered heteroaryl comprising 1, 2, 3 or 4 heteroatoms independently selected from O, S and N, —(C$_1$-C$_4$)alkylene-(C$_3$-C$_6$)cycloalkyl, —(C$_1$-C$_4$)alkylene-(C$_3$-C$_6$)heterocyclyl, —(C$_1$-C$_4$)alkylene-(C$_6$-C$_{10}$)aryl or —(C$_1$-C$_4$)alkylene-(5-10 membered heteroaryl), wherein each of the (C$_1$-C$_6$)alkyl, (C$_3$-C$_6$)cycloalkyl, (C$_3$-C$_6$)heterocyclyl, (C$_6$-C$_{10}$)aryl, 5-10 membered heteroaryl, —(C$_1$-C$_4$)alkylene-(C$_3$-C$_6$)heterocyclyl, —(C$_1$-C$_4$)alkylene-(C$_6$-C$_{10}$)aryl and —(C$_1$-C$_4$)alkylene-(5-10 membered heteroaryl) is optionally substituted with 1, 2, 3 or 4 substituents independently selected from D, F, Cl, CN, N$_3$, OH, NH$_2$, (C$_1$-C$_6$)haloalkyl, (C$_1$-C$_6$)alkoxy and (C$_1$-C$_6$)alkylamino; and R$^d$ in formula (II) is (C$_3$-C$_8$)cycloalkyl, wherein the (C$_3$-C$_8$)cycloalkyl is optionally substituted with 1, 2, 3 or 4 substituents independently selected from D, F, Cl, OH, NH$_2$, (C$_1$-C$_6$)alkyl, (C$_1$-C$_6$)alkoxy and (C$_1$-C$_6$)alkylamino.

In another embodiment, Q in formula (II) is —N(R$^c$)C(=O)NR$^a$R$^b$, —N(R$^c$)C(=O)R$^d$, —N(R$^c$)S(=O)NR$^a$R$^b$, —N(R$^c$)S(=O)$_2$NR$^a$R$^b$, —N(R$^c$)S(=O)$_2$R$^a$ or —C(=O)NR$^a$R$^b$; and R$^d$ in formula (II) is (C$_3$-C$_8$)cycloalkyl, wherein the (C$_3$-C$_8$)cycloalkyl is optionally substituted with 1, 2, 3 or 4 substituents independently selected from D, F, Cl, OH, NH$_2$, (C$_1$-C$_6$)alkoxy and (C$_1$-C$_6$)alkylamino.

In another embodiment, Q in formula (II) is —N(R$^c$)C(=O)NR$^a$R$^b$, —N(R$^c$)C(=O)R$^d$ or —C(=O)NR$^a$R$^b$.

In another embodiment, each of X, Y and Z in formula (II) is independently H, D, (C$_1$-C$_4$)alkyl or phenyl, wherein each of the (C$_1$-C$_4$)alkyl and phenyl is optionally substituted with 1, 2, 3, 4 or 5 substituents independently selected from D, F and Cl.

In another embodiment, each of R$^a$, R$^b$ and R$^c$ in formula (II) is independently H, (C$_1$-C$_4$)alkyl, (C$_3$-C$_6$)cycloalkyl, (C$_3$-C$_6$)heterocyclyl, —(C$_1$-C$_2$)alkylene-(C$_3$-C$_6$)cycloalkyl or —(C$_1$-C$_2$)alkylene-(C$_3$-C$_6$)heterocyclyl, wherein each of the (C$_1$-C$_4$)alkyl, (C$_3$-C$_6$)cycloalkyl, (C$_3$-C$_6$)heterocyclyl, —(C$_1$-C$_2$)alkylene-(C$_3$-C$_6$)cycloalkyl and —(C$_1$-C$_2$)alkylene-(C$_3$-C$_6$)heterocyclyl is optionally substituted with 1, 2, 3 or 4 substituents independently selected from D, F, Cl, CN, N$_3$, OH, NH$_2$, (C$_1$-C$_6$)haloalkyl, (C$_1$-C$_6$)alkoxy and (C$_1$-C$_6$)alkylamino.

In another embodiment, each of X, Y and Z in formula (II) is independently H, D, Me, CH$_2$D, CHD$_2$, CD$_3$, ethyl, propyl, isopropyl, phenyl or phenyl group optionally substituted with 1, 2, 3, 4 or 5 substituents independently selected from D, F and Cl.

In another embodiment, Q in formula (II) is:

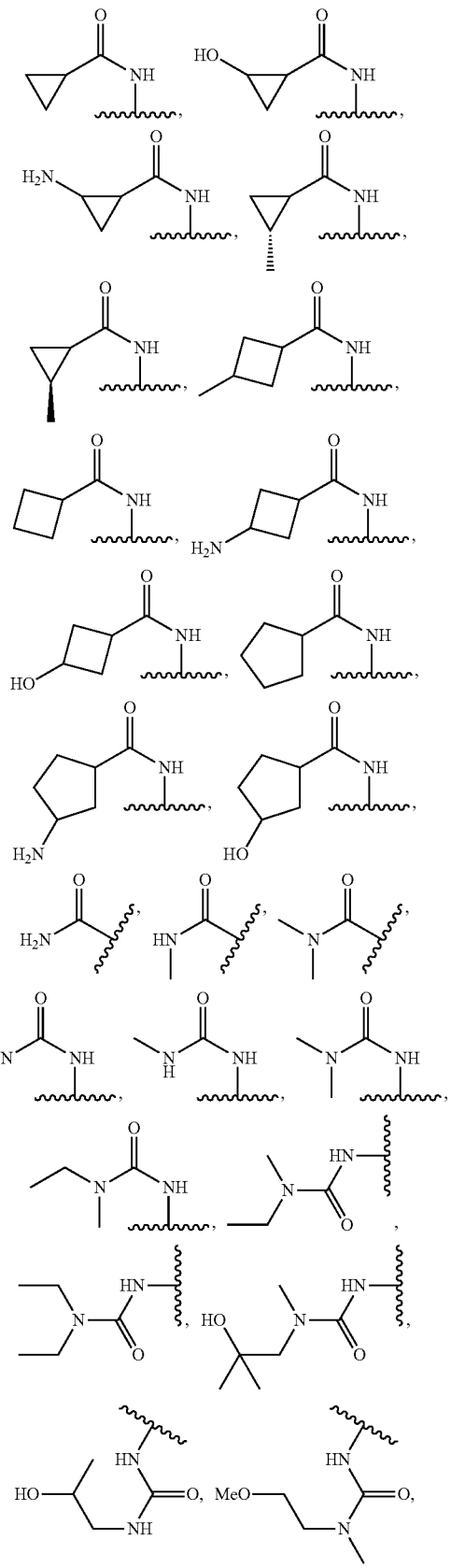

-continued
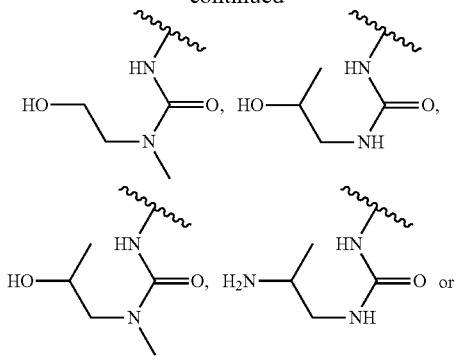
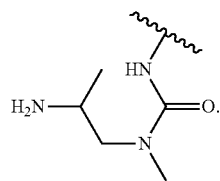
In some embodiments, non-limiting examples of compounds disclosed herein, and their pharmaceutically acceptable salts and solvates thereof, are shown in the following:
TABLE 1
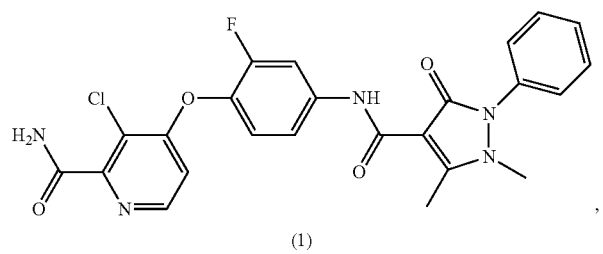 [SMILES: Cc1c(C(=O)Nc2ccc(Oc3ccnc(C(N)=O)c3Cl)c(F)c2)c(=O)n(-c2ccccc2)n1C]
(1)
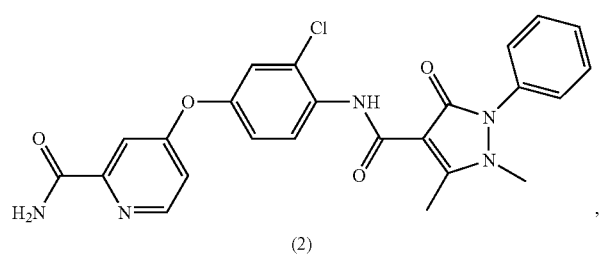 [SMILES: Cc1c(C(=O)Nc2ccc(Oc3ccnc(C(N)=O)c3)cc2Cl)c(=O)n(-c2ccccc2)n1C]
(2)
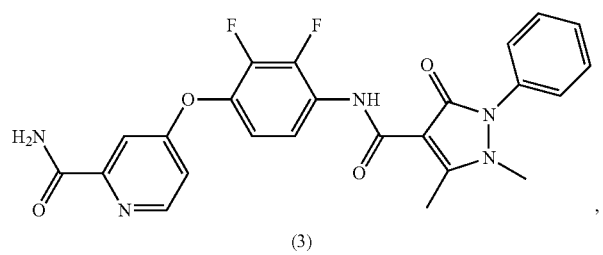 [SMILES: Cc1c(C(=O)Nc2ccc(Oc3ccnc(C(N)=O)c3)c(F)c2F)c(=O)n(-c2ccccc2)n1C]
(3)
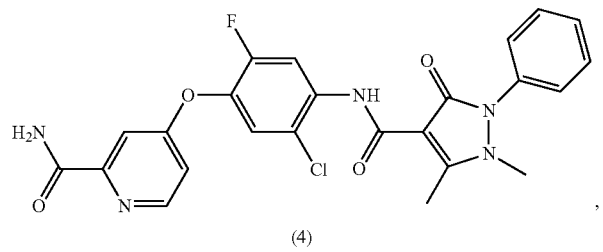 [SMILES: Cc1c(C(=O)Nc2cc(F)c(Oc3ccnc(C(N)=O)c3)cc2Cl)c(=O)n(-c2ccccc2)n1C]
(4)

TABLE 1-continued
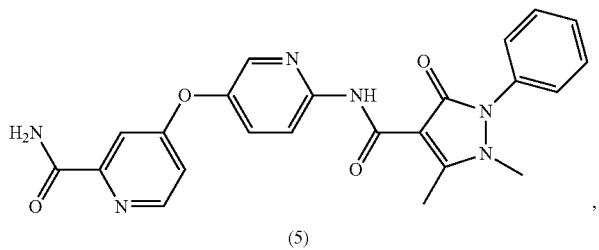
(5)
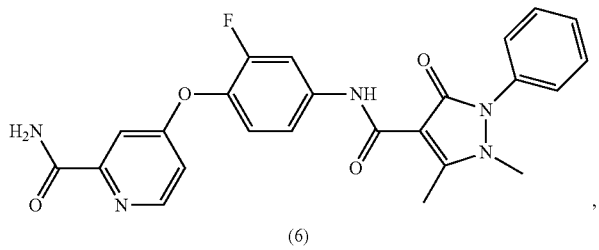 [SMILES: Cc1c(C(=O)Nc2ccc(Oc3ccnc(C(N)=O)c3)c(F)c2)c(=O)n(-c2ccccc2)n1C]
(6)
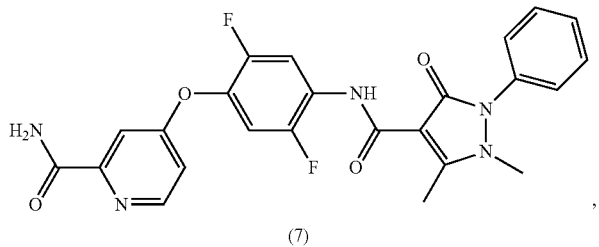
(7)
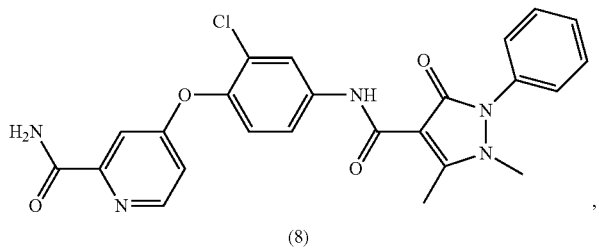 [SMILES: Cc1c(C(=O)Nc2ccc(Oc3ccnc(C(N)=O)c3)c(Cl)c2)c(=O)n(-c2ccccc2)n1C]
(8)
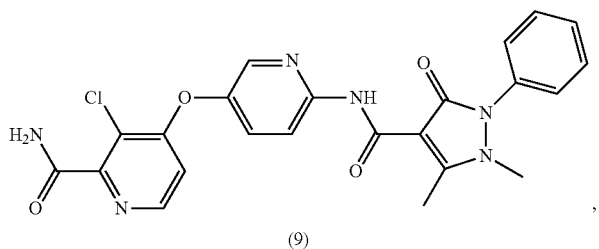
(9)
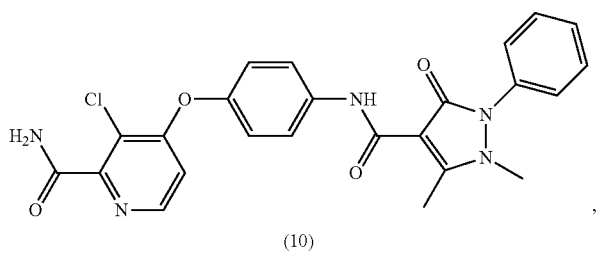 [SMILES: Cc1c(C(=O)Nc2ccc(Oc3ccnc(C(N)=O)c3Cl)cc2)c(=O)n(-c2ccccc2)n1C]
(10)

TABLE 1-continued
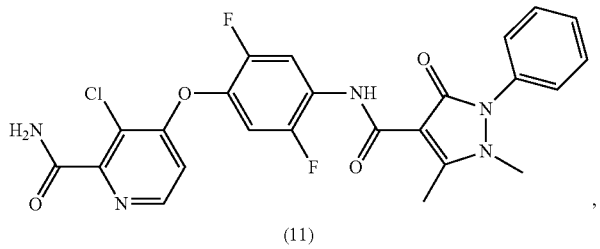 [SMILES: Cc1c(C(=O)Nc2cc(F)c(Oc3ccnc(C(N)=O)c3Cl)cc2F)c(=O)n(-c2ccccc2)n1C]
(11)
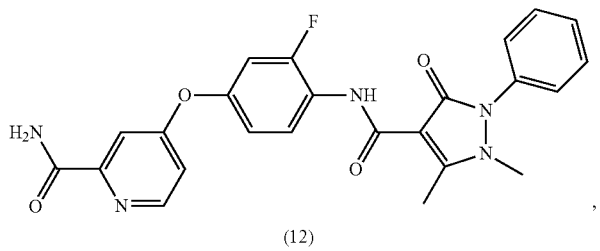
(12)
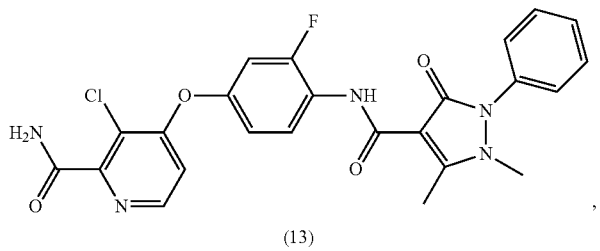 [SMILES: Cc1c(C(=O)Nc2ccc(Oc3ccnc(C(N)=O)c3Cl)cc2F)c(=O)n(-c2ccccc2)n1C]
(13)
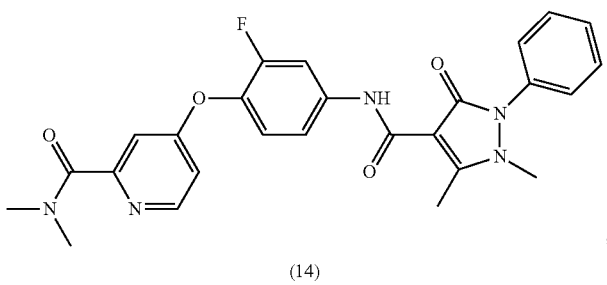
(14)
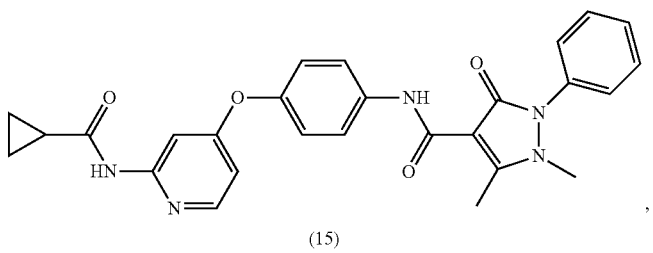
(15)
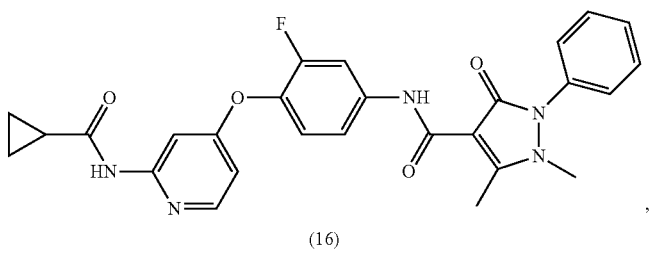 [SMILES: Cc1c(C(=O)Nc2ccc(Oc3ccnc(NC(=O)C4CC4)c3)cc2)c(=O)n(-c2ccccc2)n1C]
(16)

TABLE 1-continued
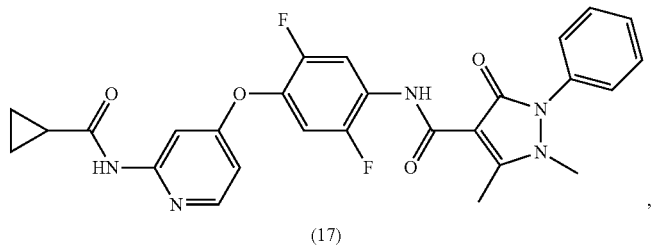 [SMILES: Cc1c(C(=O)Nc2cc(F)c(Oc3ccnc(NC(=O)C4CC4)c3)cc2F)c(=O)n(-c2ccccc2)n1C]
(17)
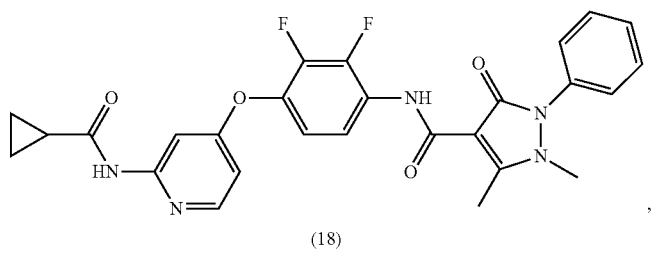 [SMILES: Cc1c(C(=O)Nc2ccc(Oc3ccnc(NC(=O)C4CC4)c3)c(F)c2F)c(=O)n(-c2ccccc2)n1C]
(18)
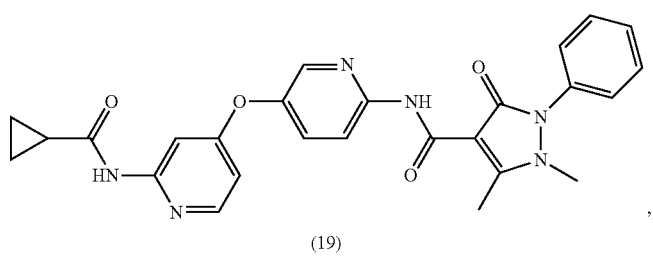
(19)
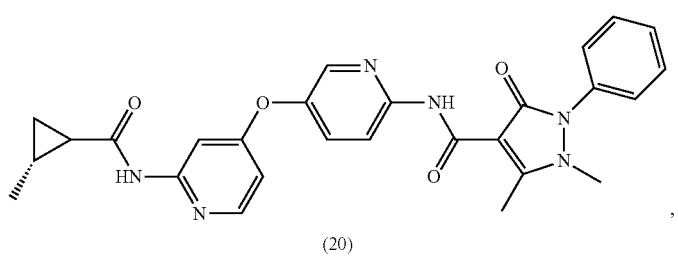 [SMILES: Cc1c(C(=O)Nc2ccc(Oc3ccnc(NC(=O)C4C[C@H]4C)c3)cn2)c(=O)n(-c2ccccc2)n1C]
(20)
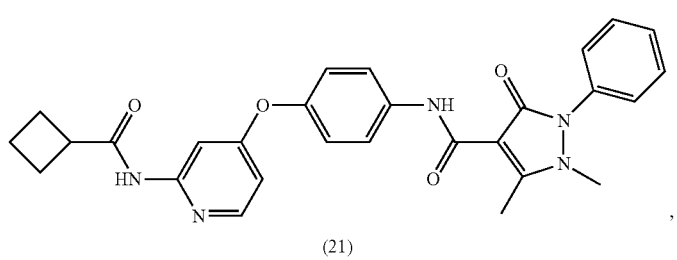
(21)
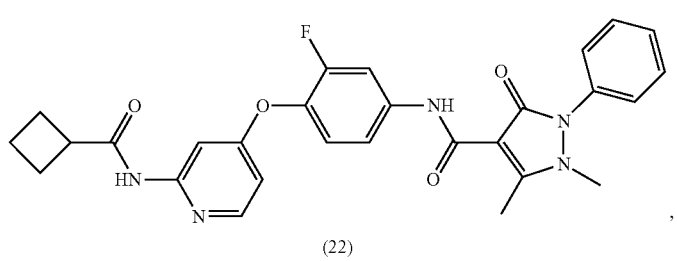
(22)

TABLE 1-continued
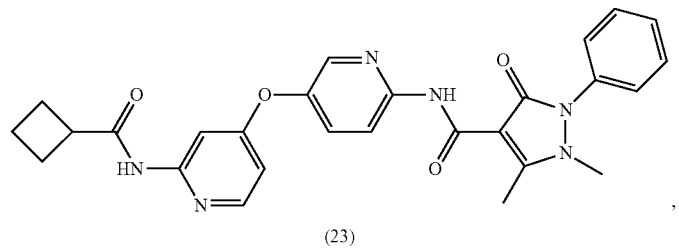 [SMILES: Cc1c(C(=O)Nc2ccc(Oc3ccnc(NC(=O)C4CCC4)c3)cc2)c(=O)n(-c2ccccc2)n1C]
(23)
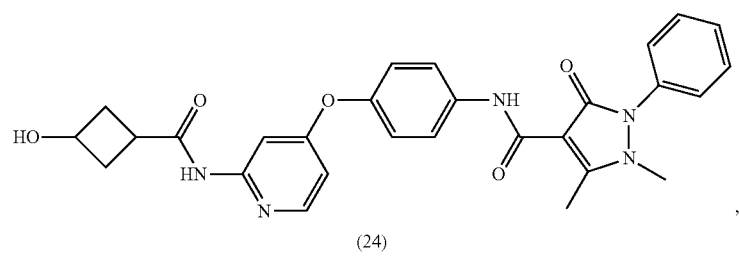 [SMILES: Cc1c(C(=O)Nc2ccc(Oc3ccnc(NC(=O)C4CC(O)C4)c3)cc2)c(=O)n(-c2ccccc2)n1C]
(24)
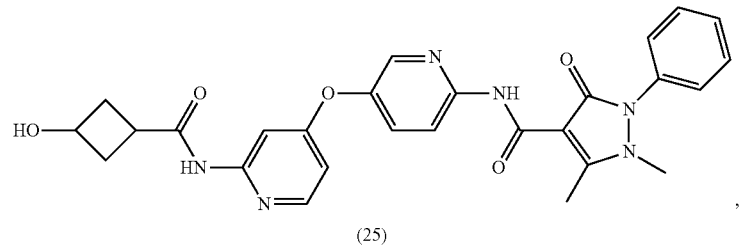 [SMILES: Cc1c(C(=O)Nc2ccc(Oc3ccnc(NC(=O)C4CC(O)C4)c3)cn2)c(=O)n(-c2ccccc2)n1C]
(25)
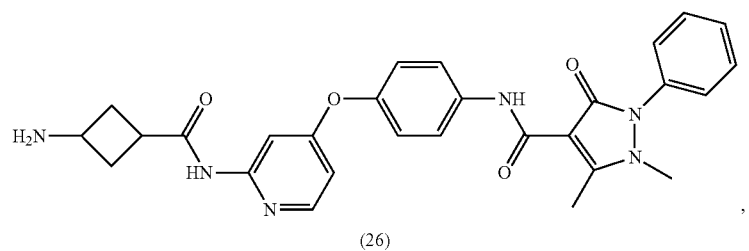 [SMILES: Cc1c(C(=O)Nc2ccc(Oc3ccnc(NC(=O)C4CC(N)C4)c3)cc2)c(=O)n(-c2ccccc2)n1C]
(26)
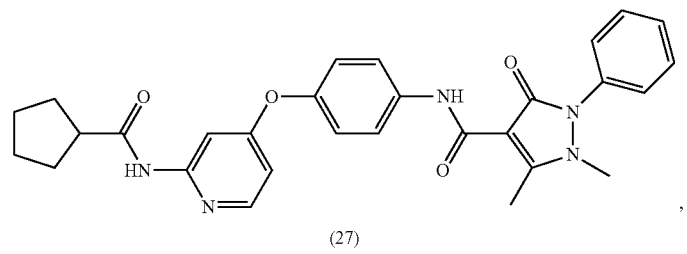 [SMILES: Cc1c(C(=O)Nc2ccc(Oc3ccnc(NC(=O)C4CCCC4)c3)cc2)c(=O)n(-c2ccccc2)n1C]
(27)
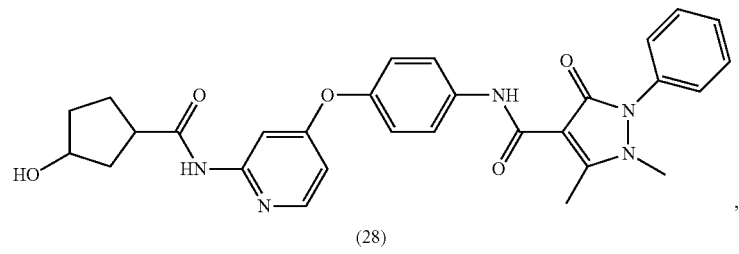 [SMILES: Cc1c(C(=O)Nc2ccc(Oc3ccnc(NC(=O)C4CCC(O)C4)c3)cc2)c(=O)n(-c2ccccc2)n1C]
(28)

TABLE 1-continued
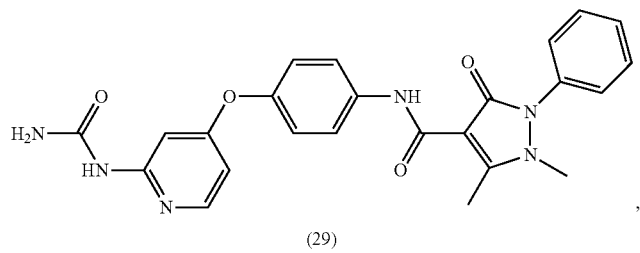 [SMILES: Cc1c(C(=O)Nc2ccc(Oc3ccnc(NC(N)=O)c3)cc2)c(=O)n(-c2ccccc2)n1C]
(29)
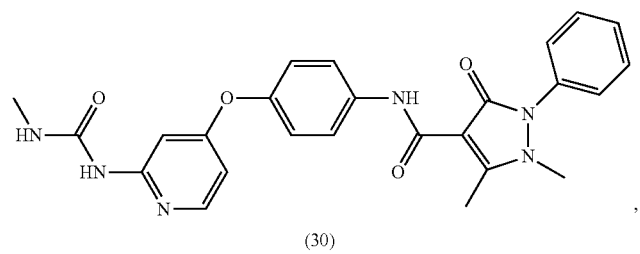 [SMILES: CNC(=O)Nc1cc(Oc2ccc(NC(=O)c3c(C)n(C)n(-c4ccccc4)c3=O)cc2)ccn1]
(30)
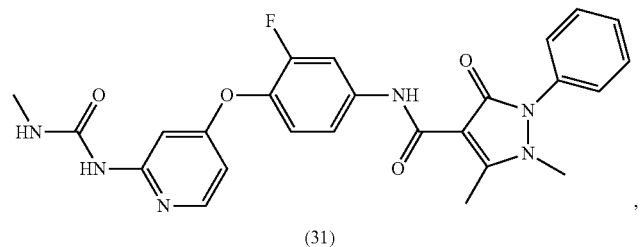 [SMILES: CNC(=O)Nc1cc(Oc2ccc(NC(=O)c3c(C)n(C)n(-c4ccccc4)c3=O)cc2F)ccn1]
(31)
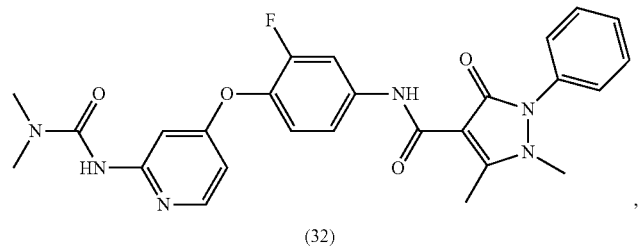 [SMILES: Cc1c(C(=O)Nc2ccc(Oc3ccnc(NC(=O)N(C)C)c3)c(F)c2)c(=O)n(-c2ccccc2)n1C]
(32)
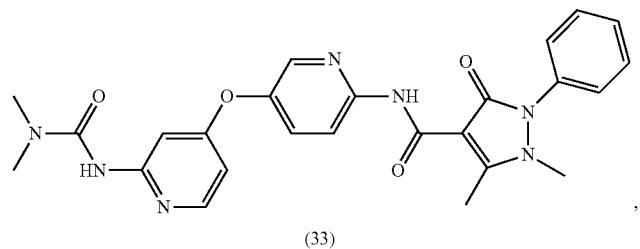 [SMILES: Cc1c(C(=O)Nc2ccc(Oc3ccnc(NC(=O)N(C)C)c3)cn2)c(=O)n(-c2ccccc2)n1C]
(33)
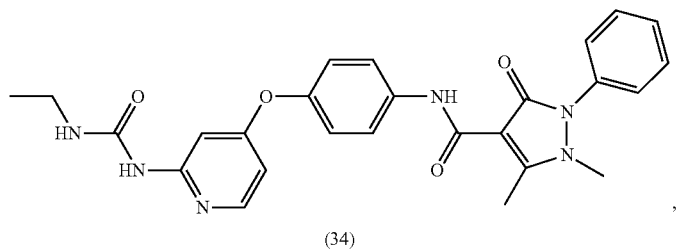 [SMILES: CCNC(=O)Nc1cc(Oc2ccc(NC(=O)c3c(C)n(C)n(-c4ccccc4)c3=O)cc2)ccn1]
(34)

TABLE 1-continued
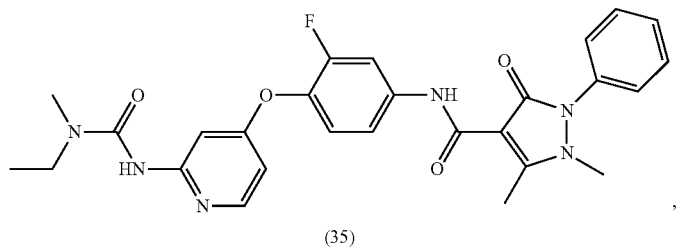 [SMILES: CCN(C)C(=O)Nc1cc(Oc2ccc(NC(=O)c3c(C)n(C)n(-c4ccccc4)c3=O)cc2F)ccn1]
(35)
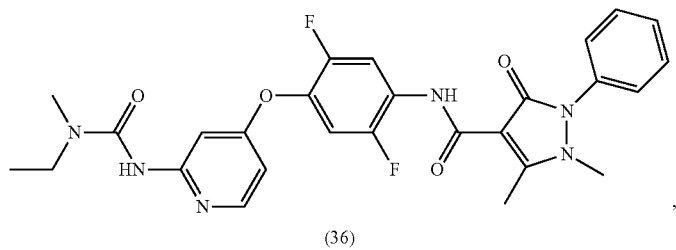 [SMILES: CCN(C)C(=O)Nc1cc(Oc2cc(F)c(NC(=O)c3c(C)n(C)n(-c4ccccc4)c3=O)cc2F)ccn1]
(36)
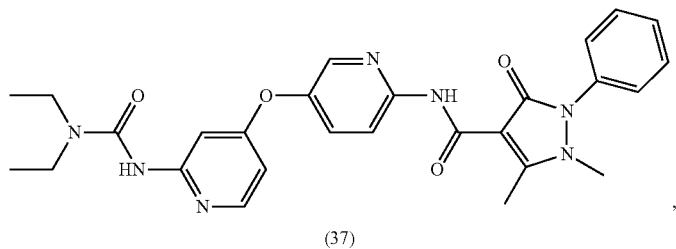 [SMILES: CCN(CC)C(=O)Nc1cc(Oc2ccc(NC(=O)c3c(C)n(C)n(-c4ccccc4)c3=O)nc2)ccn1]
(37)
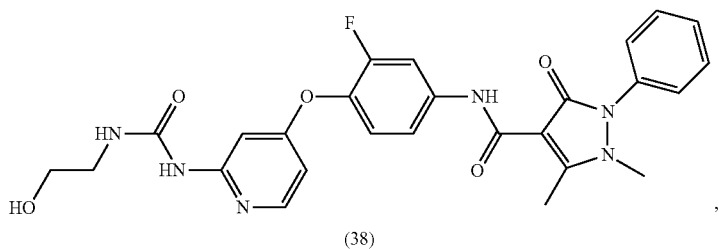
(38)
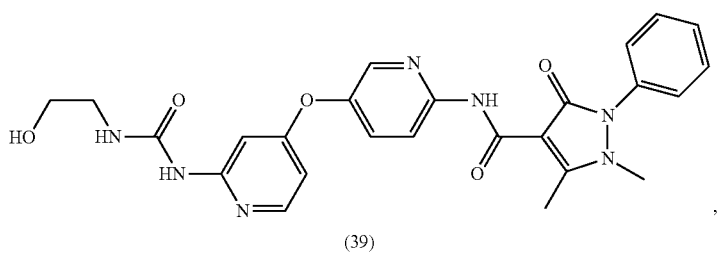 [SMILES: Cc1c(C(=O)Nc2ccc(Oc3ccnc(NC(=O)NCCO)c3)cn2)c(=O)n(-c2ccccc2)n1C]
(39)
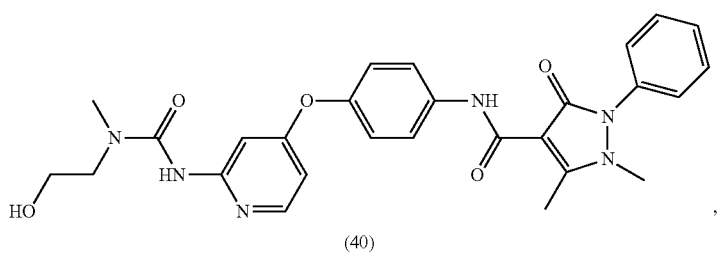 [SMILES: Cc1c(C(=O)Nc2ccc(Oc3ccnc(NC(=O)N(C)CCO)c3)cc2)c(=O)n(-c2ccccc2)n1C]
(40)

TABLE 1-continued
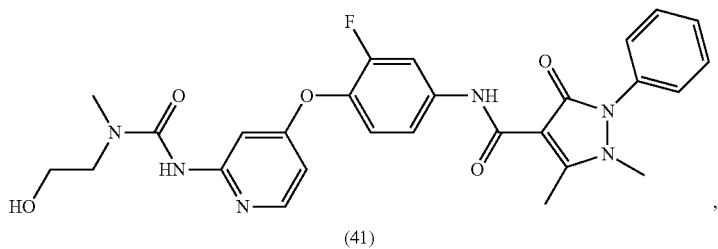 [SMILES: Cc1c(C(=O)Nc2ccc(Oc3ccnc(NC(=O)N(C)CCO)c3)c(F)c2)c(=O)n(-c2ccccc2)n1C]
(41)
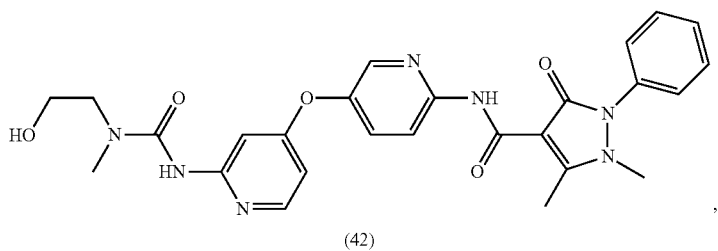 [SMILES: Cc1c(C(=O)Nc2ccc(Oc3ccnc(NC(=O)N(C)CCO)c3)cn2)c(=O)n(-c2ccccc2)n1C]
(42)
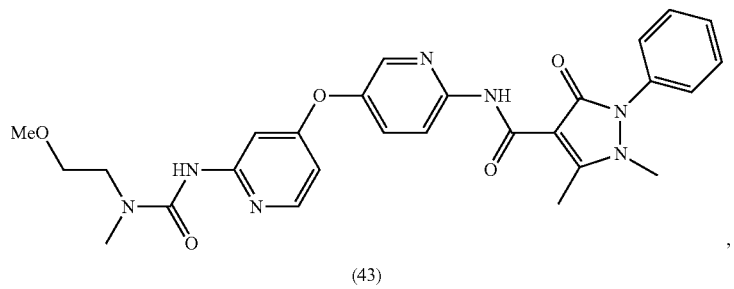 [SMILES: COCCN(C)C(=O)Nc1cc(Oc2ccc(NC(=O)c3c(C)n(C)n(-c4ccccc4)c3=O)nc2)ccn1]
(43)
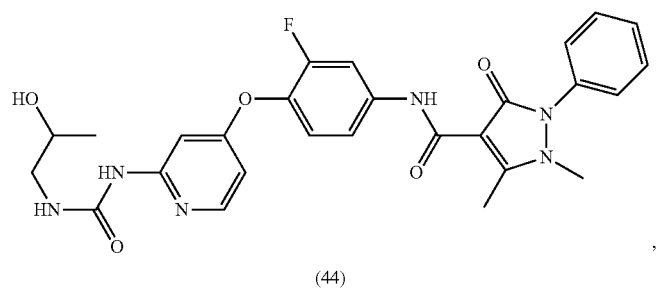 [SMILES: Cc1c(C(=O)Nc2ccc(Oc3ccnc(NC(=O)NCC(C)O)c3)c(F)c2)c(=O)n(-c2ccccc2)n1C]
(44)
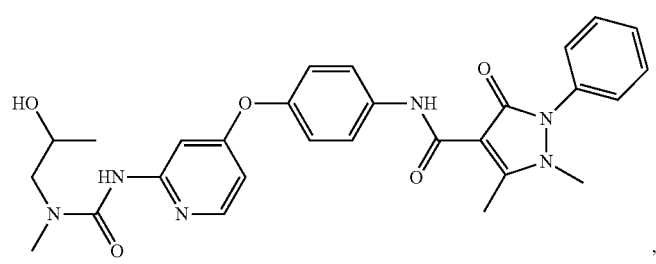
(45)
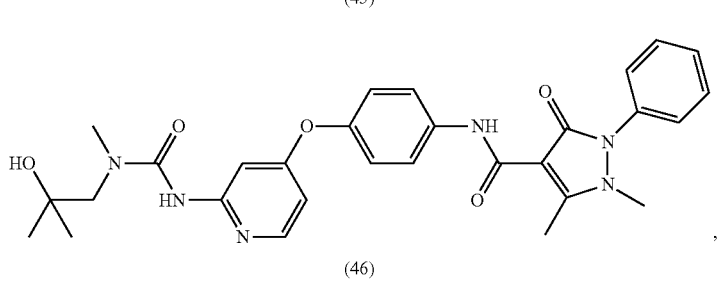
(46)

TABLE 1-continued

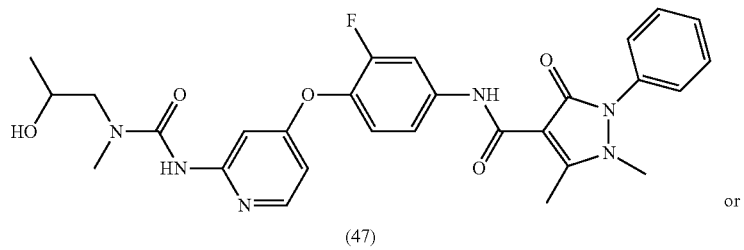 [SMILES: Cc1c(C(=O)Nc2ccc(Oc3ccnc(NC(=O)N(C)CC(C)O)c3)c(F)c2)c(=O)n(-c2ccccc2)n1C]

(47)

or

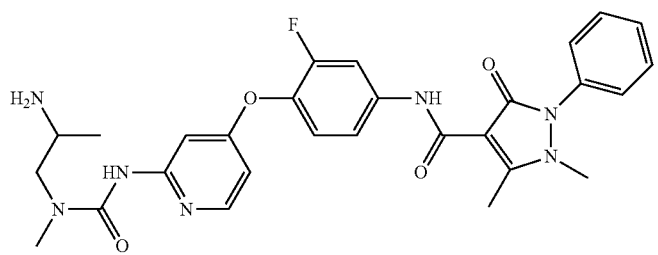

(48)

The present invention also comprises the use of a compound disclosed herein, or pharmaceutically acceptable salt thereof, in the manufacture of a medicament for the treatment either acutely or chronically of a hyperproliferative disease state and/or an angiogenesis mediated disease state, including those described previously. The compounds disclosed herein are useful in the manufacture of an anti-cancer medicament. The compounds disclosed herein are also useful in the manufacture of a medicament to attenuate or prevent disorders through inhibition of protein kinases. The present invention comprises a pharmaceutical composition comprising a therapeutically effective amount of a compound of Formula (I) or (II) in association with at least one pharmaceutically acceptable carrier, adjuvant or diluent.

The present invention also comprises a method of treating hyperproliferating and angiogenesis related disorders in a subject having or susceptible to such disorder, the method comprising treating the subject with a therapeutically effective amount of a compound of Formula (I) or (II).

Unless otherwise stated, all stereoisomers, geometric isomers, tautomers, solvates, hydrates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

The compounds disclosed herein also include salts of such compounds which are not necessarily pharmaceutically acceptable salts, and which may be useful as intermediates for preparing and/or purifying compounds of Formula (I) or (II) and/or for separating enantiomers of compounds of Formula (I) or (II).

The desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Composition, Formulations and Administration of the Compounds Disclosed Herein

In one aspect, featured herein are pharmaceutical compositions that include a compound of formula (I) or (II), or a compound listed in Table 1; and a pharmaceutically acceptable carrier, adjuvant, or vehicle. The amount of compound in the pharmaceutical compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. Some non-limiting examples of pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As described above, the pharmaceutical compositions or pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions disclosed herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions disclosed herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions disclosed herein may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions disclosed herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds disclosed herein include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions disclosed herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds disclosed herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polythylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds disclosed herein that may be combined with the carrier materials to produce a composition in a single dosage form will vary depending upon the host treated, the particular mode of administration. Preferably, the compositions should be formulated so that a dosage of between 0.01-200 mg/kg body weight/day of the inhibitor can be administered to a patient receiving these compositions.

The compounds disclosed herein can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compound disclosed herein can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include chemotherapeutic agents and other anti-proliferative agents.

For example, chemotherapeutic agents or other antiproliferative agents may be combined with the compounds disclosed herein to treat proliferative disease or cancer. Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Ser. No. 11/393,380.

In another embodiment of the present invention, for example, chemotherapeutic agents or other anti-proliferative agents may be combined with the compounds disclosed herein to treat proliferative diseases and cancer. Examples of known chemotherapeutic agents include, but are not limited to, for example, other therapies or anticancer agents that may be used in combination with the inventive anticancer agents of the present invention and include surgery, radiotherapy (in but a few examples, gamma radiation, neutron beam radiotherapy, electron beam radiotherapy, proton therapy, brachytherapy, and systemic radioactive isotopes, to name a few), endocrine therapy, taxanes (TAXOL®, taxotere etc), platinum derivatives, biologic response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), GLEEVEC®, adriamycin, dexamethasone, and cyclophosphamide. Antiangiogenic agents (Avastin and others). Monoclonal antibodies (Belimumab (BENLYSTA®), Brentuximab (ADCETRIS®), Cetuximab (ERBITUX®), Gemtuzumab (MYLOTARG®), Ipilimumab (YERVOY®), Ofatumumab (ARZERR®), Panitumumab (VECTIBIX®), Ranibizumab (LUCENTIS®), Rituximab (RITUXAN®), Tositumomab (BEXXAR®), Trastuzumab (HERCEPTIN®)). Kinase inhibitors (Imatinib (GLEEVEC®), Sunitinib (SUTENT®), Sorafenib (NEXAVAR®), Cetuximab (ERBITUX®), Trastuzumab (HERCEPTIN®), Erlotinib (TARCEVA®), Gefitinib (IRESSA®), Dasatinib (SPRYCEL®), Nilotinib (TASIGNA®), Lapatinib (TYKERB®), Crizotinib (XALKORI®), Ruxolitinib (JAKAFI®), Vemurafenib (ZELBORAF®), Vandetanib (CAPRELSA®), Pazopanib (VOTRIENT®), and others). Agents inhibiting or activating cancer pathways such as the mTOR, HIF (hypoxia induced factor) pathways (such as Everolimus and Temsirolimus) and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, the entire contents of which are hereby incorporated by reference.

In other embodiments, the compounds disclosed herein can be combined, with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds disclosed herein include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds disclosed herein also include newly discovered cytotoxic principles such as oxaliplatin, gemcitabine, capecitabine, epothilone and its natural or synthetic derivatives, temozolomide (Quinn et al., J. Clin. Oncology 2003, 21(4), 646-651), tositumomab (BEXXAR®), trabedectin (Vidal et al., Proceedings of the American Society for Clinical Oncology, 2004, 23, abstract 3181), and the inhibitors of the kinesin spindle protein Eg5 (Wood et al., Curr. Opin. Pharmacol. 2001, 1, 370-377).

In other embodiments, the compounds disclosed herein can be combined with other signal transduction inhibitors. Examples of such agents include, by no way of limitation, antibody therapies such as trastuzumab (HERCEPTIN®), cetuximab (ERBITUX®), ipilimumab (YERVOY®) and pertuzumab. Examples of such therapies also include, by no way of limitation, small-molecule kinase inhibitors such as Imatinib (GLEEVEC®), Sunitinib (SUTENT®), Sorafenib (NEXAVAR®), Erlotinib (TARCEVA®), Gefitinib (IRESSA®), Dasatinib (SPRYCEL®), Nilotinib (TASIGNA®), Lapatinib (TYKERB®), Crizotinib (XALKORI®), Ruxolitinib (JAKAFI®), Vemurafenib (ZELBORAF®), Vandetanib (CAPRELSA®), Pazopanib (VOTRIENT®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TKI258, GDC-0941 (Folkes, et al., J. Med. Chem., 2008, 51, 5522), BZE235, and others.

In other embodiments, the compounds disclosed herein can be combined with inhibitors of histone deacetylase. Examples of such agents include, by no way of limitation, suberoylanilide hydroxamic acid (SAHA), LAQ-824 (Ottmann et al., Proceedings of the American Society for Clinical Oncology, 2004, 23, abstract 3024), LBH-589 (Beck et al., Proceedings of the American Society for Clinical Oncology, 2004, 23, abstract 3025), MS-275 (Ryan et al., Proceedings of the American Association of Cancer Research, 2004, 45, abstract 2452), FR-901228 (Piekarz et al., Proceedings of the American Society for Clinical Oncology, 2004, 23, abstract 3028) and MGCDO1 03 (U.S. Pat. No. 6,897,220).

In other embodiments, the compounds disclosed herein can be combined with other anti-cancer agents such as proteasome inhibitors, and m-TOR inhibitors. These include, by no way of limitation, bortezomib, and CCI-779 (Wu et al., Proceedings of the American Association of Cancer Research, 2004, 45, abstract 3849). The compounds disclosed herein can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

Uses of the Compounds and Compositions Disclosed Herein

The invention features pharmaceutical compositions that include a compound of formula (I) or (II), or a compound listed in Table 1, and a pharmaceutically acceptable carrier, adjuvant, or vehicle. The amount of compound in the compositions disclosed herein is such that is effective to detectably inhibit a protein kinase, such as VEGFR, c-Met, Ron or Axl inhibitory activity. The compounds disclosed herein are useful in therapy as antineoplasia agents or to minimize deleterious effects of VEGFR, c-Met, Ron and/or Axl receptor signaling.

The compounds disclosed herein would be useful for, but not limited to, the prevention or treatment of proliferative diseases, condition, or disorder in a patient by administering to the patient a compound or a composition disclosed herein in an effective amount. Such diseases, conditions, or disorders include cancer, particularly metastatic cancer, atherosclerosis, and lung fibrosis.

The compounds disclosed herein would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds disclosed herein also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds disclosed herein are also useful in the reduction of metastasis of a tumor in a subject.

Besides being useful for human treatment, the compounds disclosed herein are also useful for veterinary treatment of companion animals, exotic animals and farm animals, including mammals, rodents, and the like. More preferred animals include horses, dogs, and cats. As used herein, the compounds disclosed herein include the pharmaceutically acceptable derivatives thereof.

Where the plural form is used for compounds, salts, and the like, this is taken to mean also a single compound, salt and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

The invention also features a method of inhibiting the growth of a cell that expresses VEGFR, c-Met, Ron or Axl that includes contacting the cell with a compound or composition disclosed herein, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

The invention provides a method of inhibiting VEGFR, c-Met, Ron or Axl kinase activity in a biological sample that includes contacting the biological sample with a compound or composition disclosed herein. The term "biological sample" as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly VEGFR, c-Met, Ron or Axl kinase activity, in a biological sample is useful for a variety of purposes known to one of skill in the art. Examples of such purposes include, but are not limited to, blood transfusion, organ-transplantation, biological specimen storage, and biological assays.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds disclosed herein or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

Suitable coatings and the general preparation of coated implantable devices are described in U.S. Pat. Nos. 6,099,562; 5,886,026; and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound disclosed herein are another embodiment of the present invention. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for formula (I) or (II), above, except where further noted. The following non-limiting schemes and examples are presented to further exemplify the invention. Persons skilled in the art will recognize that the chemical reactions described herein may be readily adapted to prepare a number of other compounds disclosed herein, and alternative methods for preparing the compounds disclosed herein are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep Co., Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co., Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, DMSO-$d_6$, $CD_3OD$ or acetone-$d_6$ solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were generally determined on an Agilent 1200 Series LCMS (Zorbax SB-C18, 2.1×30 mm, 4 micron, 10 minutes run, 0.6 mL/min flow rate, 5% to 95% (0.1% formic acid in $CH_3CN$) in (0.1% formic acid in $H_2O$)) with UV detection at 210/254 nm and a low resonance electrospray mode (ESI).

Purities of compounds were assessed by Agilent 1100 Series high performance liquid chromatography (HPLC) with UV detection at 210 nm and 254 nm. Column was normally operated at 40° C.

The following abbreviations are used throughout the specification:
ATP Adenosine Triphosphate
BINAP 2,2'-bis(diphenylphosphino)-1,1'-binaphthyl
$BBr_3$ boron tribromide
BSA bovine serum albumin
BOC, Boc butyloxycarbonyl
$Ca(SO_3CF_3)_2$ calcium trifluoromethyl sulfonate
$Cs_2CO_3$ cesium carbonate
$CH_2Cl_2$, DCM methylene chloride
$CHCl_3$ chloroform
$CDCl_3$ chloroform deuterated
Cu copper
CuI cuprous iodide
DBU 1,8-diazabicyclo[5.4.0]undec-7-ene
$D_2$ deuterium gas
DIBAL diisobutylaluminum hydride
DIAD diisopropyl azodicarboxylate
DIEA, DIPEA, $iPr_2Net$ N,N-Diisopropylethylamine
DEAD dimethyl azodicarboxylate
DMF dimethylformamide
DMAP 4-dimethylaminopyridine
DMSO dimethylsulfoxide
DPPA diphenylphosphoryl azide
DTT DL-Dithiothreitol
EDC, EDCI 1-(3-dimethylaminopropyl)-3-ethylcarbodiimide hydrochloride
EDTA ethylenediaminetetraacetic acid
$Et_3N$, TEA triethylamine
EtOAc, EA, ethyl acetate
$Et_2O$ diethyl ether
EtOH ethanol
FBS fetal bovine serum
Fe iron
g gram
h hour
HATU 2-(7-Aza-1H-benzotriazole-1-yl)-1,1,3,3-tetramethyluronium hexafluorophosphate
HBr hydrobromic acid
HCl hydrochloric acid
HOAc acetic acid
HOAT 1-Hydroxy-7-azabenzotriazole
HOBt 1-hydroxybenzotriazole hydrate
$H_2$ hydrogen
$H_2O$ water
$H_2O_2$ hydrogen peroxide
$H_3PO_4$ orthophosphoric acid
$H_2SO_4$ sulphuric acid
$HNO_3$ nitric acid
HCOOK Potassium formate
LiHMDS lithium bis(trimethylsilyl)-amide
LDA Lithium diisopropylamide
MBP myelin basic protein
MCPBA meta-chloroperbenzoic acid
MeCN, $CH_3CN$ acetonitrile
$MgSO_4$ magnesium sulfate
MeOH, $CH_3OH$ methanol
MeI methyl iodide
MOPS 3-(N-Morpholino)propanesulfonic acid
2-MeTHF 2-methyl tetrahydrofuran
mL, ml milliliter
$N_2$ nitrogen
NMP N-methylpyrrolidinone
$NaHCO_3$ sodium bicarbonate
$NaBH_4$ sodium borohydride
$NaBH_3CN$ sodium cyanoborohydride
NaOtBu sodium tert-butoxide
NaOH sodium hydroxide
$NaClO_2$ sodium chlorite
NaClO sodium hypochlorite
NaCl sodium chloride
$NaH_2PO_4$ sodium biphosphate
NaH sodium hydride
NaI sodium iodide
$Na_2SO_4$ sodium sulfate
$NH_3$ ammonia
$NH_4Cl$ ammonium chloride
Pd/C palladium on carbon
$Pd_2(dba)_3$ bis(dibenzylideneacetone) palladium
$Pd(OAc)_2$ palladium acetate
$Pd(OH)_2$ palladium hydroxide
$Pd(PPh_3)_4$ palladium tetrakis triphenylphosphine
$Pd(dppf)Cl_2$ 1,1-bis(diphenylphosphino)ferrocene palladium chloride
$P(t-Bu)_3$ tri(tert-butyl)phosphine
PE petroleum ether (60-90° C.)
PBS phosphate buffered saline
$POCl_3$ phosphorous oxychloride
$PhI(OAc)_2$ iodobenzene diacetate
$K_2CO_3$ potassium carbonate
KOH potassium hydroxide
RT rt r.t. room temperature
Rt retention time
$SOCl_2$ thionyl chloride t-BuOK Potassium tert-butanolate
TBTU O-benzotriazol-1-yl-N,N,N',N'-tetramethyluronium tetrafluoroborate
TBS tris buffered saline
THF tetrahydrofuran
TFA trifluoroacetic acid
TEAC bis(tetra-ethylammonium)carbonate
Tris trihydroxymethyl aminomethane Representative synthetic procedures for the preparation of the compounds disclosed herein are outlined below in following schemes. Unless otherwise indicated, each of X, Y, Z, W, $R^1$, $R^2$, $R^3$, $R^4$, $R^5$, $R^6$ and $R^d$ carry the definitions set forth above in connection with formula (I) or (II).

Scheme 1

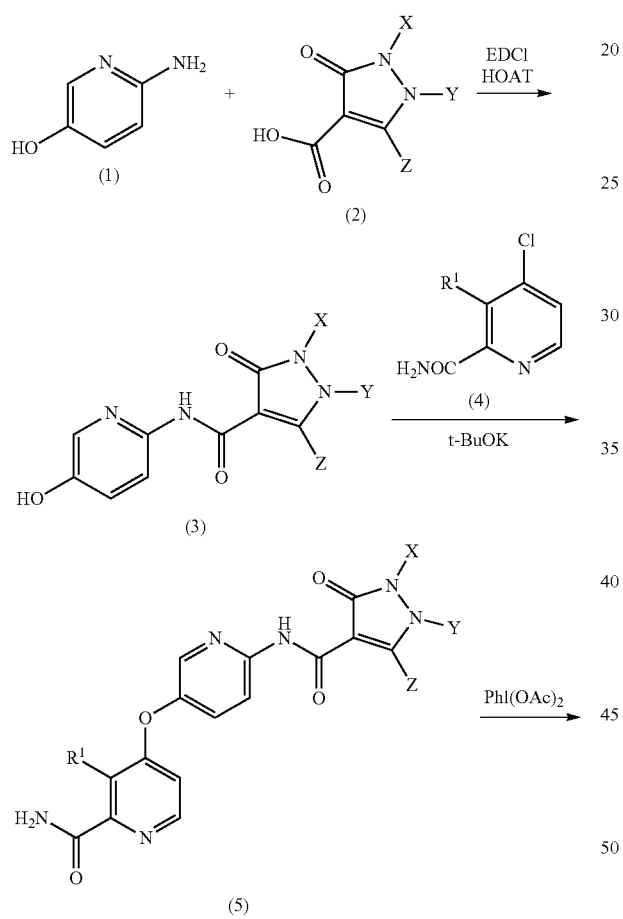

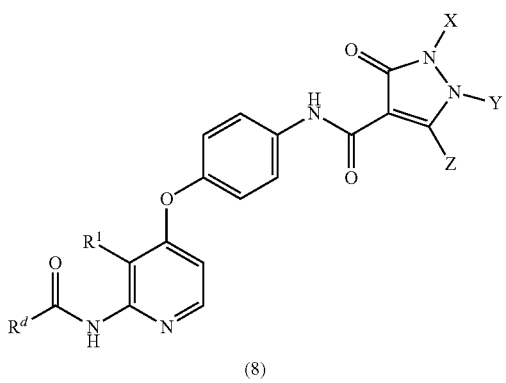

The compounds disclosed herein can be prepared according to the general synthetic methods illustrated in Scheme 1 and described in details in the Examples. Referring to Scheme 1, 6-aminopyridin-3-ol (1) is first condensed with substituted pyrazolone (2) to provide compound (3). Coupling of picolinamide (4) with compound (3) under basic condition (for example, t-BuOK or NaH) at an elevated temperature in a polar solvent such as DMF affords the desired amide (5). Rearrangement of the amide in the presence of an oxidant, such as PhI(OAc)$_2$ or NaClO leads to aminopyridine (6). Acylation of aminopyridine (6) with acyl chloride (7) gives kinase inhibitor (8).

Scheme 2

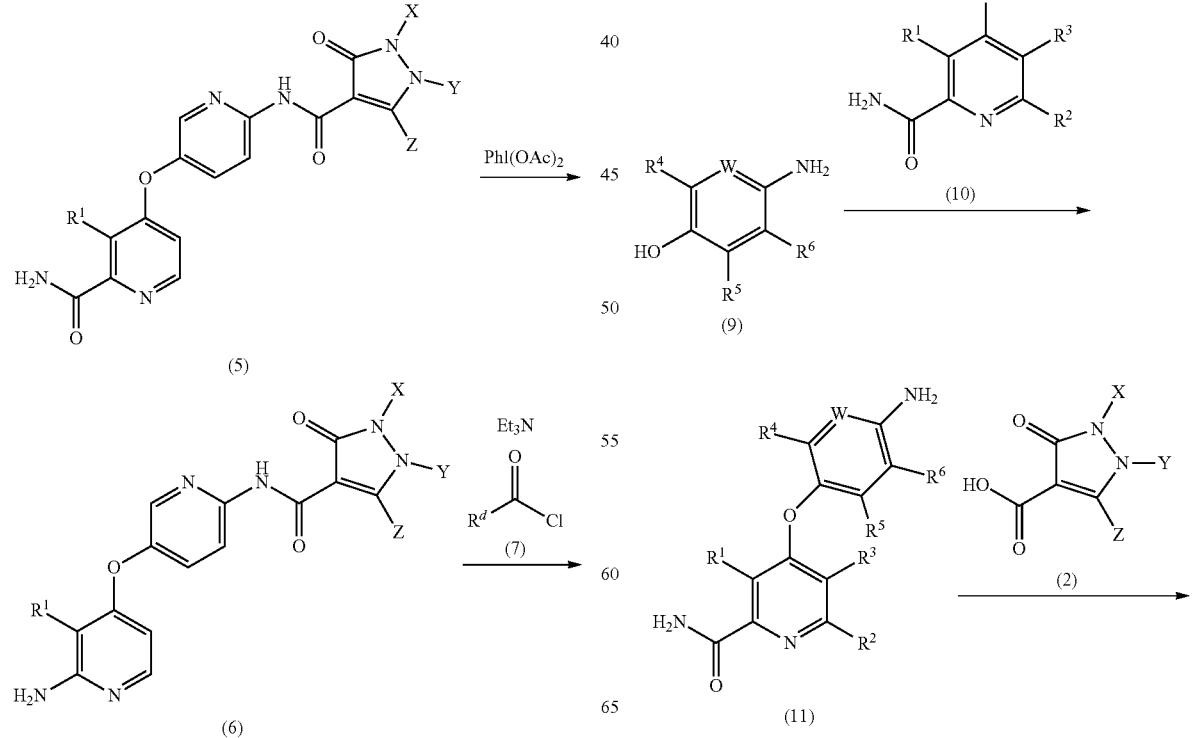

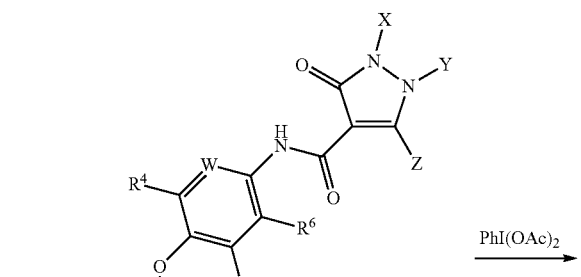

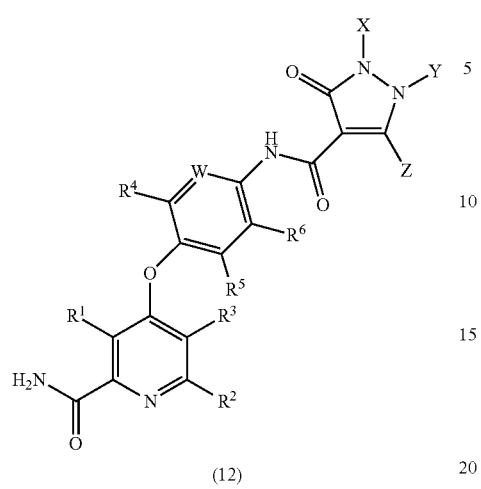

Alternatively, the compounds disclosed herein can also be prepared using the synthetic route as shown in Scheme 2. Referring to Scheme 2, aryl compound (9) (with a free OH group) is coupled with substituted pyridine (10) at an elevated temperature to afford diaryl ether (11). Condensation of diaryl ether (11) with substituted pyrazolone (2) leads to the desired kinase inhibitor (12).

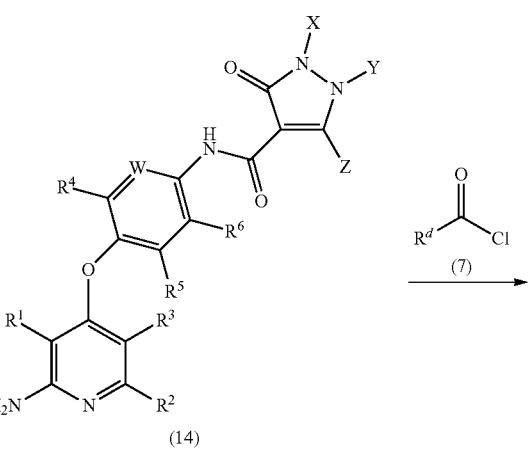

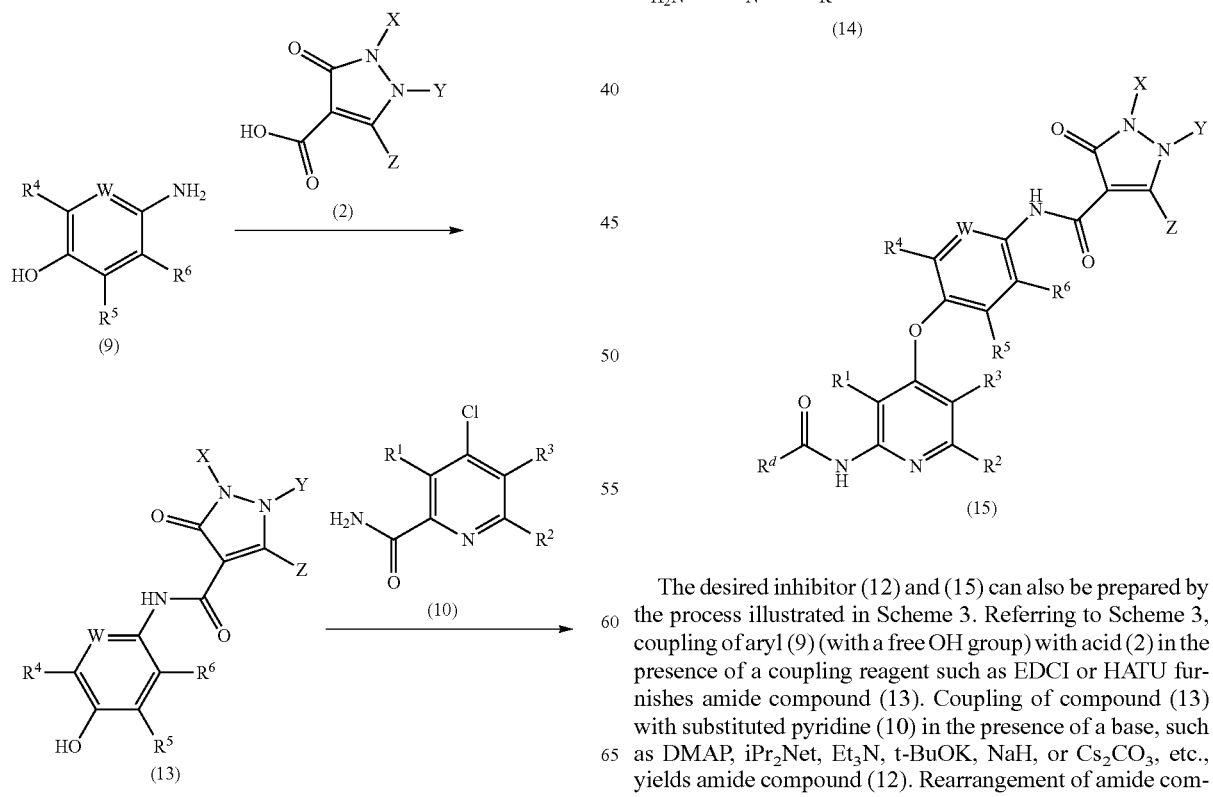

The desired inhibitor (12) and (15) can also be prepared by the process illustrated in Scheme 3. Referring to Scheme 3, coupling of aryl (9) (with a free OH group) with acid (2) in the presence of a coupling reagent such as EDCI or HATU furnishes amide compound (13). Coupling of compound (13) with substituted pyridine (10) in the presence of a base, such as DMAP, iPr$_2$Net, Et$_3$N, t-BuOK, NaH, or Cs$_2$CO$_3$, etc., yields amide compound (12). Rearrangement of amide compound (12) in the presence of an oxidant PhI(OAc)$_2$ or NaClO leads to aminopyridine (14), which can be further converted to urea (15) as the desired kinase inhibitor.

EXAMPLES

Example 1

3-chloro-4-(4-(1,5-dimethyl-3-oxo-2-phenyl-2,3-dihydro-1H-pyrazole-4-carboxamido)phenoxy)picolinamide

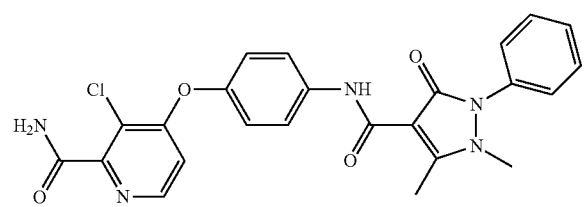 [SMILES: Cc1c(C(=O)Nc2ccc(Oc3ccnc(C(N)=O)c3Cl)cc2)c(=O)n(-c2ccccc2)n1C]

Step 1) N-(4-hydroxyphenyl)-1,5-dimethyl-3-oxo-2-phenyl-2,3-dihydro-1H-pyrazole-4-carboxamide To a mixture of 4-aminophenol (1.09 g, 10 mmol) and 1,5-dimethyl-3-oxo-2-phenyl-2,3-dihydro-1H-pyrazole-4-carboxylic acid (2.37 g, 10.2 mmol) in DCM (30 mL) was added EDCI (2.3 g, 12 mmol) and HOAT (0.27 g, 2 mmol). The mixture was stirred at 46° C. for 4 hours, then cooled to rt and diluted with EtOAc (10 mL) and water (10 mL). The mixture was stirred at rt for 1 hour, then filtered to give the title compound as a white solid (1.7 g, 52.5%).

MS (ESI, pos. ion) m/z: 324.1 [M+H]$^+$;

$^1$H NMR (400 MHz, DMSO-d$_6$): δ (ppm) 2.68 (s, 3H), 3.32 (s, 3H), 6.72 (d, J=8.8 Hz, 2H), 7.36-7.42 (m, 4H), 7.49 (t, J=7.4 Hz, 1H), 7.57 (t, J=7.6 Hz, 2H), 9.21 (s, 1H), 10.46 (s, 1H).

Step 2) 3,4-dichloropicolinamide

To a mixture of 2,2,6,6-tetramethylpiperidine (6.2 mL, 37.2 mmol) in diethylether (50 mL) was added n-BuLi in hexane (2.5M, 23 mL, 57.5 mmol) at 0° C. via syringe over 15 min. The mixture was stirred at 0° C. for 0.5 hour, then cooled to −78° C. A solution of 3,4-dichloropyridine (5.00 g, 33.8 mmol) in diethylether (20 mL) was added to the mixture via a syringe over 15 minutes. The reaction was stirred at −78° C. for 2 hours, then isocyanatotrimethylsilane (94% pure, 6.7 mL, 50.7 mmol) was added. The mixture was warmed up to rt and further stirred for 2 hours, quenched with acetic acid (6.76 g, 112.6 mmol) in 35 mL of water. The mixture was further stirred overnight. The titled product was precipitated overnight as a white solid, which was collected through filtration. More products were recovered from the filtrate. Thus, the filtrate was extracted with ethyl acetate (50 mL×3) and the combined organic phases were washed with brine (50 mL), dried over anhydrous Na$_2$SO$_4$, and concentrated in vacuo. The solid was combined and washed with 35 mL of Et$_2$O to give the title compound as a pale yellow solid (2.20 g, 34.0%).

MS (ESI, pos. ion) m/z: 191.1 [M+H]$^+$;

$^1$H NMR (400 MHz, DMSO-d$_6$): δ (ppm) 8.48 (d, J=5.2 Hz, 1H), 8.09 (br s, 1H), 7.82 (s, 1H), 7.81 (d, J=5.2 Hz, 1H).

Step 3) 3-chloro-4-(4-(1,5-dimethyl-3-oxo-2-phenyl-2,3-dihydro-1H-pyrazole-4-carboxamido)phenoxy)picolinamide To a mixture of N-(4-hydroxyphenyl)-1,5-dimethyl-3-oxo-2-phenyl-2,3-dihydro-1H-pyrazole-4-carboxamide (356 mg, 1.1 mmol) in DMSO (4 mL) in a microwave vial was added NaH (88 mg, 2.2 mmol, 60% dispersed in mineral oil) at rt. The reaction was stirred at rt for 30 minutes, then 3,4-dichloropicolinamide (191 mg, 1.0 mmol) was added. The mixture was microwaved at 160° C. for 2 hours, then cooled to rt, and diluted with water (10 mL). The resulted mixture was extracted with ethyl acetate (30 mL×3). The combined organic phases were washed with brine (30 mL×3), dried over anhydrous Na$_2$SO$_4$, and concentrated in vacuo. The residue was purified by a silica gel column chromatography (DCM/MeOH (v/v)=50/1) to give the title compound as a pale yellow solid (140 mg, 29%).

MS(ESI, pos. ion) m/z: 478.1 [M+H]$^+$;

$^1$H NMR (400 MHz, DMSO-d$_6$): δ (ppm) 2.71 (s, 3H), 3.35 (s, 3H), 6.82 (d, J=5.4 Hz, 1H), 7.19 (d, J=9.0 Hz, 2H), 7.44 (d, J=7.5 Hz, 2H), 7.53 (m, 1H), 7.59 (m, 2H), 7.74 (m, 3H), 8.02 (s, 1H), 8.33 (d, J=5.4 Hz, 1H), 10.84 (s, 1H).

Example 2

3-chloro-4-(4-(1,5-dimethyl-3-oxo-2-phenyl-2,3-dihydro-1H-pyrazole-4-carboxamido)-2-fluorophenoxy)picolinamide

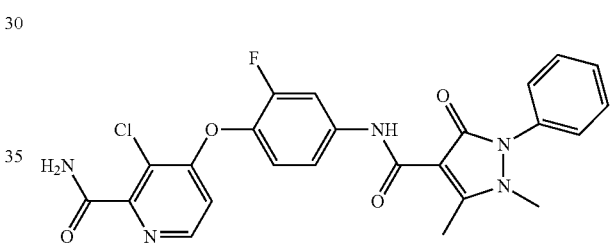

Step 1) 4-(4-amino-2-fluorophenoxy)-3-chloropicolinamide

To a solution of 4-amino-2-fluorophenol (254 mg, 2.0 mmol) in DMF (5 mL) was added t-BuOK (359 mg, 3.2 mmol). The mixture was stirred at rt for 30 minutes, then 3,4-dichloropicolinamide (420 mg, 2.2 mmol) was then added, and the mixture was microwaved at 120° C. for 2 hours. The mixture was cooled to rt, quenched with 25 mL of water. The resulted solution was extracted with EtOAc (30 mL×3) and the combined organic phases were washed with brine (30 mL×3), dried over Na$_2$SO$_4$ and concentrated in vacuo. The residue was purified by a silica gel column chromatography (EtOAc/PE (v/v)=2/1) to give the title compound as a pale yellow solid (306 mg, 54.4%).

MS (ESI, pos. ion) m/z: 282.1 [M+H]$^+$;

$^1$H NMR (400 MHz, DMSO-d$_6$): δ (ppm) 8.30 (d, J=5.6 Hz, 1H), 8.03 (s, 1H), 7.73 (s, 1H), 7.03 (t, J=9.0 Hz, 1H), 6.72 (dd, J=0.8 Hz, 5.6 Hz, 1H), 6.53 (dd, J=2.4 Hz, 13.2 Hz, 1H), 6.44 (dd, J=1.8 Hz, 8.7 Hz, 1H), 5.55 (s, 2H).

Step 2) 3-chloro-4-(4-(1,5-dimethyl-3-oxo-2-phenyl-2,3-dihydro-1H-pyrazole-4-carboxamido)-2-fluorophenoxy)picolinamide To a suspension of 4-(4-amino-2-fluorophenoxy)-3-chloropicolinamide (306 mg, 1.40 mmol) and 1,5-dimethyl-3- oxo-2-phenyl-2,3-dihydro-1H-pyrazole-4-carboxylic acid (390 mg, 1.68 mmol) in DCM (6 mL) was added EDCI (322 mg, 1.68 mmol) and HOAT (38 mg, 0.28 mmol). The mixture was stirred at 45° C. for 14.5 hours, then cooled to rt and quenched with 5 mL of water. The mixture was extracted with EtOAc (10 mL×3) and the combined organic phases were washed with brine (10 mL×3), dried over $Na_2SO_4$ and concentrated in vacuo. The residue was purified by a silica gel column chromatography (PE/EtOAc (v/v)=1/4) to give the title compound as a pale yellow solid (647 mg, 93.2%).

MS (ESI, pos. ion) m/z: 496.1 [M+H]$^+$;

$^1$H NMR (400 MHz, DMSO-d$_6$): δ (ppm) 10.98 (s, 1H), 8.33 (d, J=5.6 Hz, 1H), 8.06 (br s, 1H), 7.99 (dd, J=2.2 Hz, 13.2 Hz, 1H), 7.75 (br s, 1H), 7.60 (t, J=7.2 Hz, 2H), 7.52 (m, 1H), 7.45 (d, J=5.6 Hz, 2H), 7.35 (m, 2H), 6.84 (d, J=5.5 Hz, 1H), 3.37 (s, 3H), 2.71 (s, 3H).

Example 3

4-(4-(1,5-dimethyl-3-oxo-2-phenyl-2,3-dihydro-1H-pyrazole-4-carboxamido)-2,3-difluorophenoxy)picolinamide

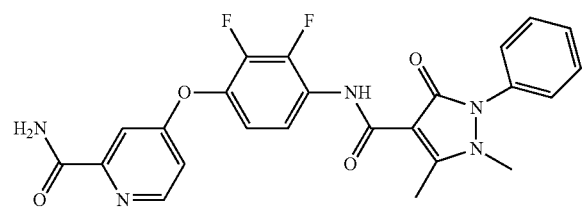 [SMILES: Cc1c(C(=O)Nc2ccc(Oc3ccnc(C(N)=O)c3)c(F)c2F)c(=O)n(-c2ccccc2)n1C]

Step 1) 1-(benzyloxy)-2,3-difluoro-4-nitrobenzene

To a solution of 2,4,5-trifluoronitrobenzene (5.00 g, 28.2 mmol) and benzyl alcohol (3.07 g, 28.4 mmol) in DMF (10 mL) was added $K_2CO_3$ (5.87 g, 42.5 mmol). The reaction was stirred at rt for 72 hours, then diluted with water (35 mL) and further stirred at 4° C. overnight. The precipitates were collected through filtration, washed with water (20 mL), and purified by a silica gel column chromatography (EtOAc/PE (v/v)=1/20) to give the title compound as a pale yellow solid (2.15 g, 28.7%).

$^1$H NMR (400 MHz, CDCl$_3$): δ (ppm) 7.90 (m, 1H), 7.43 (s, 2H), 7.42 (s, 2H), 7.39 (m, 1H), 6.86 (m, 1H), 5.27 (s, 2H).

Step 2) 4-amino-2,3-difluorophenol

To a suspension of 1-(benzyloxy)-2,3-difluoro-4-nitrobenzene (1.93 g, 0.73 mmol) in CH$_3$OH (45 mL) and THF (9 mL) was added Pd/C (333 mg, 6% Pd content, 53%~55% water content). The mixture was stirred at 32° C. for 13 hours under $H_2$ atmosphere. The mixture was filtered through a CELITE® pad, which was washed with 50 mL of EtOAc. The filtrate was concentrated in vacuo, washed with 30 mL of CH$_2$Cl$_2$ to give the title compound as a dark brown solid (0.89 g, 84%).

MS (ESI, pos. ion) m/z: 146.2 [M+H]$^+$;

$^1$H NMR (400 MHz, DMSO-d$_6$): δ (ppm) 6.49 (m, 1H), 6.38 (m, 1H), 4.71 (s, 2H).

Step 3) 4-(4-amino-2,3-difluorophenoxy)picolinamide

To a solution of 4-amino-2,3-difluorophenol (208 mg, 1.43 mmol) in DMF (4 mL) was added t-BuOK (257 mg, 2.29 mmol). The reaction was stirred at rt for 30 minutes, then 4-chloropicolinamide (249 mg, 1.59 mmol) was added. The mixture was microwaved at 120° C. for 3 hours, then cooled to rt and diluted with 25 mL of water. The resulted mixture was extracted with EtOAc (30 mL×3), and the combined organic phases were washed with brine (30 mL×3), dried over anhydrous Na$_2$SO$_4$, and concentrated in vacuo. The residue was purified by a silica gel column chromatography (PE/EtOAc (v/v)=1/2) to give the title compound as an orange solid (110 mg, 41.5%).

MS (ESI, pos. ion) m/z: 266.0 [M+H]$^+$, 283.2 [M+NH$_4$]$^+$;

$^1$H NMR (400 MHz, DMSO-d$_6$): δ (ppm) 8.42 (d, J=5.6 Hz, 1H), 7.84 (br s, 1H), 7.65 (d, J=2.5 Hz, 1H), 7.03 (m, 1H), 6.77 (m, 1H), 6.56 (m, 1H), 5.56 (br s, 1H), 3.08 (s, 2H).

Step 4) 4-(4-(1,5-dimethyl-3-oxo-2-phenyl-2,3-dihydro-1H-pyrazole-4-carboxamido)-2,3-difluorophenoxy)picolinamide To a suspension of 4-(4-amino-2,3-difluorophenoxy)picolinamide (180 mg, 0.68 mmol) and 1,5-dimethyl-3-oxo-2-phenyl-2,3-dihydro-1H-pyrazole-4-carboxylic acid (161 mg, 0.69 mmol) in DCM (4 mL) was added EDCI (157 mg, 0.82 mmol) and HOAT (19 mg, 0.14 mmol). The mixture was stirred at 45° C. for 12 hours, then more 1,5-dimethyl-3-oxo-2-phenyl-2,3-dihydro-1H-pyrazole-4-carboxylic acid (87 mg, 0.37 mmol) was added and the reaction was further stirred at 45° C. for 5 hours. The mixture was cooled to rt, quenched with 5 mL of water, and extracted with EtOAc (10 mL×3). The combined organic phases were washed with brine (10 mL×3), dried over Na$_2$SO$_4$, and concentrated in vacuo. The residue was purified by a silica gel column chromatography (EtOAc 100%) to give the title compound as an orange solid (108 mg, 33.2%).

MS (ESI, pos. ion) m/z: 480.1 [M+H]$^+$;

$^1$H NMR (400 MHz, DMSO-d$_6$): δ (ppm) 11.20 (s, 1H), 8.55 (d, J=5.7 Hz, 1H), 8.34 (m, 1H), 8.16 (br s, 1H), 7.76 (br s, 1H), 7.64 (m, 3H), 7.59 (d, J=7.8 Hz, 1H), 7.46 (m, 3H), 7.28 (m, 1H), 3.38 (s, 3H), 2.71 (s, 3H).

Example 4

4-(4-(1,5-dimethyl-3-oxo-2-phenyl-2,3-dihydro-1H-pyrazole-4-carboxamido)-2,5-difluorophenoxy)picolinamide

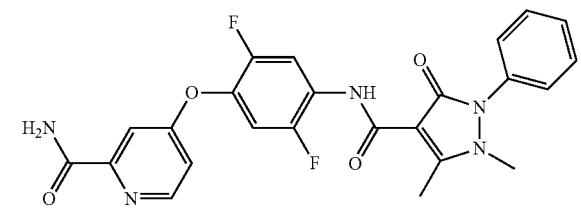 [SMILES: Cc1c(C(=O)Nc2cc(F)c(Oc3ccnc(C(N)=O)c3)cc2F)c(=O)n(-c2ccccc2)n1C]

Step 1) 1-(benzyloxy)-2,5-difluoro-4-nitrobenzene

To a solution of 2,4,5-trifluoronitrobenzene (5.4 g, 30.5 mmol) and benzyl alcohol (3.2 mL, 30.5 mmol) in DMF (20 mL) was added K₂CO₃ (6.33 g, 46.1 mmol). The reaction was stirred at room temperature for 72 hours. Water (60 mL) was added at 0° C. and the resulted mixture was further stirred at 4° C. for 24 hours. The solid was collected by filtration, washed with 30 mL of water, and dried in vacuo at 45° C. to provide the title compound as a pale yellow solid (6.0 g, 74%).

$^1$H NMR (400 MHz, CDCl₃): δ (ppm) 5.22 (s, 2H), 6.85-6.89 (m, 1H), 7.40-7.43 (m, 5H), 7.89-7.94 (m, 1H).

Step 2) 4-amino-2,5-difluorophenol

To a suspension of 1-(benzyloxy)-2,5-difluoro-4-nitrobenzene (1.06 g, 4 mmol) in CH₃OH (25 mL) and THF (5 mL) was added Pd/C (50% Pd content, 185 mg). The reaction was stirred at 32° C. under H₂ atmosphere for 10 hours. The mixture was filtered through a CELITE® pad and the filtrate was concentrated in vacuo. The residue was washed with DCM (15 mL) to give the title compound as a dark brown solid (500 mg, 86%).

MS (ESI, pos. ion) m/z: 146.2 [M+H]⁺;

$^1$H NMR (400 MHz, DMSO-d₆): δ (ppm) 4.68 (s, 2H), 6.53-6.65 (m, 2H), 9.06 (br, 1H).

Step 3) 4-(4-amino-2,5-difluorophenoxy)picolinamide

To a mixture of 4-amino-2,5-difluorophenol (100 mg, 0.64 mmol), and 4-chloropicolinamide (110 mg, 0.71 mmol) in DMF (2 mL) was added NaH (80 mg, 1.3 mmol, 60% dispersed in mineral oil). The reaction mixture was microwaved at 120° C. for 1.5 hours, then cooled to rt, diluted with water (20 mL), and extracted with EtOAc (30 mL×3). The combined organic phases were washed with brine (80 mL), dried over Na₂SO₄ and concentrated in vacuo. The residue was purified by flash column chromatography with (EtOAc/PE (v/v)=4/1) to afford the title compound as a brown solid (52 mg, 26%).

MS (ESI, pos. ion) m/z: 266.2 [M+H]⁺;

Step 4) 4-(4-(1,5-dimethyl-3-oxo-2-phenyl-2,3-dihydro-1H-pyrazole-4-carboxamido)-2,5-difluorophenoxy)picolinamide To a solution of 4-(4-amino-2,5-difluorophenoxy)picolinamide (200 mg, 0.76 mmol), and 1,5-dimethyl-3-oxo-2-phenyl-2,3-dihydro-1H-pyrazole-4-carboxylic acid (165 mg, 0.75 mmol) in DCM (10 mL) was added EDCI (175 mg, 0.93 mmol), and HOAT (26 mg, 0.15 mmol). The reaction was stirred at 45° C. for 16 hours, cooled to rt and diluted with EtOAc (20 mL). The solid was collected through filtration, dried at 45° C. in vacuo overnight to give the title compound as a white solid (230 mg, 63.7%).

MS (ESI, pos. ion) m/z: 480.1 [M+H]⁺;

$^1$H NMR (400 MHz, DMSO-d₆): δ (ppm) 11.24 (s, 1H), 8.53-8.57 (m, 2H), 8.15 (s, 1H), 7.75 (s, 1H), 7.53-7.59 (m, 4H), 7.44-7.45 (m, 3H), 7.24-7.25 (d, J=5.2 Hz, 1H), 3.43 (s, 3H), 2.70 (s, 3H).

Example 5

3-chloro-4-(4-(1,5-dimethyl-3-oxo-2-phenyl-2,3-dihydro-1H-pyrazole-4-carboxamido)-2,5-difluorophenoxy)picolinamide

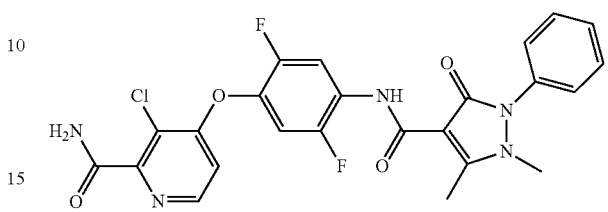

To a solution of N-(2,5-difluoro-4-hydroxyphenyl)-1,5-dimethyl-3-oxo-2-phenyl-2,3-dihydro-1H-pyrazole-4-carboxamide (395 mg, 1.1 mmol) in DMF (5.0 mL) was added t-BuOK (202 mg, 1.8 mmol) and the mixture was stirred at rt for 30 minutes. Then 3,4-dichloropicolinamide (190 mg, 1.0 mmol) was added and the mixture was microwaved at 120° C. for 2 hours, then cooled to rt, quenched with water (30 mL) and extracted with EtOAc (50 mL×3). The combined organic phases were washed with brine (50 mL×3), dried over anhydrous Na₂SO₄, and concentrated in vacuo. The residue was purified by a silica gel column chromatography (MeOH/DCM (v/v)=1/30) to give the title compound as a pale yellow solid (310 mg, 60%).

MS(ESI, pos. ion) m/z: 514.2 [M+H]⁺;

$^1$H NMR (400 MHz, DMSO-d₆): δ (ppm) 2.70 (s, 3H), 3.38 (s, 3H), 6.96 (d, J=5.5 Hz, 1H), 7.45 (d, J=7.0 Hz, 2H), 7.51-7.55 (m, 1H), 7.58-7.66 (m, 3H), 7.75 (s, 1H), 8.05 (s, 1H), 8.34 (d, J=5.5 Hz, 1H), 8.53-8.58 (m, 1H), 11.25 (s, 1H).

Example 6

4-(3-chloro-4-(1,5-dimethyl-3-oxo-2-phenyl-2,3-dihydro-1H-pyrazole-4-carboxamido)phenoxy)picolinamide

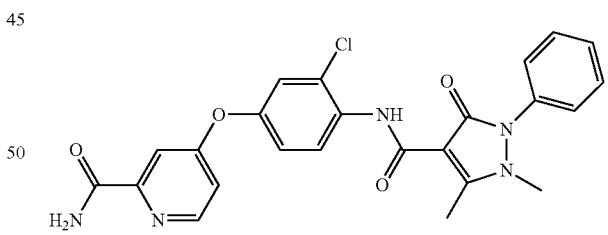

Step 1) 4-(4-amino-3-chlorophenoxy)picolinamide

To a mixture of 4-amino-2-chlorophenol hydrochloride (446 mg, 2.4 mmol) in DMSO (4 mL) was added NaH (280 mg, 7.0 mmol, 60% dispersed in mineral oil). The reaction was stirred at rt for 30 minutes, followed by the addition of 4-chloropicolinamide (345 mg, 2.2 mmol). The reaction was microwaved at 160° C. for 2 hours, then cooled to rt, and diluted with water (20 mL). The resulted mixture was extracted with ethyl acetate (20 mL×3) and the combined organic phases were washed with brine (20 mL), dried over anhydrous Na₂SO₄, and concentrated in vacuo. The residue was purified by a silica gel column chromatography (EtOAc/PE (v/v)=1/1) to give the title compound as an orange solid (170 mg, 29%).

MS (ESI, pos. ion) m/z: 264.1 [M+H]$^+$;

$^1$H NMR (400 MHz, DMSO-d$_6$): δ (ppm) 5.45 (s, 2H), 6.89 (d, J=8.7 Hz, 1H), 6.92 (m, 1H), 7.11 (m, 1H), 7.16 (d, J=2.6 Hz, 1H), 7.34 (d, J=2.6 Hz, 1H), 7.68 (s, 1H), 8.10 (s, 1H), 8.47 (d, J=5.6 Hz, 1H).

Step 2) 4-(3-chloro-4-(1,5-dimethyl-3-oxo-2-phenyl-2,3-dihydro-1H-pyrazole-4-carboxamido)phenoxy)picolinamide To a suspension of 4-(4-amino-3-chlorophenoxy)picolinamide (191 mg, 0.72 mmol) and 1,5-dimethyl-3-oxo-2-phenyl-2,3-dihydro-1H-pyrazole-4-carboxylic acid (168 mg, 0.72 mmol) in DCM (10 mL) was added EDCI (166 mg, 0.86 mmol) and HOAT (20 mg, 0.14 mmol). The reaction was stirred at 46° C. for 6 hours, followed by the addition of 1,5-dimethyl-3-oxo-2-phenyl-2,3-dihydro-1H-pyrazole-4-carboxylic acid (32 mg, 0.14 mmol) and EDCI (27 mg, 0.14 mmol). The mixture was further stirred at 46° C. for 13 hours, then cooled to rt and diluted with water (10 mL). The resulted mixture was extracted with ethyl acetate (10 mL×3), and the combined organic phases were washed with brine (10 mL), dried over anhydrous Na$_2$SO$_4$, and concentrated in vacuo. The residue was purified by a silica gel column chromatography (DCM/MeOH (v/v)=50/1) to give the title compound as a pale yellow solid (160 mg, 46.5%).

MS (ESI, pos. ion) m/z: 478.2 [M+H]$^+$;

$^1$H NMR (400 MHz, DMSO-d$_6$): δ (ppm) 2.71 (s, 3H), 3.37 (s, 3H), 7.19 (m, 1H), 7.23 (m, 1H), 7.43 (m, 3H), 7.50 (m, 2H), 7.60 (m, 2H), 7.72 (s, 1H), 8.13 (s, 1H), 8.52 (d, J=5.6 Hz, 1H), 8.63 (d, J=9.1 Hz, 1H), 11.19 (s, 1H).

Example 7

4-((6-(1,5-dimethyl-3-oxo-2-phenyl-2,3-dihydro-1H-pyrazole-4-carboxamido)pyridin-3-yl)oxy)picolinamide

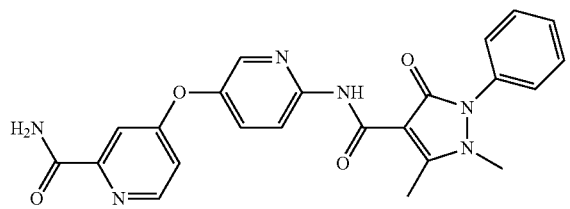 [SMILES: Cc1c(C(=O)Nc2ccc(Oc3ccnc(C(N)=O)c3)cn2)c(=O)n(-c2ccccc2)n1C]

Step 1) 4-((6-aminopyridin-3-yl)oxy)picolinamide

To a mixture of 6-aminopyridin-3-ol (220 mg, 2 mmol) and t-BuOK (225 mg, 2.16 mmol) in DMF (2.5 mL) was added 4-chloropicolinamide (315 mg, 2 mmol). The reaction was heated to 80° C. for 5 hours, then cooled to rt and diluted with EtOAc (50 mL) and H$_2$O (50 mL). The organic phase was concentrated in vacuo and the residue was purified by a silica gel column chromatography (DCM/CH$_3$OH (v/v)=30/1) to give the title compound as a brown solid (230 mg, 50%).

MS (ESI, pos. ion) m/z: 231.1 [M+H]$^+$;

$^1$H NMR (400 MHz, CDCl$_3$): δ (ppm) 6.09 (s, 2H), 6.53-6.56 (d, J=8.88 Hz, 1H), 7.12-7.14 (dd, J=2.64 Hz, 5.6 Hz, 1H), 7.31-7.34 (dd, J=2.92 Hz, 8.88 Hz, 1H), 7.35-7.36 (d, J=2.48 Hz, 1H), 7.70 (s, 1H), 7.83-7.84 (d, J=2.8 Hz, 1H), 8.11 (s, 1H), 8.46-8.49 (d, J=5.6 Hz, 1H).

Step 2) 4-((6-(1,5-dimethyl-3-oxo-2-phenyl-2,3-dihydro-1H-pyrazole-4-carboxamido)pyridin-3-yl)oxy)picolinamide To a suspension of 4-((6-aminopyridin-3-yl)oxy)picolinamide (230 mg, 1 mmol) and 1,5-dimethyl-3-oxo-2-phenyl-2,3-dihydro-1H-pyrazole-4-carboxylic acid (237 mg, 1.02 mmol) in DCM (5 mL) was added EDCI (230 mg, 1.2 mmol) and HOAT (27 mg, 0.2 mmol). The reaction was stirred at 45° C. for 28 hours, then cooled to rt and diluted with water (10 mL) and DCM (20 mL). The organic phase was concentrated in vacuo and the residue was purified by a silica gel column chromatography (DCM/CH$_3$OH (v/v)=40/1) to give the title compound as a light grey solid (111 mg, 25%).

MS (ESI, pos. ion) m/z: 445.1 [M+H]$^+$;

$^1$H NMR (400 MHz, DMSO-d$_6$): δ (ppm) 2.72 (s, 3H), 3.33 (s, 3H), 7.20-7.22 (dd, J=2.64 Hz, 5.64 Hz, 1H), 7.43-7.46 (m, 3H), 7.52-7.54 (m, 1H), 7.58-7.62 (m, 2H), 7.72 (s, 1H), 7.75-7.78 (dd, J=2.88 Hz, 8.96 Hz, 1H), 8.13 (s, 1H), 8.27-8.28 (d, J=2.68 Hz, 1H), 8.34-8.36 (d, J=9.08 Hz, 1H), 8.52-8.54 (d, J=5.6 Hz, 1H), 11.26 (s, 1H).

Example 8

N-(5-((2-(cyclopropanecarboxamido)pyridin-4-yl)oxy)pyridin-2-yl)-1,5-dimethyl-3-oxo-2-phenyl-2,3-dihydro-1H-pyrazole-4-carboxamide

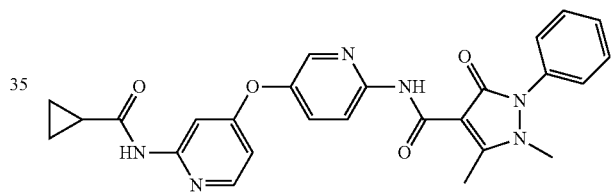

Step 1) N-(5-((2-aminopyridin-4-yl)oxy)pyridin-2-yl)-1,5-dimethyl-3-oxo-2-phenyl-2,3-dihydro-1H-pyrazole-4-carboxamide To a solution of 4-((6-(1,5-dimethyl-3-oxo-2-phenyl-2,3-dihydro-1H-pyrazole-4-carboxamido)pyridin-3-yl)oxy)picolinamide (111 mg, 0.25 mmol) in EtOAc (2 mL), CH$_3$CN (2 mL) and H$_2$O (1 mL) was added PhI(OAc)$_2$ (97 mg, 0.3 mmol). The reaction was stirred at 0° C. for 30 minutes, then warmed up to rt and further stirred for 12 hours. The mixture was concentrated in vacuo and the residue was purified by a silica gel column chromatography (DCM/CH$_3$OH (v/v)=40/1) to give the title compound as a light beige solid (85 mg, 81.7%).

MS (ESI, pos. ion) m/z: 417.2 [M+H]$^+$;

$^1$H NMR (400 MHz, DMSO-d$_6$): δ (ppm) 2.71 (s, 3H), 3.38 (s, 3H), 5.83 (s, 1H), 5.98 (s, 2H), 6.17 (s, 1H), 7.08-7.10 (m, 2H), 7.42-7.81 (m, 6H), 7.80-7.81 (d, J=5.8 Hz, 1H), 8.17 (s, 1H), 8.29-8.31 (d, J=8.56 Hz, 1H), 11.19 (s, 1H).

Step 2) N-(5-((2-(cyclopropanecarboxamido)pyridin-4-yl)oxy)pyridin-2-yl)-1,5-dimethyl-3-oxo-2-phenyl-2,3-dihydro-1H-pyrazole-4-carboxamide To a suspension of N-(5-((2-aminopyridin-4-yl)oxy)pyridin-2-yl)-1,5-dimethyl-3-oxo-2-phenyl-2,3-dihydro-1H- pyrazole-4-carboxamide (500 mg, 1.2 mmol) in DCM (5 mL) and triethylamine (1 mL) was added cyclopropanecarbonyl chloride (377 mg, 3.6 mmol) at 0° C. slowly. The mixture was warmed up to rt and stirred for 4.5 hours, then diluted with DCM (10 mL) and water (10 mL). The organic phase was separated and concentrated in vacuo. The residue was dissolved in MeOH (30 mL), and saturated solution of Na$_2$CO$_3$ (30 mL). The resulted mixture was stirred at rt for 2 hours, then filtered and the filtrate was concentrated in vacuo. The residue was purified by a silica gel column chromatography (DCM/MeOH (v/v)=50/1) to give the title compound as an off-white solid (350 mg, 60%).

MS (ESI, pos. ion) m/z: 485.3 [M+H]$^+$;
HPLC: 99.7%;
$^1$H NMR (600 MHz, CDCl$_3$): δ (ppm) 11.25 (s, 1H), 9.42 (s, 1H), 8.37 (t, J=12.0 Hz, 1H), 8.17 (t, J=7.5 Hz, 1H), 8.10 (t, J=9.8 Hz, 1H), 7.93 (d, J=2.1 Hz, 1H), 7.60-7.51 (m, 2H), 7.51-7.42 (m, 2H), 7.41-7.36 (m, 2H), 6.64 (dd, J=6.1 Hz, 2.4 Hz, 1H), 5.32 (s, 1H), 3.39 (s, 3H), 2.81 (s, 3H), 1.14-1.05 (m, 2H), 0.97-0.88 (m, 2H).

Example 9

3-chloro-4-((6-(1,5-dimethyl-3-oxo-2-phenyl-2,3-dihydro-1H-pyrazole-4-carboxamido)pyridin-3-yl)oxy)picolinamide

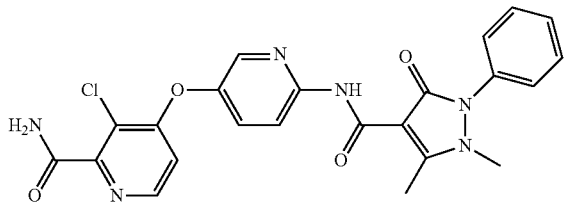 [SMILES: Cc1c(C(=O)Nc2ccc(Oc3ccnc(C(N)=O)c3Cl)cn2)c(=O)n(-c2ccccc2)n1C]

Step 1) N-(5-hydroxypyridin-2-yl)-1,5-dimethyl-3-oxo-2-phenyl-2,3-dihydro-1H-pyrazole-4-carboxamide To a suspension of 6-aminopyridin-3-ol (330 mg, 3 mmol) and 1,5-dimethyl-3-oxo-2-phenyl-2,3-dihydro-1H-pyrazole-4-carboxylic acid (710 mg, 306 mmol) in DMF (10 mL) was added EDCI (690 mg, 3.6 mmol) and HOAT (80 mg, 0.6 mmol). The reaction was stirred at 60° C. for 4 hours, then cooled to rt and diluted with water (100 mL) and EtOAc (2 mL). The mixture was cooled to 0° C. and stirred overnight. The resulted solid was collected through filtration to give title compound as a light brown solid (680 mg, 70%).

MS (ESI, pos. ion) m/z: 325.1 [M+H]$^+$;
$^1$H NMR (400 MHz, DMSO-d$_6$): δ (ppm) 2.50 (s, 3H), 3.33 (s, 3H), 7.18-7.20 (dd, J=2.3 Hz, 8.8 Hz, 1H), 7.40-7.42 (d, J=7.5 Hz, 2H), 7.48-7.52 (m, 1H), 7.56-7.60 (m, 2H), 7.81-7.82 (d, J=2.2 Hz, 1H), 7.95 (s, 1H), 8.04-8.06 (d, J=8.8 Hz, 1H), 9.61 (s, 1H), 10.85 (s, 1H).

Step 2) 3-chloro-4-((6-(1,5-dimethyl-3-oxo-2-phenyl-2,3-dihydro-1H-pyrazole-4-carboxamido)pyridin-3-yl)oxy)picolinamide To a mixture of 6-aminopyridin-3-ol (324 mg, 1 mmol) and t-BuOK (135 mg, 1.2 mmol) in DMF (2 mL) was added 3,4-dichloropicolinamide (191 mg, 1 mmol). The reaction was heated to 80° C. for 15 hours, then cooled to rt and diluted with EtOAc (1 mL) and H$_2$O (20 mL). The mixture was stirred overnight and the resulted solid was collected through filtration to give the title compound as a brown solid (290 mg, 60.5%).

MS (ESI, pos. ion) m/z: 479.2 [M+H]$^+$;
$^1$H NMR (400 MHz, CDCl$_3$): δ (ppm) 2.72 (s, 3H), 3.35 (s, 3H), 6.91-6.92 (d, J=5.5 Hz, 1H), 6.09 (s, 2H), 7.43-7.45 (m, 2H), 7.50-7.54 (m, 1H), 7.58-7.62 (m, 2H), 7.73-7.76 (m, 2H), 8.03 (s, 1H), 8.26-8.27 (d, J=2.7 Hz, 1H), 8.33-8.36 (m, 2H), 11.26 (s, 1H).

Example 10

4-(4-(1,5-dimethyl-3-oxo-2-phenyl-2,3-dihydro-1H-pyrazole-4-carboxamido)-2-fluorophenoxy)picolinamide

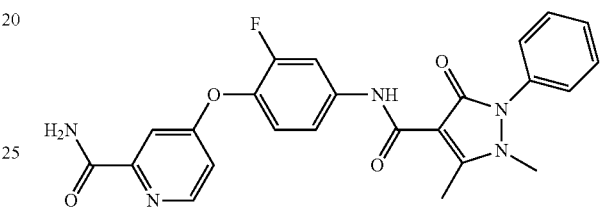

Step 1) N-(3-fluoro-4-hydroxyphenyl)-1,5-dimethyl-3-oxo-2-phenyl-2,3-dihydro-1H-pyrazole-4-carboxamide To a suspension of 4-amino-2-fluorophenol (2.54 g, 20 mmol) and 1,5-dimethyl-3-oxo-2-phenyl-2,3-dihydro-1H-pyrazole-4-carboxylic acid (4.74 g, 20.4 mmol) in DCM (60 mL) were added EDCI (4.6 g, 24 mmol) and HOAT (0.54 g, 4 mmol). The reaction was stirred at 45° C. for 12 hours, then cool to rt, quenched with H$_2$O (10 mL), and stirred for another 4 hours. The solid was obtained by filtration and washed with DCM (20 mL×3), then dried at 60° C. in vacuo for 12 hours to give the title compound as a pale yellow solid (6.37 g, 93.4%).

MS (ESI, pos. ion) m/z: 342.1 [M+H]$^+$;
$^1$H NMR (400 MHz, DMSO-d$_6$): δ (ppm) 10.59 (s, 1H), 9.58 (s, 1H), 7.64 (dd, J=2.4 Hz, 13.5 Hz, 1H), 7.60 (m, 2H), 7.50 (m, 1H), 7.42 (m, 2H), 6.97 (m, 1H), 6.88 (dd, J=9.6 Hz, 8.8 Hz, 1H), 3.34 (s, 3H), 2.70 (s, 3H).

Step 2) 4-(4-(1,5-dimethyl-3-oxo-2-phenyl-2,3-dihydro-1H-pyrazole-4-carboxamido)-2-fluorophenoxy)picolinamide To a suspension of N-(3-fluoro-4-hydroxyphenyl)-1,5-dimethyl-3-oxo-2-phenyl-2,3-dihydro-1H-pyrazole-4-carboxamide (2.2 g, 6.4 mmol), 4-chloropicolinamide (1 g, 6.39 mmol) in DMSO (12 mL) was added NaH (615 mg, 12.3 mmol, 50% dispersed in mineral oil). The reaction was stirred at 160° C. for 20 h, then cooled to rt, and diluted with H$_2$O (70 mL). The mixture was extracted with EtOAc (100 mL×3). The combined organic phases were washed with brine (100 mL), dried over Na$_2$SO$_4$ and concentrated in vacuo. The residue was purified by a silica gel column chromatography (PE/EtOAc (v/v)=1/4) to give the title compound as a white solid (0.85 g, 29%).

MS (ESI, pos. ion) m/z: 462.1 [M+H]$^+$;
$^1$H NMR (400 MHz, CDCl$_3$): δ (ppm) 10.87 (s, 1H), 8.40-8.41 (d, J=5.6 Hz, 1H), 7.88-7.92 (dd, J=2.4 Hz, 12.6 Hz, 1H), 7.82-7.83 (d, J=3.9 Hz, 1H), 7.71-7.71 (d, J=2.5 Hz, 1H), 7.54-7.58 (m, 2H), 7.46-7.49 (m, 1H), 7.35-7.37 (d, J=8.6 Hz, 2H), 7.07-7.11 (m, 1H), 6.96-6.98 (dd, J=2.5 Hz, 5.6 Hz, 1H), 5.56 (s, 1H), 3.37 (s, 3H), 2.79 (s, 3H).

Example 11

N-(4-((2-(cyclopropanecarboxamido)pyridin-4-yl)oxy)-3-fluorophenyl)-1,5-dimethyl-3-oxo-2-phenyl-2,3-dihydro-1H-pyrazole-4-carboxamide

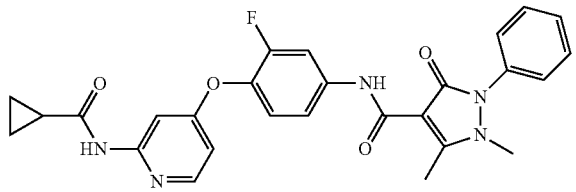 [SMILES: Cc1c(C(=O)Nc2ccc(Oc3ccnc(NC(=O)C4CC4)c3)c(F)c2)c(=O)n(-c2ccccc2)n1C]

Step 1) N-(4-((2-aminopyridin-4-yl)oxy)-3-fluorophenyl)-1,5-dimethyl-3-oxo-2-phenyl-2,3-dihydro-1H-pyrazole-4-carboxamide A solution of 4-(4-(1,5-dimethyl-3-oxo-2-phenyl-2,3-dihydro-1H-pyrazole-4-carboxamido)-2-fluorophenoxy)picolinamide (0.4 g, 0.86 mmol) and PhI(OAc)$_2$ (419 mg, 1.5 mmol) in a mixture of EtOAc (8 mL), MeCN (8 mL) and H$_2$O (4 mL) was cooled to 0° C. and stirred for 30 minutes. The reaction was then allowed to warm to rt, and stirred for another 8 h. The mixture was diluted with NaHCO$_3$ (aq., 60 mL) and extracted with EtOAc (100 mL×3). The combined organic phases were washed with brine, dried over Na$_2$SO$_4$ and concentrated in vacuo. The residue was purified by a silica gel column chromatography (DCM/MeOH (v/v)=10/1) to give the title compound as a white solid (0.21 g, 56%).

MS (ESI, pos. ion) m/z: 434.2 [M+H]$^+$;

$^1$H NMR (400 MHz, CDCl$_3$): δ (ppm) 10.83 (s, 1H), 7.91-7.92 (d, J=5.9 Hz, 1H), 7.83-7.86 (dd, J=2.4 Hz, 10.1 Hz, 1H), 7.56-7.58 (m, 2H), 7.46-7.52 (d, J=5.9 Hz, 2H), 7.35-7.37 (d, J=8.6 Hz, 2H), 7.04-7.09 (m, 1H), 6.29-6.31 (m, 1H), 5.92-5.93 (d, J=2.1 Hz, 1H), 4.45 (s, 2H), 3.37 (s, 3H), 2.79 (s, 3H).

Step 2) N-(4-((2-(cyclopropanecarboxamido)pyridin-4-yl)oxy)-3-fluorophenyl)-1,5-dimethyl-3-oxo-2-phenyl-2,3-dihydro-1H-pyrazole-4-carboxamide To a solution of N-(4-((2-aminopyridin-4-yl)oxy)-3-fluorophenyl)-1,5-dimethyl-3-oxo-2-phenyl-2,3-dihydro-1H-pyrazole-4-carboxamide (217 mg, 0.5 mmol) in DCM (5 mL) was added Et$_3$N (253 mg, 2.5 mmol) and cyclopropanecarbonyl chloride (125 mg, 1.2 mmol) at 0° C. The reaction mixture was stirred at rt for 4 hours, quenched with H$_2$O (10 mL) and extracted with DCM (50 mL×3). The combined organic phases were washed with brine (50 mL×3), dried over anhydrous Na$_2$SO$_4$, and concentrated in vacuo. The residue was dissolved in CH$_3$OH (20 mL), and a solution of Na$_2$CO$_3$ (106 mg, 1.0 mmol) in H$_2$O (1 mL). The resulted mixture was stirred at rt for 1 hour and concentrated in vacuo. The residue was purified by a silica gel column chromatography (pure DCM) to give the title compound as a beige solid (158 mg, 63.2%).

MS (ESI, pos. ion) m/z: 502.3 [M+H]$^+$;

$^1$H NMR (600 MHz, CDCl$_3$): δ (ppm) 10.93 (s, 1H), 10.73 (s, 1H), 8.03 (d, J=6.0 Hz, 2H), 7.96 (dd, J=12.5 Hz, 2.3 Hz, 1H), 7.59 (t, J=7.8 Hz, 2H), 7.51 (d, J=7.5 Hz, 1H), 7.38 (d, J=7.4 Hz, 2H), 7.30 (d, J=9.2 Hz, 1H), 7.12 (t, J=8.7 Hz, 1H), 6.74 (dd, J=6.3 Hz, 1.9 Hz, 1H), 3.40 (s, 3H), 2.81 (s, 3H), 1.79 (m, 1H), 1.12 (m, 2H), 0.97 (m, 2H).

Example 12

4-(5-chloro-4-(1,5-dimethyl-3-oxo-2-phenyl-2,3-dihydro-1H-pyrazole-4-carboxamido)-2-fluorophenoxy)picolinamide

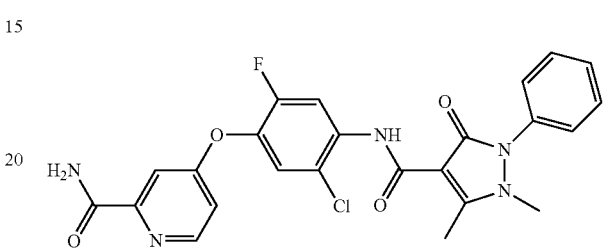

Step 1) 1-chloro-4,5-difluoro-2-nitrobenzene

To a flask was added 4-chloro-1,2-difluorobenzene (8.97 g, 60.4 mmol), followed by adding 98% con. H$_2$SO$_4$ (16.1 mL, 302 mmol) and 65% con. HNO$_3$ (5.0 mL, 66.4 mmol) at 0° C. The mixture was stirred at rt for 5 hours, then poured into ice water (500 mL). The resulted mixture was extracted with ethyl acetate (200 mL×3). The combined organic phase were washed with saturated aqueous NaHCO$_3$ solution (200 mL×2) and brine (200 mL), dried over anhydrous Na$_2$SO$_4$, and concentrated in vacuo to give the title compound as yellow liquid (11.31 g, 96.7%).

$^1$H NMR (400 MHz, CDCl$_3$): δ (ppm) 7.41-7.45 (m, 1H), 7.86-7.90 (m, 1H).

Step 2) potassium 5-chloro-2-fluoro-4-nitrophenolate

A mixture of 1-chloro-4,5-difluoro-2-nitrobenzene (5.12 g, 26.5 mmol) and 15% aqueous KOH (19.9 g) solution was stirred at reflux for 3 hours, then cooled to rt, and filtered to give the title compound as a yellow crystalloid (5.67 g, 93.3%).

$^1$H NMR (400 MHz, DMSO-d$_6$): δ (ppm) 6.20 (d, J=13.2 Hz, 1H), 7.70 (d, J=8.6 Hz, 1H).

Step 3) 4-amino-5-chloro-2-fluorophenol

To a solution of potassium 5-chloro-2-fluoro-4-nitrophenolate (1.0 g, 4.35 mmol, Yuxiang) in 95% EtOH (22 mL) and H$_2$O (8 mL) was added Fe (0.97 g, 17.4 mmol) and NH$_4$Cl (1.86 g, 34.8 mmol). The mixture was stirred at rt for 10 hours, then diluted with methanol (100 mL) and ethyl acetate (100 mL). Filtered and the filtrate was concentrated in vacuo. The residue was dissolved in water (50 mL) and ethyl acetate (50 mL). The organic phase was separated and the water phase was extracted with ethyl acetate (50 mL×2). The combined organic layers were washed with brine (50 mL×3), dried over anhydrous Na$_2$SO$_4$, and concentrated in vacuo to give the title compound as a pale solid (0.6 g, 85.3%).

$^1$H NMR (400 MHz, DMSO-d$_6$): δ (ppm) 4.90 (s, 2H), 6.60 (d, J=12.9 Hz, 1H), 6.79 (d, J=8.8 Hz, 1H), 9.11 (s, 1H).

Step 4) N-(2-chloro-5-fluoro-4-hydroxyphenyl)-1,5-dimethyl-3-oxo-2-phenyl-2,3-dihydro-1H-pyrazole-4-carboxamide To a suspension of 4-amino-5-chloro-2-fluorophenol (0.97 g, 6 mmol) and 1,5-dimethyl-3-oxo-2-phenyl-2,3-dihydro-1H-pyrazole-4-carboxylic acid (1.42 g, 6.12 mmol) in DMF (20 mL) was added EDCI (0.38 mg, 7.2 mmol) and HOAT (0.16 g, 1.2 mmol). The mixture was allowed to warm up to 80° C. and stirred for 24 hours. Then H$_2$O (200 mL) and EtOAc (2 mL) was added. The resulted mixture was stirred at 0° C. for 2 hours, then filtered to give the title compound as a light brown solid (1.2 g, 53.2%).

MS (ESI, pos. ion) m/z: 376.1 [M+H]$^+$;
$^1$H NMR (400 MHz, DMSO-d$_6$): δ (ppm) 2.68 (s, 3H), 3.34 (s, 3H), 7.02-7.04 (d, J=8.8 Hz, 1H), 7.41-7.43 (m, 2H), 7.48-7.52 (m, 1H), 7.56-7.60 (m, 2H), 829-8.33 (d, J=13.8 Hz, 1H), 10.08 (s, 1H), 10.95 (s, 1H).

Step 5) 4-(5-chloro-4-(1,5-dimethyl-3-oxo-2-phenyl-2,3-dihydro-1H-pyrazole-4-carboxamido)-2-fluorophenoxy)picolinamide To a suspension of N-(2-chloro-5-fluoro-4-hydroxyphenyl)-1,5-dimethyl-3-oxo-2-phenyl-2,3-dihydro-1H-pyrazole-4-carboxamide (751.6 mg, 2 mmol) and t-BuOK (224.4 mg, 2 mmol) in DMF (4 mL) and was added 4-chloropicolinamide (313.2 mg, 2 mmol). The reaction was warmed up to 120° C. and stirred for 15 hours. After the mixture cooling to rt, H$_2$O (40 mL) was added and the resulted mixture was stirred at rt overnight. Filtered and the filter cake was purified by a silica gel column chromatography (DCM/CH$_3$OH (v/v) =50/1) to give the title compound as a light yellow solid (290 mg, 60.5%).

MS (ESI, pos. ion) m/z: 496.2 [M+H]$^+$;
$^1$H NMR (400 MHz, DMSO-d$_6$): δ (ppm) 11.37 (s, 1H), 8.69-8.66 (d, J=13.4 Hz, 1H), 8.55-8.54 (d, J=5.6 Hz, 1H), 8.15 (s, 1H), 7.78-7.75 (m, 2H), 7.62-7.58 (m, 2H), 7.55-7.51 (m, 1H), 7.46-7.43 (m, 3H), 7.26-7.24 (dd, J=5.6 Hz, 2.6 Hz, 1H), 3.38 (s, 3H), 2.72 (s, 3H).

Example 13

4-(2-chloro-4-(1,5-dimethyl-3-oxo-2-phenyl-2,3-dihydro-1H-pyrazole-4-carboxamido)phenoxy)picolinamide

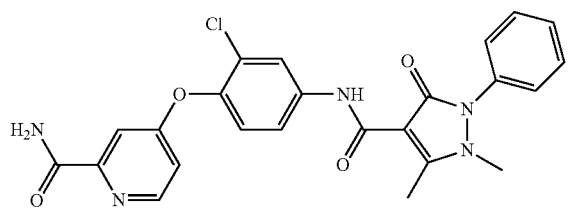 [SMILES: Cc1c(C(=O)Nc2ccc(Oc3ccnc(C(N)=O)c3)c(Cl)c2)c(=O)n(-c2ccccc2)n1C]

Step 1) N-(3-chloro-4-hydroxyphenyl)-1,5-dimethyl-3-oxo-2-phenyl-2,3-dihydro-1H-pyrazole-4-carboxamide To a suspension of 4-amino-2-chlorophenol (4.0 g, 28.00 mmol) and 1,5-dimethyl-3-oxo-2-phenyl-2,3-dihydro-1H-pyrazole-4-carboxylic acid (7.4 g, 30.11 mmol) in DCM (70 mL) were added EDCI (6.65 g, 30.11 mmol) and HOAT (0.76 g, 5.68 mmol). The mixture was stirred at 45° C. for 20 hours, then cooled to rt and filtered. The filter cake was washed with DCM (20 mL×3), and dried at 50° C. in a vacuum oven overnight to give the title product as a gray solid (7.1 g, 72.1%).

MS (ESI, pos. ion) m/z: 358.1 [M+H]$^+$;
$^1$H NMR (400 MHz, DMSO-d$_6$): δ (ppm) 10.56 (s, 1H), 9.92 (s, 1H), 7.59 (m, 2H), 7.50 (m, 1H), 7.42 (m, 2H), 7.83 (dd, J=2.6 Hz, 8.7 Hz, 1H), 6.90 (d, J=8.7 Hz, 1H), 6.88 (dd, J=9.6 Hz, 8.8 Hz, 1H), 3.33 (s, 3H), 2.68 (s, 3H).

Step 2) 4-(2-chloro-4-(1,5-dimethyl-3-oxo-2-phenyl-2,3-dihydro-1H-pyrazole-4-carboxamido)phenoxy)picolinamide To a suspension of N-(3-chloro-4-hydroxyphenyl)-1,5-dimethyl-3-oxo-2-phenyl-2,3-dihydro-1H-pyrazole-4-carboxamide (1.074 g, 3.0 mmol) in DMF (12 mL) was added t-BuOK (539 mg, 4.8 mmol). The mixture was stirred at rt for 30 minutes, then 4-chloropicolinamide (517 mg, 3.3 mmol) was added. The mixture was stirred at 120° C. for 36 hours, then cooled to rt, quenched with 50 mL of water and extracted with EtOAc (50 mL×3). The combined organic phases were washed with brine (50 mL×3), dried over anhydrous Na$_2$SO$_4$, and concentrated in vacuo. The residue was purified by a silica gel column chromatography (EtOAc/PE (v/v)=3/1) to give the title compound as a white solid (580 mg, 40.4%).

MS (ESI, pos. ion) m/z: 478.0 [M+H]$^+$;
$^1$H NMR (400 MHz, DMSO-d$_6$): δ (ppm) 10.95 (s, 1H), 8.53 (d, J=5.6 Hz, 1H), 8.16 (d, J=2.4 Hz, 1H), 8.13 (br s, 1H), 7.72 (br s, 1H), 7.60 (m, 2H), 7.51 (m, 2H), 7.44 (d, J=7.3 Hz, 2H), 7.38 (d, J=8.8 Hz, 1H), 7.32 (d, J=2.6 Hz, 1H), 7.17 (dd, J=2.6 Hz, 5.6 Hz, 1H), 3.16 (d, J=5.2 Hz, 3H), 2.70 (s, 3H).

Example 14

4-(4-(1,5-dimethyl-3-oxo-2-phenyl-2,3-dihydro-1H-pyrazole-4-carboxamido)-3-fluorophenoxy)picolinamide

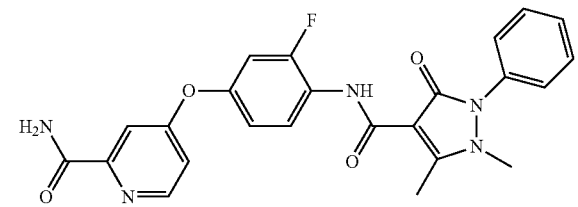 [SMILES: Cc1c(C(=O)Nc2ccc(Oc3ccnc(C(N)=O)c3)cc2F)c(=O)n(-c2ccccc2)n1C]

Step 1) 4-amino-3-fluorophenol

A suspension of 3-fluoro-4-nitrophenol (2.0 g, 12.73 mmol), 10% Pd/C (0.4 g) and HCOOK (8.75 g, 101.85 mmol) in THF/H$_2$O (70 mL/20 mL) was stirred at 50° C. for 5 hours, then cooled to rt, and filtered through CELITE®. The filtrate was diluted with water (30 mL) and extracted with THF (50 mL). The organic layer was dried over Na$_2$SO$_4$ and concentrated in vacuo. The residue was diluted with water (50 mL) and extracted with DCM (50 mL). The organic layer was dried over anhydrous Na$_2$SO$_4$ and concentrated in vacuo to give the title compound as a brown solid (1.17 g, 72.3%).

MS (ESI, pos, ion) m/z: 128.1 [M+H]$^+$, Rt=0.204 min.

Step 2) N-(2-fluoro-4-hydroxyphenyl)-1,5-dimethyl-3-oxo-2-phenyl-2,3-dihydro-1H-pyrazole-4-carboxamide To a suspension of 4-amino-3-fluorophenol (1.0 g, 7.87 mmol) and 1,5-dimethyl-3-oxo-2-phenyl-2,3-dihydro-1H-pyrazole-4-carboxylic acid (2.19 g, 9.44 mmol) in CH$_2$Cl$_2$ (20 mL) were added EDCI (3.02 g, 15.7 mmol) and HOAT (0.21 g, 1.57 mmol). The reaction mixture was refluxed for 20 hours, and then cooled to rt. Water (10 mL) was added and the mixture stirred at rt overnight, then filtered and the filter cake was washed with water (5 mL), followed by purifying by a silica gel column chromatography (CH$_2$Cl$_2$/MeOH (v/v)=70/1) to give the title compound as a beige white solid (1.25 g, 46.6%).

MS (ESI, pos, ion) m/z: 342.1 [M+H]$^+$, Rt=2.712 min.

Step 3) 4-(4-(1,5-dimethyl-3-oxo-2-phenyl-2,3-dihydro-1H-pyrazole-4-carboxamido)-3-fluorophenoxy)picolinamide To a mixture of N-(2-fluoro-4-hydroxyphenyl)-1,5-dimethyl-3-oxo-2-phenyl-2,3-dihydro-1H-pyrazole-4-carboxamide (300 mg, 0.879 mmol) and t-BuOK (118 mg, 1.05 mmol) was added DMF (2.5 mL). The resulted mixture was stirred at rt for 30 minutes, then 4-chloropicolinamide (165 mg, 1.05 mmol) was added. The mixture was heated at 120° C. for 5 hours, then cooled to rt, and H$_2$O (50 mL) and EtOAc (2 mL) was added. The resulted mixture was stirred at rt overnight. Filtered and the precipitation was washed with water (5 mL) to give the title compound as a dark brown solid (370 mg, 91.2%).

MS (ESI, pos, ion) m/z: 462.2 [M+H]$^+$, Rt=3.012 min.

Example 15

3-chloro-4-(4-(1,5-dimethyl-3-oxo-2-phenyl-2,3-dihydro-1H-pyrazole-4-carboxamido)-3-fluorophenoxy)picolinamide

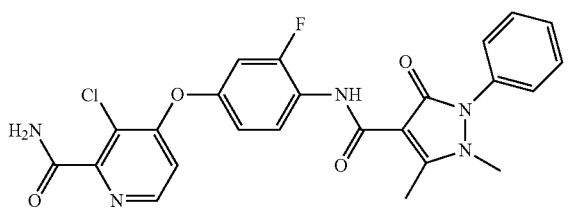 [SMILES: Cc1c(C(=O)Nc2ccc(Oc3ccnc(C(N)=O)c3Cl)cc2F)c(=O)n(-c2ccccc2)n1C]

A mixture of N-(2-fluoro-4-hydroxyphenyl)-1,5-dimethyl-3-oxo-2-phenyl-2,3-dihydro-1H-pyrazole-4-carboxamide (300 mg, 0.879 mmol) and t-BuOK (118 mg, 1.05 mmol) in DMF (3 mL) was stirred at rt for 30 minutes, then 3,4-dichloropicolinamide (201 mg, 1.05 mmol) was added. The reaction mixture was heated to 120° C. and stirred for 12 hours. EtOAc (1 mL) and H$_2$O (20 mL) were added, and the resulted mixture was stirred at rt overnight. Filtered to give the title compound as a brown solid (379 mg, 87.0%).

MS (ESI, pos, ion) m/z: 496.0 [M+H]$^+$, Rt=2.642 min.

Example 16

N-(4-((2-(cyclopropanecarboxamido)pyridin-4-yl)oxy)phenyl)-1,5-dimethyl-3-oxo-2-phenyl-2,3-dihydro-1H-pyrazole-4-carboxamide

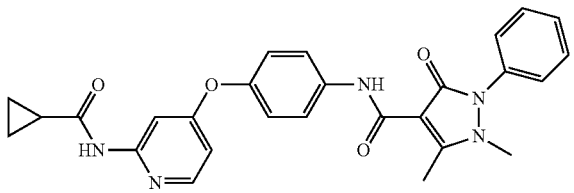 [SMILES: Cc1c(C(=O)Nc2ccc(Oc3ccnc(NC(=O)C4CC4)c3)cc2)c(=O)n(-c2ccccc2)n1C]

Step 1) 4-aminophenol

To a mixture of 4-nitrophenol (7 g, 50.3 mmol) and HCOOK (1.8 g, 21.48 mmol) in THF (210 mL) and H$_2$O (70 mL) was added Pd/C (110 mg, 10% Pd content, 53%~55% water content). The reaction was stirred at 50° C. for 24 hours, and then concentrated in vacuo. The residue was diluted with DCM (100 mL) and filtered through a CELITE® pad. The filtrate was concentrated in vacuo to give the title compound as a pale orange solid (3.28 g, 60%).

MS (ESI, pos. ion) m/z: 110.1 [M+H]$^+$.

Step 2) 4-(4-aminophenoxy)pyridin-2-amine

To a mixture of 4-aminophenol (218 mg, 2 mmol) and 4-chloropyridin-2-amine (256 mg, 2 mmol) in DMSO (2.5 mL) was added NaOCH$_3$ (216 mg, 4 mmol). The reaction was microwaved at 180° C. for 40 minutes, then cooled down to rt and quenched with water (10 mL). The mixture was extracted with EtOAc (10 mL×3). The combined organic phases were dried over anhydrous Na$_2$SO$_4$ and concentrated in vacuo. The residue was purified by a silica gel column chromatography (DCM/CH$_3$OH (v/v)=30/1) to give the title compound as a brown solid (103 mg, 26%).

MS (ESI, pos. ion) m/z: 202.2 [M+H]$^+$;
$^1$H NMR (400 MHz, CDCl$_3$): δ (ppm) 3.65 (s, 2H), 4.37 (s, 1H), 5.89-5.90 (d, J=2.04 Hz, 1H), 6.25-6.27 (dd, J=2.08 Hz, 5.88 Hz, 1H), 6.68-6.71 (m, 2H), 6.86-6.89 (m, 2H), 7.88-7.89 (d, J=5.88 Hz, 1H).

Step 3) N-(4-((2-aminopyridin-4-yl)oxy)phenyl)-1,5-dimethyl-3-oxo-2-phenyl-2,3-dihydro-1H-pyrazole-4-carboxamide To a mixture of 4-(4-aminophenoxy)pyridin-2-amine (101 mg, 0.5 mmol) and 1,5-dimethyl-3-oxo-2-phenyl-2,3-dihydro-1H-pyrazole-4-carboxylic acid (118 mg, 0.51 mmol) in DCM (5 mL) was added EDCI (115 mg, 0.6 mmol) and HOAT (13.6 mg, 0.1 mmol). The reaction was stirred at 45° C. for 3 hours, and then quenched with water (20 mL). The organic phase was separated and concentrated in vacuo. The residue was purified by a silica gel column chromatography (DCM/CH$_3$OH (v/v)=20/1) to give the title compound as a light grey solid (110 mg, 49.2%).

MS (ESI, pos. ion) m/z: 416.4 [M+H]$^+$;
$^1$H NMR (400 MHz, DMSO-d$_6$): δ (ppm) 2.71 (s, 3H), 3.36 (s, 3H), 5.80-5.81 (d, J=2.16 Hz, 1H), 5.92 (s, 2H), 6.12-6.14 (dd, J=2.24 Hz, 5.8 Hz, 1H), 7.08-7.10 (m, 2H), 7.42-7.45 (m, 2H), 7.51-7.53 (m, 1H), 7.57-7.61 (m, 2H), 7.65-7.67 (m, 2H), 7.77-7.79 (d, J=5.8 Hz, 1H).

Step 4) N-(4-((2-(cyclopropanecarboxamido)pyridin-4-yl)oxy)phenyl)-1,5-dimethyl-3-oxo-2-phenyl-2,3-dihydro-1H-pyrazole-4-carboxamide To a solution of N-(4-((2-aminopyridin-4-yl)oxy)phenyl)-1,5-dimethyl-3-oxo-2-phenyl-2,3-dihydro-1H-pyrazole-4-carboxamide (200 mg, 0.48 mmol) in DCM (5 mL) was added triethylamine (1 mL), followed by adding cyclopropanecarbonyl chloride (104.5 mg, 0.96 mmol) at 0° C. The reaction mixture was warmed to rt and stirred for 3 hours, then quenched with water (10 mL). The separated organic layer was added saturated aq. Na$_2$CO$_3$ (10 mL) and EtOH (30 mL). The mixture was stirred at rt for 30 minutes and concentrated in vacuo. The residue was purified by a silica gel column chromatography (DCM/MeOH (v/v)=80/1) to give the title compound as a white solid (130 mg, 56%).

HPLC: 99.5%;

MS (ESI, pos. ion) m/z: 484.3 [M+H]$^+$;

$^1$H NMR (600 MHz, CDCl$_3$): δ (ppm) 10.77 (s, 1H), 9.45 (s, 1H), 8.05 (d, J=5.8 Hz, 1H), 7.90 (s, 1H), 7.74 (d, J=8.9 Hz, 2H), 7.57 (t, J=7.8 Hz, 2H), 7.48 (t, J=7.5 Hz, 1H), 7.38 (d, J=7.4 Hz, 2H), 7.05 (d, J=8.9 Hz, 2H), 6.62 (dd, J=6.0 Hz, 2.0 Hz, 1H), 3.37 (s, 3H), 2.81 (s, 3H), 1.65 (td, J=7.7 Hz, 4.0 Hz, 1H), 1.26 (d, J=12.8 Hz, 2H), 1.10 (dt, J=7.9 Hz, 4.0 Hz, 2H).

Example 17

N-(5-((2-(3-(2-hydroxyethyl)ureido)pyridin-4-yl)oxy)pyridin-2-yl)-1,5-dimethyl-3-oxo-2-phenyl-2,3-dihydro-1H-pyrazole-4-carboxamide

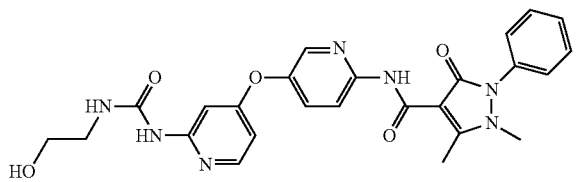 [SMILES: Cc1c(C(=O)Nc2ccc(Oc3ccnc(NC(=O)NCCO)c3)cn2)c(=O)n(-c2ccccc2)n1C]

Step 1) 4-chloropicolinamide

To a solution of 4-chloropicolinic acid (100 mg, 0.64 mmol) in DCM (10 mL) was added one drop DMF and SOCl$_2$ (0.14 mL, 1.92 mmol). The reaction was stirred at rt overnight, then concentrated in vacuo. The resulted residue was dissolved in THF (10 mL), followed by the addition of Et$_3$N (0.2 mL, 0.13 mmol). The mixture was stirred in an ammonia gas atmosphere for 1 hour, then concentrated in vacuo, diluted with water (20 mL) and extracted with ethyl acetate (10 mL×3). The combined organic phases were washed with brine (20 mL), dried over anhydrous Na$_2$SO$_4$, concentrated in vacuo and the residue was purified by a silica gel column chromatography (PE/EtOAc (v/v)=5/1) to give the title compound as a yellow solid (70 mg 70%).

MS (ESI, pos. ion) m/z: 157.0 [M+H]$^+$;

$^1$H NMR (300 MHz, CD$_3$OD): δ (ppm) 8.48 (d, J=5.15 Hz, 1H), 8.22 (d, J=2.10 Hz, 1H), 7.79 (br s, 1H), 7.46 (dd, J=5.28 Hz, 2.13 Hz, 1H), 5.80 (br s, 1H).

Step 2) N-(5-hydroxypyridin-2-yl)-2,5-dimethyl-3-oxo-1-phenyl-2,3-dihydro-1H-pyrazole-4-carboxamide A suspension of 2-amino-5-hydroxypyridine hydrochloride (500 mg, 3.41 mmol) and Et$_3$N (0.77 mL, 5.5 mmol) in DMF (8 mL) was stirred at rt for 1 hour. At the same time, to a solution of 1,5-dimethyl-3-oxo-2-phenyl-2,3-dihydro-1H-pyrazole-4-carboxylic acid (0.64 g, 2.75 mmol), HOAT (449 mg, 3.3 mmol) and EDCI (0.63 g, 3.3 mmol) in DMF (8 mL) was added Et$_3$N (0.77 mL, 5.5 mmol) drop wise. The mixture was stirred at rt for 1 hour, followed by the addition of the above prepared mixture. The reaction was heated at 60° C. for 5 hours, then cooled to rt and diluted with water (150 mL). and adjust to pH=6 with HCl (1 M). The mixture was extracted with EtOAc (20 mL×4), and the combined organic phases were washed with brine (20 mL), dried over anhydrous Na$_2$SO$_4$, and concentrated in vacuo. The residue was purified by a silica gel column chromatography (DCM/MeOH (v/v)=10/1) to give the title compound as a pale yellow solid (699 mg, 78%).

MS (ESI, pos. ion) m/z: 325.1 [M+H]$^+$.

Step 3) 4-((6-(1,5-dimethyl-3-oxo-2-phenyl-2,3-dihydro-1H-pyrazole-4-carboxamido)pyridin-3-yl)oxy)picolinamide To a solution of N-(5-hydroxypyridin-2-yl)-1,5-dimethyl-3-oxo-2-phenyl-2,3-dihydro-1H-pyrazole-4-carboxamide (468 mg, 1.4 mmol) in DMF (30 mL) was added potassium tert-butoxide (486 mg, 4.33 mmol). The solution was stirred at rt for 20 minutes, followed by the addition of 4-chloropicolinamide (293 mg, 1.87 mmol). The reaction was heated at 120° C. for 2 hours, then cooled to rt, diluted with water (15 mL) and extracted with EtOAc (20 mL×3). The combined organic phases were washed with brine (20 mL) and concentrated in vacuo. The residue was purified by a silica column chromatography (DCM/MeOH (v/v)=50/1) to give the title compound as an off-white solid (285 mg, 44%).

MS (ESI, pos. ion) m/z: 444.8 [M+H]$^+$.

Step 4) N-(5-((2-aminopyridin-4-yl)oxy)pyridin-2-yl)-1,5-dimethyl-3-oxo-2-phenyl-2,3-dihydro-1H-pyrazole-4-carboxamide To a solution of 4-((6-(1,5-dimethyl-3-oxo-2-phenyl-2,3-dihydro-1H-pyrazole-4-carboxamido)pyridin-3-yl)oxy)picolinamide (60 mg, 0.13 mmol) in EtOAc/MeCN/H$_2$O (2 mL/2 mL/1 mL) was added iodobenzene diacetate (54 mg, 0.16 mmol) at 0° C. The reaction was stirred at rt for 2 hours, then concentrated in vacuo. The resulted residue was dissolved in EtOAc (10 mL), washed with saturated aq. NaHCO$_3$, and then dried over anhydrous Na$_2$SO$_4$. The organic solution was concentrated in vacuo to give the title compound as a yellow solid (43 mg, 77%).

MS (ESI, pos. ion) m/z: 416.9 [M+H]$^+$;

$^1$H NMR (300 MHz, CDCl$_3$): δ (ppm) 11.21 (s, 1H), 8.31 (d, J=9.0 Hz, 1H), 8.13 (d, J=2.8 Hz, 1H), 7.92 (d, J=5.9 Hz, 1H), 7.57-7.27 (m, 6H), 6.29 (dd, J=5.91 Hz, 2.13 Hz, 1H), 5.94 (d, J=2.19 Hz, 1H), 4.51 (br s, 2H), 3.37 (s, 3H), 2.79 (s, 3H).

Step 5) phenyl (4-((6-(1,5-dimethyl-3-oxo-2-phenyl-2,3-dihydro-1H-pyrazole-4-carboxamido)pyridin-3-yl)oxy)pyridin-2-yl)carbamate To a suspension of N-(5-((2-aminopyridin-4-yl)oxy)pyridin-2-yl)-1,5-dimethyl-3-oxo-2-phenyl-2,3-dihydro-1H- pyrazole-4-carboxamide (0.25 g, 0.6 mmol) in DCM (20 mL) was added pyridine (0.65 mL, 6 mmol). The suspension was cooled to 0° C., followed by slowly addition of a solution of phenylcarbonochloridate (98 mg, 0.63 mmol) in DCM (5 mL). The reaction was stirred at rt for 2 hours, diluted with DCM (20 mL), and then washed with water (25 mL×2), followed by washing with brine (25 mL). The organic solution was dried over anhydrous Na$_2$SO$_4$, then concentrated in vacuo, and the residue was purified by a silica gel column chromatography (DCM/MeOH (v/v)=100/1) to give the title compound as a white solid (134 mg, 42%).

MS (ESI, pos. ion) m/z: 536.8 [M+H]$^+$.

Step 6) N-(5-((2-(3-(2-hydroxyethyl)ureido)pyridin-4-yl)oxy)pyridin-2-yl)-1,5-dimethyl-3-oxo-2-phenyl-2,3-dihydro-1H-pyrazole-4-carboxamide A mixture of phenyl (4-((6-(1,5-dimethyl-3-oxo-2-phenyl-2,3-dihydro-1H-pyrazole-4-carboxamido)pyridin-3-yl)oxy)pyridin-2-yl)carbamate (0.1 g, 0.187 mmol), NMP (10 mL) and 2-aminoethanol (14.0 mg, 0.224 mmol) was heated at 40° C. for 2 hours. The solvent was evaporated under reduced pressure at 40° C., and then diluted with EtOAc (20 mL). The precipitate was collected by filtration and washed with EtOAc (3 mL) to give the title compound as a white solid (92 mg, 98%).

MS (ESI, pos. ion) m/z: 504.2 [M+H]$^+$;
$^1$H NMR (300 MHz, DMSO-d$_6$): δ (ppm) 11.23 (s, 1H), 9.14 (s, 1H), 8.33 (d, J=9.0 Hz, 1H), 8.21 (d, J=2.9 Hz, 1H), 8.08 (d, J=5.8 Hz, 1H), 8.04 (br s, 1H), 7.69 (dd, J=8.9 Hz, 2.9 Hz, 1H), 7.63-7.43 (m, 5H), 6.97 (d, J=2.19 Hz, 1H), 6.58 (d, J=5.8 Hz, 1H), 4.73 (t, J=5.2 Hz, 2H), 3.43 (q, J=5.7 Hz, 2H), 3.37 (s, 3H), 3.32 (s, 3H), 3.18 (q, J=5.6 Hz, 2H), 2.72 (s, 3H).

Example 18

N-(5-((2-(3-(2-hydroxyethyl)-3-methylureido)pyridin-4-yl)oxy)pyridin-2-yl)-1,5-dimethyl-3-oxo-2-phenyl-2,3-dihydro-1H-pyrazole-4-carboxamide

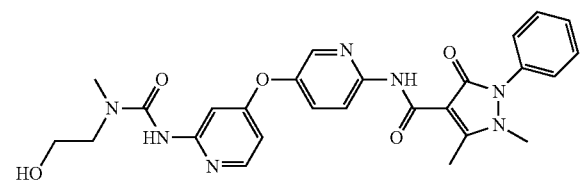 [SMILES: Cc1c(C(=O)Nc2ccc(Oc3ccnc(NC(=O)N(C)CCO)c3)cn2)c(=O)n(-c2ccccc2)n1C]

A mixture of phenyl (4-((6-(1,5-dimethyl-3-oxo-2-phenyl-2,3-dihydro-1H-pyrazole-4-carboxamido)pyridin-3-yl)oxy)pyridin-2-yl)carbamate (30 mg, 0.05 mmol), NMP (5 mL) and 2-(methylamino)ethanol (5.0 mg, 0.06 mmol) was heated at 40° C. for 1.5 hours. The mixture was cooled to rt, and diluted with EtOAc (15 mL) and water (10 mL). The separated organic layer was washed with water (10 mL×3), followed by washing with brine (10 mL), dried over anhydrous MgSO$_4$, and concentrated in vacuo. The residue was purified by a silica gel column chromatography (DCM/MeOH (v/v) =20/1), and then washed with ether (5 mL) to give the title compound as a white solid (17 mg, 59%).

MS (ESI, pos. ion) m/z: 518.2 [M+H]$^+$;
$^1$H NMR (300 MHz, CD$_3$OD): δ (ppm) 8.44 (d, J=9.0 Hz, 1H), 8.24 (d, J=2.85 Hz, 1H), 8.20 (d, J=7.14 Hz, 1H), 7.73 (dd, J=9.0 Hz, 2.88 Hz, 1H), 7.64-7.56 (m, 3H), 7.46-7.43 (m, 2H), 3.72 (t, J=5.2 Hz, 2H), 3.53 (t, J=5.2 Hz, 2H), 3.43 (s, 3H), 3.08 (s, 3H), 2.80 (s, 3H).

Example 19

N-(5-((2-(cyclobutanecarboxamido)pyridin-4-yl)oxy)pyridin-2-yl)-1,5-dimethyl-3-oxo-2-phenyl-2,3-dihydro-1H-pyrazole-4-carboxamide

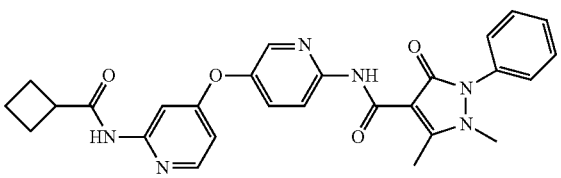 [SMILES: Cc1c(C(=O)Nc2ccc(Oc3ccnc(NC(=O)C4CCC4)c3)cn2)c(=O)n(-c2ccccc2)n1C]

To a suspension of N-(5-((2-aminopyridin-4-yl)oxy)pyridin-2-yl)-1,5-dimethyl-3-oxo-2-phenyl-2,3-dihydro-1H-pyrazole-4-carboxamide (50 mg, 0.12 mmol) in THF (13 mL) was added Et$_3$N (0.034 mL, 0.24 mmol). The suspension was cooled to 0° C., then a solution of cyclobutanecarbonyl chloride (28.5 mg, 0.24 mmol) in THF (3 mL) was added to the mixture slowly. The reaction was stirred at rt for 1.25 hours, then diluted with EtOAc (15 mL). The mixture was washed with water (15 mL×2), followed by washing with brine (15 mL), dried over anhydrous Na$_2$SO$_4$, and concentrated in vacuo. The residue was purified by a silica gel column chromatography (DCM/MeOH (v/v)=60/1) to give the title compound as a white solid (25 mg, 41%).

MS (ESI, pos. ion) m/z: 499.2 [M+H]$^+$;
$^1$H NMR (300 MHz, CDCl$_3$): δ (ppm) 11.21 (s, 1H), 8.35 (d, J=9.0 Hz, 1H), 8.14 (d, J=2.6 Hz, 1H), 8.13-8.08 (m, 2H), 7.89-7.88 (m, 1H), 7.55-7.35 (m, 1H), 6.56 (d, J=3.0 Hz, 1H), 3.36 (s, 3H), 3.22-3.11 (m, 1H), 2.78 (s, 3H), 2.43-2.29 (m, 2H), 2.26-2.15 (m, 2H), 2.04-1.87 (m, 2H).

Example 20

N-(5-((2-(3-hydroxycyclobutanecarboxamido)pyridin-4-yl)oxy)pyridin-2-yl)-1,5-dimethyl-3-oxo-2-phenyl-2,3-dihydro-1H-pyrazole-4-carboxamide

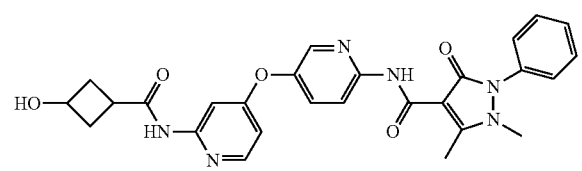 [SMILES: Cc1c(C(=O)Nc2ccc(Oc3ccnc(NC(=O)C4CC(O)C4)c3)cn2)c(=O)n(-c2ccccc2)n1C]

Step 1) 3-acetoxycyclobutanecarboxylic acid

To a solution of 3-hydroxycyclobutanecarboxylic acid (100 mg, 0.86 mmol) in DCM (10 mL) was added DMAP (1.0 mg, 0.086 mmol). The solution was cooled to 0° C., followed by the addition of acetyl chloride (0.14 mL, 2.6 mmol). The reaction was heated at 45° C. for 4 hours, then cooled to rt and diluted with DCM (20 mL). The mixture was washed with water (10 mL), followed by washing with brine (10 mL), dried over anhydrous Na$_2$SO$_4$, filtered, and concentrated in vacuo to obtained the crude product which was used in the next step without further purification.

Step 2) 3-((4-((6-(1,5-dimethyl-3-oxo-2-phenyl-2,3-dihydro-1H-pyrazole-4-carboxamido)pyridin-3-yl)oxy)pyridin-2-yl)carbamoyl)cylcobutyl acetate To a solution of N-(5-((2-aminopyridin-4-yl)oxy)pyridin-2-yl)-1,5-dimethyl-3-oxo-2-phenyl-2,3-dihydro-1H-pyrazole-4-carboxamide (50 mg, 0.12 mmol), HOAT (19 mg, 0.24 mmol), EDCI (28 mg, 0.14 mmol) and DIPEA (0.1 mL, 0.6 mmol) in DMF (5 mL) was added a solution of 3-acetoxycyclobutanecarboxylic acid in DMF (5 mL) at 0° C. The reaction was heated at 120° C. for 5 hours, then cooled to rt, diluted with water (50 mL) and extracted with EtOAc (30 mL×3). The combined organic phases were washed with brine (10 mL), dried over anhydrous $Na_2SO_4$, filtered, and concentrated in vacuo. The resulted residue was purified by a silica gel column chromatography (DCM/EtOAc (v/v)=1/2) to give the title compound as a white solid (20 mg, 30%).
MS (ESI, pos. ion) m/z: 556.9 [M+H]$^+$.

Step 3) N-(5-((2-(3-hydroxycyclobutanecarboxamido)pyridin-4-yl)oxy)pyridin-2-yl)-1,5-dimethyl-3-oxo-2-phenyl-2,3-dihydro-1H-pyrazole-4-carboxamide A solution of 3-((4-((6-(1,5-dimethyl-3-oxo-2-phenyl-2,3-dihydro-1H-pyrazole-4-carboxamido)pyridin-3-yl)oxy)pyridin-2-yl)carbamoyl)cyclobutyl acetate (40 mg, 0.072 mmol) in MeOH (2.5 mL) was cooled to 0° C., then NaOH (6 mg, 0.144 mmol) was added to the mixture. The reaction was stirred at rt for 1 hour, then concentrated in vacuo. The residue was washed with water (5 mL) and ether (5 mL), then filtered to give the title compound as a white solid (17 mg, 42%).
MS (ESI, pos. ion) m/z: 515.0 [M+H]$^+$;
$^1$H NMR (300 MHz, DMSO-d$_6$): δ (ppm) 11.24 (s, 1H), 10.48 (s, 1H), 8.33 (d, J=9.0 Hz, 1H), 8.23 (d, J=2.88 Hz, 1H), 8.19 (d, J=5.7 Hz, 1H), 7.73-7.69 (m, 2H), 7.63-7.5 (m, 3H), 7.46-7.43 (m, 2H), 6.72 (dd, J=2.4 Hz, 5.7 Hz, 1H), 5.09 (d, J=7.3 Hz, 1H), 3.96 (m, 1H), 3.37 (s, 3H), 2.72 (s, 3H), 2.77-2.66 (m, 1H), 2.34-2.26 (m, 2H), 2.04-1.91 (m, 2H).

Example 21

N-(4-((2-(cyclobutanecarboxamido)pyridin-4-yl)oxy)-3-fluorophenyl)-1,5-dimethyl-3-oxo-2-phenyl-2,3-dihydro-1H-pyrazole-4-carboxamide

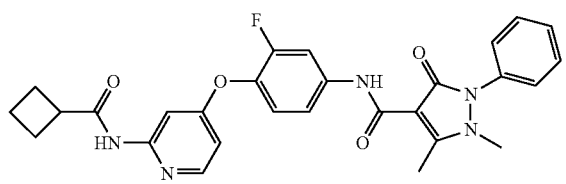 [SMILES: Cc1c(C(=O)Nc2ccc(Oc3ccnc(NC(=O)C4CCC4)c3)c(F)c2)c(=O)n(-c2ccccc2)n1C]

Step 1) 4-amino-2-fluorophenol

To a solution of 2-fluoro-4-nitrophenol (5.0 g, 31.8 mmol) in methanol (200 mL) was added Pd/C (1.0 g, 10%). The reaction was stirred at rt overnight in a H$_2$ atmosphere. The mixture was filtered through a pad of CELITE®, then washed with MeOH (5 mL). The filtrate was concentrated in vacuo to give the title compound as a brown solid (4.02 g, >99%).
MS (ESI, pos. ion) m/z: 128.1 [M+H]$^+$.

Step 2) N-(3-fluoro-4-hydroxyphenyl)-1,5-dimethyl-3-oxo-2-phenyl-2,3-dihydro-1H-pyrazole-4-carboxamide To a solution of 1,5-dimethyl-3-oxo-2-phenyl-2,3-dihydro-1H-pyrazole-4-carboxylic acid (6.12 g, 26.3 mmol), HOAT (4.3 g, 31.6 mmol) and EDCI (6.03 g, 31.6 mmol) in DMF (200 mL) was added Et$_3$N (9.2 mL, 65.8 mmol) drop wise. The solution was stirred at rt for 20 minutes, then a solution of 4-amino-2-fluorophenol (4.02 g, 31.6 mmol) in DMF (20 mL) was added to the system. The reaction was heated at 70° C. for 4 hours, then concentrated to 2 mL in vacuo, and diluted with H$_2$O/EtOAc (150 mL/50 mL). The precipitate was obtained by filtration, and then washed with EtOAc (10 mL), dried to give the product as brown (5.49 g); the filtrate was separated, and the organic phase was concentrated in vacuo. The resulted residue was purified by a silica gel column chromatography (DCM/EtOAc (v/v)=10/1) to give a yellow solid (1.692 g). The title compound was obtained by combining the precipitate and the yellow solid for 80% yield.
MS (ESI, pos. ion) m/z: 342.0 [M+H]$^+$;
$^1$H NMR (300 MHz, CDCl$_3$): δ (ppm) 10.58 (s, 1H), 7.72 (dd, J=2.4 Hz, 12.69 Hz, 1H), 7.58-7.32 (m, 5H), 7.09-7.04 (m, 1H), 6.89 (t, J=9.3 Hz, 1H), 3.34 (s, 3H), 2.78 (s, 3H).

Step 3) 4-(4-(1,5-dimethyl-3-oxo-2-phenyl-2,3-dihydro-1H-pyrazole-4-carboxamido)-2-fluorophenoxy)picolinamide To a solution of N-(3-fluoro-4-hydroxyphenyl)-1,5-dimethyl-3-oxo-2-phenyl-2,3-dihydro-1H-pyrazole-4-carboxamide (7.18 g, 21.1 mmol) in DMF (200 mL) was added potassium tert-butoxide (7.08 g, 63.2 mmol). The solution was stirred at rt for 20 minutes, followed by the addition of 4-chloropicolinamide (4.27 g, 25.2 mmol). The reaction was heated at 120° C. for 3 hours, then concentrated to 2 mL in vacuo, and diluted with water (60 mL). The precipitate was obtained by filtration, and then washed with water (10 mL). The crude product was purified by a silica gel column chromatography (DCM/EtOAc/MeOH (v/v/v)=1/1/0.05) to give the title compound as a yellow solid (4.15 g, 43% yield).
MS (ESI, pos. ion) m/z: 462.0 [M+H]$^+$;
$^1$H NMR (300 MHz, DMSO-d$_6$): δ (ppm) 10.97 (s, 1H), 8.53 (d, J=6.0 Hz, 1H), 8.12 (br s, 1H), 7.97 (dd, J=2.0 Hz, 13.23 Hz, 1H), 7.72 (br s, 1H), 7.63-7.42 (m, 5H), 7.42-7.32 (m, 3H), 7.21 (dd, J=2.7 Hz, 5.7 Hz, 1H), 3.37 (s, 3H), 2.71 (s, 3H).

Step 4) N-(4-((2-aminopyridin-4-yl)oxy)-3-fluorophenyl)-1,5-dimethyl-3-oxo-2-phenyl-2,3-dihydro-1H-pyrazole-4-carboxamide To a solution of 4-(4-(1,5-dimethyl-3-oxo-2-phenyl-2,3-dihydro-1H-pyrazole-4-carboxamido)-2-fluorophenoxy)picolinamide (2.5 g, 6.0 mmol) in EtOAc/MeCN/H$_2$O (60 mL/60 mL/30 mL) was added iodobenzene diacetate (2.9 g, 9.0 mmol) at 0° C. The reaction was stirred at rt for 2 hours, then concentrated in vacuo. The resulted residue was dissolved with EtOAc (150 mL), washed with saturated aq. NaHCO$_3$ (80 mL), dried over anhydrous Na$_2$SO$_4$, and concentrated in vacuo. The residue was washed with DCM/ether (1/10, 22 mL) to give the title compound as a yellow solid (2.09 g, 81% yield).

MS (ESI, pos. ion) m/z: 434.0 [M+H]$^+$;

$^1$H NMR (300 MHz, CDCl$_3$): δ (ppm) 10.83 (s, 1H), 7.92 (d, J=5.8 Hz, 1H), 7.84 (dd, J=2.4 Hz, 12.5 Hz, 1H), 7.60-7.33 (m, 5H), 7.26-7.22 (m, 1H), 7.06 (t, J=8.7 Hz, 1H), 6.29 (dd, J=2.2 Hz, 5.9 Hz, 1H), 5.92 (d, J=2.19 Hz, 1H), 4.40 (br s, 2H), 3.37 (s, 3H), 2.79 (s, 3H).

Step 5) N-(4-((2-(cyclobutanecarboxamido)pyridin-4-yl)oxy)-3-fluorophenyl)-1,5-dimethyl-3-oxo-2-phenyl-2,3-dihydro-1H-pyrazole-4-carboxamide To a suspension of N-(4-((2-aminopyridin-4-yl)oxy)-3-fluorophenyl)-1,5-dimethyl-3-oxo-2-phenyl-2,3-dihydro-1H-pyrazole-4-carboxamide (100 mg, 0.231 mmol) in THF/DMF (15 mL/0.5 mL) was added Et$_3$N (0.058 mL, 0.462 mmol). The suspension was cooled to 0° C., then a solution of cyclobutanecarbonyl chloride (30 mg, 0.254 mmol) in THF (5 mL) was added to the mixture drop wise over 1 hour. The reaction was stirred at rt for 2 hours, then diluted with EtOAc (20 mL). The mixture was washed with water (25 mL×3), followed by washing with brine (25 mL), dried over anhydrous Na$_2$SO$_4$, filtered, and concentrated in vacuo. The residue was purified by a silica gel column chromatography (DCM/EtOAc/MeOH (v/v/v)=100/20/1) to give the title compound as a white solid (51 mg, 44%).

MS (ESI, pos. ion) m/z: 516.0 [M+H]$^+$;

$^1$H NMR (300 MHz, CDCl$_3$): δ (ppm) 10.84 (s, 1H), 8.06 (d, J=5.8 Hz, 1H), 7.91-7.86 (m, 3H), 7.59-7.35 (m, 5H), 7.28-7.24 (m, 1H), 7.09 (t, J=8.7 Hz, 1H), 6.56 (dd, J=2.9 Hz, 5.8 Hz, 1H), 3.68 (s, 3H), 3.16 (m, 1H), 2.79 (s, 3H), 2.43-2.29 (m, 2H), 2.26-2.15 (m, 2H), 2.06-1.84 (m, 2H).

Example 22

N-(3-fluoro-4-((2-(3-(2-hydroxyethyl)ureido)pyridin-4-yl)oxy)phenyl)-1,5-dimethyl-3-oxo-2-phenyl-2,3-dihydro-1H-pyrazole-4-carboxamide

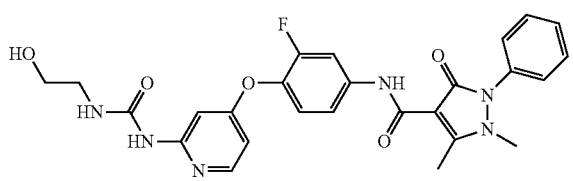 [SMILES: Cc1c(C(=O)Nc2ccc(Oc3ccnc(NC(=O)NCCO)c3)c(F)c2)c(=O)n(-c2ccccc2)n1C]

Step 1) phenyl (4-(4-(1,5-dimethyl-3-oxo-2-phenyl-2,3-dihydro-1H-pyrazole-4-carboxamido)-2-fluorophenoxy)pyridin-2-yl)carbamate A suspension of N-(4-((2-aminopyridin-4-yl)oxy)-3-fluorophenyl)-1,5-dimethyl-3-oxo-2-phenyl-2,3-dihydro-1H-pyrazole-4-carboxamide (500 mg, 1.10 mmol) in DCM/pyridine (50 mL/25 mL) was cooled to 0° C., then a solution of phenylcarbonochloridate (450 mg, 2.90 mmol) in DCM (5 mL) was added to the mixture slowly over 0.5 hour. The reaction was stirred at rt for 2 hours, then diluted with DCM (250 mL). The mixture was washed with water (150 mL×3), followed by washing with brine (150 mL), dried over anhydrous Na$_2$SO$_4$, filtered, and concentrated in vacuo. The residue was purified by a silica gel column chromatography (DCM/MeOH (v/v)=150/1) to give the title compound as a white solid (352 mg, 46%).

MS (ESI, pos. ion) m/z: 554.0 [M+H]$^+$.

Step 2) N-(3-fluoro-4-((2-(3-(2-hydroxyethyl)ureido)pyridin-4-yl)oxy)phenyl)-1,5-dimethyl-3-oxo-2-phenyl-2,3-dihydro-1H-pyrazole-4-carboxamide A mixture of phenyl (4-(4-(1,5-dimethyl-3-oxo-2-phenyl-2,3-dihydro-1H-pyrazole-4-carboxamido)-2-fluorophenoxy)pyridin-2-yl)carbamate (100 mg, 0.18 mmol), NMP (5 mL) and 2-aminoethanol (3.0 mg, 0.22 mmol) was heated at 40° C. for 2 hours. The solvent was evaporated under reduced pressure at 40° C., and diluted with EtOAc (20 mL). The precipitate was collected by filtration, and then washed with EtOAc (3 mL) to give the title compound as a white solid (65 mg, 69%).

MS (ESI, pos. ion) m/z: 521.0 [M+H]$^+$;

$^1$H NMR (300 MHz, DMSO-d$_6$): δ (ppm) 10.94 (s, 1H), 9.14 (s, 1H), 8.06 (d, J=5.9 Hz, 1H), 8.00 (br s, 1H), 7.94 (dd, J=1.50 Hz, 12.84 Hz, 1H), 7.63-7.42 (m, 5H), 7.31-7.29 (m, 2H), 6.97 (d, J=2.04 Hz, 1H), 6.56 (dd, J=2.4 Hz, 5.9 Hz, 1H), 4.72 (t, J=5.1 Hz, 1H), 3.42 (q, J=5.4 Hz, 2H), 3.37 (s, 3H), 3.17 (q, J=5.6 Hz, 2H), 2.70 (s, 3H).

Example 23

N-(3-fluoro-4-((2-(3-(2-hydroxypropyl)-3-methylureido)pyridin-4-yl)oxy)phenyl)-1,5-dimethyl-3-oxo-2-phenyl-2,3-dihydro-1H-pyrazole-4-carboxamide A mixture of phenyl (4-(4-(1,5-dimethyl-3-oxo-2-phenyl-2,3-dihydro-1H-pyrazole-4-carboxamido)-2-fluorophenoxy)pyridin-2-yl)carbamate (100 mg, 0.18 mmol), NMP (5 mL) and 1-aminopropan-2-ol (16 mg, 0.2 mmol) was heated at 40° C. for 2 hours. The solvent was evaporated under reduced pressure at 40° C., and then diluted with EtOAc (20 mL). The precipate was collected by filtration to give the title compound as a white solid (58 mg, 60%).

MS (ESI, pos. ion) m/z: 535.0 [M+H]$^+$;

$^1$H NMR (300 MHz, DMSO-d$_6$): δ (ppm) 10.94 (s, 1H), 9.14 (s, 1H), 8.06 (d, J=5.8 Hz, 1H), 7.98 (br s, 1H), 7.93 (dd, J=1.5 Hz, 12.8 Hz, 1H), 7.63-7.42 (m, 5H), 7.31-7.29 (m, 2H), 6.97 (d, J=2.1 Hz, 1H), 6.56 (dd, J=2.4 Hz, 5.8 Hz, 1H), 4.73 (d, J=4.8 Hz, 1H), 3.69-3.61 (m, 1H), 3.37 (s, 3H), 3.18-3.10 (m, 1H), 3.00-2.92 (m, 1H), 2.70 (s, 3H), 1.02 (d, J=6.2 Hz, 3H).

Example 24

N-(4-((2-(3,3-dimethylureido)pyridin-4-yl)oxy)-3-fluorophenyl)-1,5-dimethyl-3-oxo-2-phenyl-2,3-dihydro-1H-pyrazole-4-carboxamide

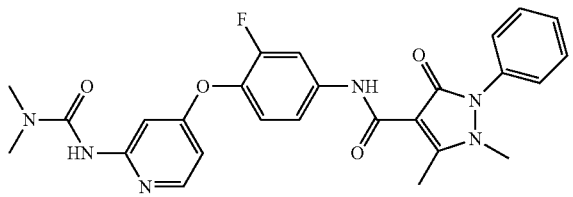 [SMILES: Cc1c(C(=O)Nc2ccc(Oc3ccnc(NC(=O)N(C)C)c3)c(F)c2)c(=O)n(-c2ccccc2)n1C]

A mixture of phenyl (4-(4-(1,5-dimethyl-3-oxo-2-phenyl-2,3-dihydro-1H-pyrazole-4-carboxamido)-2-fluorophenoxy)pyridin-2-yl)carbamate (100 mg, 0.18 mmol), NMP (5 mL) and aqueous dimethylamine (0.045 mL, 33%) was heated at 40° C. for 2 hours. The solvent was evaporated under reduced pressure at 40° C., and then diluted with EtOAc (20 mL). The precipitate was collected by filtration to give the title compound as a white solid (25 mg, 27%).

MS (ESI, pos. ion) m/z: 505.0 [M+H]$^+$;

$^1$H NMR (300 MHz, CD$_3$OD): δ (ppm) 8.07 (d, J=5.8 Hz, 1H), 7.88 (dd, J=2.4 Hz, 12.9 Hz, 1H), 7.66-7.43 (m, 5H), 7.31-7.27 (m, 1H), 7.21 (t, J=8.7 Hz, 1H), 6.59 (dd, J=2.4 Hz, 5.8 Hz, 1H), 4.84 (s, 3H), 3.41 (s, 3H), 3.00 (s, 6H), 2.76 (s, 3H).

Example 25

N-(4-((2-(3-ethyl-3-methylureido)pyridin-4-yl)oxy)-3-fluorophenyl)-1,5-dimethyl-3-oxo-2-phenyl-2,3-dihydro-1H-pyrazole-4-carboxamide

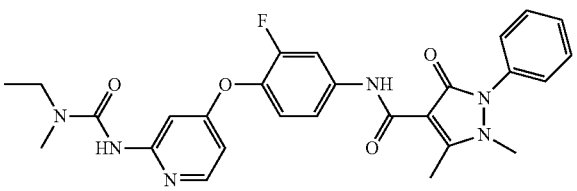 [SMILES: CCN(C)C(=O)Nc1cc(Oc2ccc(NC(=O)c3c(C)n(C)n(-c4ccccc4)c3=O)cc2F)ccn1]

A mixture of phenyl (4-(4-(1,5-dimethyl-3-oxo-2-phenyl-2,3-dihydro-1H-pyrazole-4-carboxamido)-2-fluorophenoxy)pyridin-2-yl)carbamate (100 mg, 0.18 mmol), NMP (5 mL) and N-methylethanamine (12 mg, 0.2 mmol) was heated at 40° C. for 2 hours. The solvent was evaporated under reduced pressure at 40° C., and then diluted with water (10 mL). The precipitate was collected by filtration, and then purified by a silica gel column chromatography (DCM/MeOH (v/v)=60/1) to give the title compound as a white solid (55 mg, 62%).

MS (ESI, pos. ion) m/z: 519.3 [M+H]$^+$;

$^1$H NMR (300 MHz, CD$_3$OD): δ (ppm) 8.07 (d, J=5.8 Hz, 1H), 7.88 (dd, J=2.4 Hz, 12.9 Hz, 1H), 7.66-7.43 (m, 5H), 7.31-7.27 (m, 1H), 7.21 (t, J=8.6 Hz, 1H), 6.59 (dd, J=2.4 Hz, 5.8 Hz, 1H), 3.41 (s, 3H), 3.40 (q, J=7.2 Hz, 2H), 2.99 (s, 3H), 1.76 (s, 3H), 1.16 (t, J=7.2 Hz, 3H).

Example 26

N-(4-((2-(cyclobutanecarboxamido)pyridin-4-yl)oxy)phenyl)-1,5-dimethyl-3-oxo-2-phenyl-2,3-dihydro-1H-pyrazole-4-carboxamide

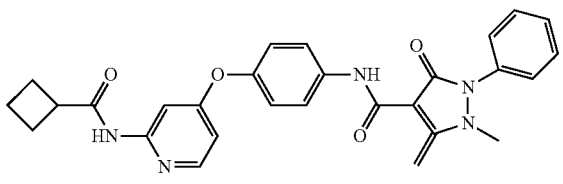

Step 1) 4-aminophenol

To a solution of 4-nitrophenol (2 g, 14.4 mmol) in EtOH (80 mL) was added Pd/C (10%, 300 mg). The reaction was stirred at rt for 5 hours in a H$_2$ atmosphere, then filtered through a pad of CELITE®, which was washed with EtOH (10 mL). The filtrate was concentrated in vacuo to give the title compound as a brown solid (1.58 g, >99%).

MS (ESI, pos. ion) m/z: 110.1 [M+H]$^+$.

Step 2) N-(4-hydroxyphenyl)-1,5-dimethyl-3-oxo-2-phenyl-2,3-dihydro-1H-pyrazole-4-carboxamide To a solution of 1,5-dimethyl-3-oxo-2-phenyl-2,3-dihydro-1H-pyrazole-4-carboxylic acid (1.70 g, 7.35 mmol), HOAT (1.2 g, 8.82 mmol), and EDCI (1.68 g, 8.82 mmol) in DMF (40 mL) was added Et$_3$N (2.6 mL, 18.38 mmol) drop wise. The solution was stirred at rt for 20 minutes, then a solution of 4-aminophenol (994 mg, 9.11 mmol) in DMF (6 mL) was added drop wise to the reaction system. The reaction was heated at 70° C. for 5 hours, then concentrated to 2 mL in vacuo, and diluted with water (50 mL). The precipitate was collected by filtration, washed with water (5 mL) and dried. The crude product was washed with DCM (20 mL) to give the title compound as a brown solid (2.02 g, 85%).

MS (ESI, pos. ion) m/z: 324.0 [M+H]$^+$;

$^1$H NMR (300 MHz, DMSO-d$_6$): δ (ppm) 10.46 (s, 1H), 9.17 (s, 1H), 7.61-7.55 (m, 2H), 7.52-7.46 (m, 1H), 7.43-7.34 (m, 4H), 6.73-6.68 (m, 2H), 3.33 (s, 3H), 2.69 (s, 3H).

Step 3) 4-(4-(1,5-dimethyl-3-oxo-2-phenyl-2,3-dihydro-1H-pyrazole-4-carboxamido)phenoxy)picolinamide To a solution of N-(4-hydroxyphenyl)-1,5-dimethyl-3-oxo-2-phenyl-2,3-dihydro-1H-pyrazole-4-carboxamide (1.80 g, 5.57 mmol) in DMF (35 mL) was added potassium tert-butoxide (1.87 g, 16.7 mmol). The solution was stirred at rt for 20 minutes, followed by the addition of 4-chloropicolinamide (1.046 g, 6.68 mmol). The reaction was heated at 120° C. for 3 hours, then concentrated to 2 mL in vacuo, and diluted with water (60 mL). The precipitate was obtained by filtration, washed with water (5 mL) and dried. The crude product was washed with DCM (20 mL) to give the title compound as a brown solid (1.8 g, 73%).

MS (ESI, pos. ion) m/z: 444.2 [M+H]$^+$;

$^1$H NMR (300 MHz, DMSO-d$_6$): δ (ppm) 10.84 (s, 1H), 8.51 (d, J=5.64 Hz, 1H), 8.11 (d, J=2.64 Hz, 1H), 7.75-7.69 (m, 3H), 7.63-7.56 (m, 2H), 7.54-7.48 (m, 1H), 7.46-7.39 (m, 3H), 7.22-7.15 (m, 3H), 3.36 (s, 3H), 2.71 (s, 3H).

Step 4) N-(4-((2-aminopyridin-4-yl)oxy)phenyl)-1,5-dimethyl-3-oxo-2-phenyl-2,3-dihydro-1H-pyrazole-4-carboxamide To a solution of 4-(4-(1,5-dimethyl-3-oxo-2-phenyl-2,3-dihydro-1H-pyrazole-4-carboxamido)phenoxy)picolinamid (1.773 g, 3.998 mmol) in EtOAc/MeCN/H$_2$O (20 mL/20 mL/10 mL) was added iodobenzene diacetate (1.6 g, 4.96 mmol) at 0° C. The reaction was stirred at rt overnight, then concentrated in vacuo and diluted with EtOAc (100 mL). The mixture was washed with saturated aq. NaHCO$_3$ (60 mL), dried over Na$_2$SO$_4$, and concentrated in vacuo. The residue was purified by a silica gel column chromatography (DCM/MeOH (v/v)=30/1) to give the title compound as a yellow solid (799 mg, 48%).

MS (ESI, pos. ion) m/z: 416.1 [M+H]$^+$;
$^1$H NMR (300 MHz, DMSO-d$_6$): δ (ppm) 10.77 (s, 1H), 7.78 (d, J=9.8 Hz, 1H), 7.68-7.63 (m, 2H), 7.62-7.56 (m, 2H), 7.54-7.48 (m, 1H), 7.45-7.41 (m, 2H), 6.13 (dd, J=2.3 Hz, 9.8 Hz, 1H), 5.90 (br s, 2H), 5.82 (d, J=2.2 Hz, 1H), 3.36 (s, 3H), 2.71 (s, 3H).

Step 5) N-(4-((2-(cyclobutanecarboxamido)pyridin-4-yl)oxy)phenyl)-1,5-dimethyl-3-oxo-2-phenyl-2,3-dihydro-1H-pyrazole-4-carboxamide To a suspension of N-(4-((2-aminopyridin-4-yl)oxy)phenyl)-1,5-dimethyl-3-oxo-2-phenyl-2,3-dihydro-1H-pyrazole-4-carboxamide (100 mg, 0.241 mmol) in THF/DMF (15 mL/1 mL) was added Et$_3$N (0.06 mL, 0.482 mmol). The suspension was cooled to 0° C., then a solution of cyclobutanecarbonyl chloride (31.0 mg, 0.265 mmol) in THF (5 mL) was added to the reaction system drop wise over 1 hour. The reaction was stirred at rt for 5 hours, and then diluted with EtOAc (20 mL). The resulted mixture was washed with water (25 mL×3), followed by washing with brine (25 mL), dried over anhydrous Na$_2$SO$_4$, filtered and concentrated in vacuo. The residue was purified by a silica gel column chromatography (DCM/EtOAc/MeOH (v/v)=100/25/1) to give the title compound as a white solid (30 mg, 25%).

MS (ESI, pos. ion) m/z: 498.0 [M+H]$^+$;
$^1$H NMR (300 MHz, CDCl$_3$): δ (ppm) 10.73 (s, 1H), 8.05 (d, J=5.8 Hz, 1H), 7.87-7.86 (m, 2H), 7.74-7.70 (m, 2H), 7.58-7.36 (m, 5H), 7.07-7.03 (m, 2H), 6.54 (dd, J=2.3 Hz, 5.8 Hz, 1H), 3.35 (s, 3H), 3.22-3.10 (m, 1H), 2.80 (s, 3H), 2.43-2.31 (m, 2H), 2.26-2.15 (m, 2H), 2.08-1.86 (m, 2H).

Example 27

N-(4-((2-(cyclopentanecarboxamido)pyridin-4-yl)oxy)phenyl)-1,5-dimethyl-3-oxo-2-phenyl-2,3-dihydro-1H-pyrazole-4-carboxamide

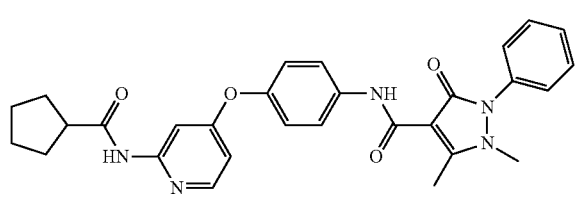 [SMILES: Cc1c(C(=O)Nc2ccc(Oc3ccnc(NC(=O)C4CCCC4)c3)cc2)c(=O)n(-c2ccccc2)n1C]

To a suspension of N-(4-((2-aminopyridin-4-yl)oxy)phenyl)-1,5-dimethyl-3-oxo-2-phenyl-2,3-dihydro-1H-pyrazole-4-carboxamide (100 mg, 0.241 mmol) in THF/DMF (20 mL/1 mL) was added Et$_3$N (0.06 mL, 0.481 mmol). The suspension was cooled to 0° C., a solution of cyclopentanecarbonyl chloride (64.0 mg, 0.481 mmol) in THF (5 mL) was added to the reaction mixture drop wise over 2 hours. The reaction was stirred at rt for 1.5 hours, then diluted with EtOAc (25 mL). The resulted mixture was washed with water (25 mL×3), followed by washing with brine (25 mL), dried over anhydrous Na$_2$SO$_4$, filtered and concentrated in vacuo. The residue was purified by a silica gel column chromatography (DCM/EtOAc/MeOH (v/v)=80/15/1) to give the title compound as a white solid (39 mg, 32%).

MS (ESI, pos. ion) m/z: 512.2 [M+H]$^+$;
$^1$H NMR (300 MHz, CDCl$_3$): δ (ppm) 10.73 (s, 1H), 8.05 (d, J=5.7 Hz, 1H), 8.01 (br s, 1H), 7.73-7.68 (m, 2H), 7.58-7.34 (m, 5H), 7.06-7.01 (m, 2H), 6.54 (dd, J=2.4 Hz, 5.7 Hz, 1H), 3.35 (s, 3H), 2.79 (s, 3H), 2.71-2.63 (m, 1H), 1.95-1.57 (m, 8H).

Example 28

N-(4-((2-(3-(2-hydroxyethyl)-3-methylureido)pyridin-4-yl)oxy)phenyl)-1,5-dimethyl-3-oxo-2-phenyl-2,3-dihydro-1H-pyrazole-4-carboxamide

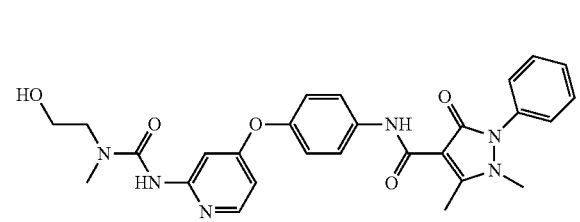 [SMILES: Cc1c(C(=O)Nc2ccc(Oc3ccnc(NC(=O)N(C)CCO)c3)cc2)c(=O)n(-c2ccccc2)n1C]

Step 1) phenyl (4-(4-(1,5-dimethyl-3-oxo-2-phenyl-2,3-dihydro-1H-pyrazole-4-carboxamido)phenoxy)pyridin-2-yl)carbamate A suspension of N-(4-((2-aminopyridin-4-yl)oxy)phenyl)-1,5-dimethyl-3-oxo-2-phenyl-2,3-dihydro-1H-pyrazole-4-carboxamide (600 mg, 1.44 mmol) in DCM/pyridine (30 mL/20 mL) was cooled to 0° C., then a solution of phenylcarbonochloridate (565 mg, 3.61 mmol) in DCM (10 mL) was added to the mixture slowly over 1 hour. The reaction was stirred at rt for 2 hours, then diluted with DCM (200 mL). The mixture was washed with water (140 mL×4), followed by washing with brine (150 mL), dried over anhydrous Na$_2$SO$_4$, filtered, and concentrated in vacuo. The residue was purified by a silica gel column chromatography (DCM/EtOAc (v/v)= 2/1) to give the title compound as a white solid (327 mg, 42%).

MS (ESI, pos. ion) m/z: 536.0 [M+H]$^+$.

Step 2) N-(4-((2-(3-(2-hydroxyethyl)-3-methylureido)pyridin-4-yl)oxy)phenyl)-1,5-dimethyl-3-oxo-2-phenyl-2,3-dihydro-1H-pyrazole-4-carboxamide A mixture of phenyl (4-(4-(1,5-dimethyl-3-oxo-2-phenyl-2,3-dihydro-1H-pyrazole-4-carboxamido)phenoxy)pyridin-2-yl)carbamate (50 mg, 0.093 mmol), NMP (3 mL) and 2-(methylamino)ethanol (8.4 mg, 0.112 mmol) was heated at 40° C. for 2 hours. The solvent was evaporated under reduced pressure at 40° C., and then diluted with EtOAc (10 mL). The resulted mixture was washed with water (7 mL×3), followed by washing with brine (10 mL), dried over anhydrous Na$_2$SO$_4$, filtered, and concentrated in vacuo. The residue was washed with EtOAc (2 mL) to give the title compound as a white solid (25 mg, 52%).

MS (ESI, pos. ion) m/z: 517.0 [M+H]$^+$;

$^1$H NMR (300 MHz, DMSO-d$_6$): δ (ppm) 10.80 (s, 1H), 9.04 (s, 1H), 8.06 (d, J=5.7 Hz, 1H), 7.70-7.65 (m, 2H), 7.62-7.41 (m, 5H), 7.36 (d, J=2.2 Hz, 1H), 7.14-7.09 (m, 2H), 6.54 (dd, J=2.3 Hz, 5.7 Hz, 1H), 5.31 (br s, 1H), 3.56 (q, J=4.8 Hz, 2H), 3.36 (s, 3H), 3.36-3.33 (m, 2H), 2.88 (s, 3H), 2.71 (s, 3H).

Example 29

1,5-dimethyl-N-(4-((2-(3-methylureido)pyridin-4-yl) oxy)phenyl)-3-oxo-2-phenyl-2,3-dihydro-1H-pyrazole-4-carboxamide

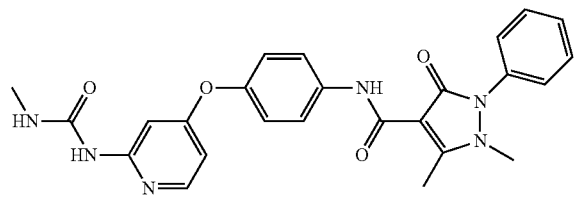 [SMILES: CNC(=O)Nc1cc(Oc2ccc(NC(=O)c3c(C)n(C)n(-c4ccccc4)c3=O)cc2)ccn1]

A mixture of phenyl (4-(4-(1,5-dimethyl-3-oxo-2-phenyl-2,3-dihydro-1H-pyrazole-4-carboxamido)phenoxy)pyridin-2-yl)carbamate (100 mg, 0.187 mmol), NMP (3 mL) and methylamine solution (25%, 0.2 mL) was heated at 40° C. overnight. The solvent was evaporated under reduced pressure at 40° C., and then diluted with water (10 mL). The precipitate was collected by filtration, and then purified by a silica gel column chromatography (DCM/EtOAc/MeOH (v/v/v)=1/1/0.01) to give the title compound as a white solid (46 mg, 52%).

MS (ESI, pos. ion) m/z: 473.1 [M+H]$^+$;

$^1$H NMR (300 MHz, DMSO-d$_6$): δ (ppm) 10.81 (s, 1H), 9.13 (s, 1H), 8.04 (d, J=5.9 Hz, 1H), 7.99-7.94 (m, 1H), 7.71-7.65 (m, 2H), 7.62-7.42 (m, 5H), 7.15-7.09 (m, 2H), 6.87 (d, J=2.28 Hz, 1H), 6.51 (dd, J=2.3 Hz, 5.9 Hz, 1H), 3.36 (s, 3H), 2.71 (s, 3H), 2.68 (d, J=4.6 Hz, 3H).

Example 30

N-(4-((2-(3-ethylureido)pyridin-4-yl)oxy)phenyl)-1, 5-dimethyl-3-oxo-2-phenyl-2,3-dihydro-1H-pyrazole-4-carboxamide

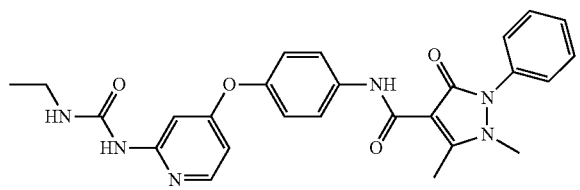

To a solution of ethylamine hydrochloride (29 mg, 0.356 mmol) was in NMP (3 mL) was added Et$_3$N (0.1 mL). The solution was stirred at rt for 10 minutes, followed by the addition of phenyl (4-(4-(1,5-dimethyl-3-oxo-2-phenyl-2,3-dihydro-1H-pyrazole-4-carboxamido)phenoxy)pyridin-2-yl)carbamate (100 mg, 0.187 mmol). The reaction was stirred at 40° C. overnight, then concentrated in vacuo at 40° C., and diluted with water (10 mL). The precipitate was collected by filtration, and then purified by a silica gel column chromatography (DCM/EtOAc/MeOH (v/v/v)=80/40/1) to give the title compound as a white solid (46 mg, 50%).

MS (ESI, pos. ion) m/z: 487.0 [M+H]$^+$;

$^1$H NMR (300 MHz, DMSO-d$_6$): δ (ppm) 10.81 (s, 1H), 9.13 (s, 1H), 8.04 (d, J=5.9 Hz, 1H), 7.99-7.94 (m, 1H), 7.71-7.65 (m, 2H), 7.62-7.42 (m, 5H), 7.15-7.09 (m, 2H), 6.87 (d, J=2.3 Hz, 1H), 6.51 (dd, J=2.3 Hz, 5.9 Hz, 1H), 3.36 (s, 3H), 2.71 (s, 3H), 2.68 (d, J=4.6 Hz, 3H).

Biological Testing

The LC/MS/MS system used in the analysis consists of an Agilent 1200 Series vacuum degasser, binary pump, well-plate autosampler, thermostatted column compartment, the Agilent G6430 TripleQuadrupole Mass Spectrometer with an electrosprayionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 40 psi |
| Drying Gas Flow | 10 L/min |

An Agilent XDB-C18, 2.1×30 mm, 3.5 μM column was used for the analysis. 5 μL of the samples were injected. Analysis condition: The mobile phase was 0.1% formic acid in water (A) and 0.1% formic acidin methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 μM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 μL of the samples were injected.

Example A

Compound Stability in Human and Rat Liver Microsomes

Human or rat liver microsomes incubations were conducted in duplicate in polypropylene tubes. The typical incubation mixtures consisted of human or rat liver microsomes (0.5 mg protein/mL), compounds of interest (5 μM) and NADPH (1.0 mM) in a total volume of 200 μL, potassium phosphate buffer (PBS, 100 mM, pH 7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human or rat liver microsomes were determined by a LC/MS/MS method. The ranges of the linearity in the concentration range were determined for each tested compounds.

A parallel incubation was performed using denatured microsomes as the negative control, and reactions were terminated at various time points (0, 15, 60 min) after incubation at 37° C.

Dextromethorphan (70 μM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Data Analysis

The concentrations of compounds in human or rat liver microsome incubations were plotted as a percentage of the relevant zero time point control for each reaction. The in vivo $CL_{int}$ were extrapolated (ref.: Naritomi Y, Terashita S, Kimura S, Suzuki A, Kagayama A, Sugiyama Y. Prediction of human hepatic clearance from in vivo animal experiments and in vitro metabolic studies with liver microsomes from animals and humans. *Drug Metabolism and Disposition* 2001, 29: 1316-1324.)

TABLE 2

Rat liver microsomes stability

| | Rat | |
|---|---|---|
| Example # | $T_{1/2}$ (min) | $CL_{int}$ (mL/min/kg) |
| Ex. 8 | 702.8 | 3.53 |
| Ex. 11 | 235.7 | 10.54 |
| Ex. 16 | 423.9 | 5.86 |

The compounds disclosed herein are very stable in rat liver microsomes. For example, Examples 8, 11 and 16 were little metabolized when they were incubated in rat liver microsomes under the experimental condition, thus showed prolonged $T_{1/2}$.

Example B

Evaluation of Pharmacokinetics after Intravenous and Oral Administration of the Compounds Disclosed Herein in Mice, Rats, Dogs and Monkeys The compounds disclosed herein are assessed in pharmacokinetic studies in mice, rats, dogs or monkeys. The compounds are administered as a water solution, 2% HPMC+1% TWEEN®80 in water solution, 5% DMSO+5% solutol in saline, 4% MC suspension or capsule. For the intravenous administration, the animals are generally given at 1 or 2 mg/kg dose. For the oral (p.o.) dosing, mice and rats are generally given 5 or 10 mg/kg dose, and dogs and monkeys are generally given 10 mg/kg dose. The blood samples (0.3 mL) are drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected, stored at −20° C. or −70° C. until analyzed by LC/MS/MS as described above.

TABLE 3

Pharmacokinetic profiles in rats

| | iv dosing | | | | | |
|---|---|---|---|---|---|---|
| Example # | dose mg/kg | $T_{1/2}$ h | $AUC_{last}$ ng · h/ml | Cl/F L/h/kg | Vss L/kg | F % |
| Ex. 8 | 2 | 4.06 | 38253 | 0.05 | 0.27 | 85.88 |
| Ex. 11 | 1 | 4.61 | 13980 | 0.05 | 0.34 | 133.5 |
| Ex. 16 | 1 | 5.95 | 23403 | 0.04 | 0.31 | 94.49 |

The compounds disclosed herein exhibited optimized pharmacokinetic properties with desirable clearance (Cl), half-life ($T_{1/2}$) and excellent oral bioavailability when the compounds were administered intravenously or orally.

The efficacy of the compounds disclosed herein as inhibitors of receptor tyrosine kinases, such as c-Met, VEGFR, Ron, and Axl related activity and as anti-tumor agents in xenograft animal models can be evaluated as follows. The assay results can demonstrate that certain compounds disclosed herein potently inhibit c-Met, VEGF-R2, Ron, and Axl phosphorylation, and demonstrate potent, dose dependent anti-tumor activity in certain xenograft models.

Kinase Assays

Kinase assays can be performed by measurement of incorporation of $\gamma$-$^{33}$P ATP into immobilized myelin basic protein (MBP). High binding white 384 well plates (Greiner) are coated with MBP (Sigma #M-1891) by incubation of 60 μl/well of 20 μg/ml MBP in Tris-buffered saline (TBS; 50 mM Tris pH 8.0, 138 mM NaCl, 2.7 mM KCl) for 24 hours at 4° C. Plates are washed 3× with 100 μL TBS. Kinase reactions are carried out in a total volume of 34 μL in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and $\gamma$-$^{33}$P ATP is added to start the reaction (2×10$^6$ cpm of $\gamma$-$^{33}$P ATP per well (3000 Ci/mmole) and 10 μM unlabeled ATP, typically. The reactions are carried out for 1 hour at room temperature with shaking Plates are washed 7× with TBS, followed by the addition of 50 μL/well scintillation fluid (Wallac). Plates are read using a Wallac Trilux counter. This is only one format of such assays; various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the condition of the assay. The IC$_{50}$ value is estimated by preparing a 10 point curve using a ½ log dilution series (for example, a typical curve may be prepared using the following compound concentrations; 100 μM, 30 μM, 10 μM, 3 μM, 1 μM, 0.3 μM, 0.1 μM, 0.03 μM, 0.01 μM and 0 μM).

c-Met (h) Assay

Met (h) is incubated with 8 mM MOPS pH 7.0, 0.2 mM EDTA, 250 μM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

KDR (h) (VEGF-R2(h)) Assay:

KDR (h) is incubated with 8 mM MOPS pH 7.0, 0.2 mM EDTA, 0.33 mg/mL myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Axl (h) Assay

Axl (h) is incubated with 8 mM MOPS pH 7.0, 0.2 mM EDTA, 250 μM KKSRGDYMTMQIG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

The kinase assays described herein can be performed at Millipore UK Ltd, Dundee Technology Park, Dundee DD2 1SW, UK.

Alternatively, the kinase activities of the compounds can be measured using KINOMEscan™, which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag.

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEABLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% TWEEN®20). The beads were then re-suspended in elution buffer (1×PBS, 0.05% TWEEN®20, 0.5 μM non-biotinylated affinity ligand) and incubated at room temperature with shaking for 30 minutes. The kinase concentration in the eluates was measured by qPCR.

The kinase assays described herein were performed using KINOMEscan™ Profiling Service at DiscoveRx Corporation, 42501 Albrae St. Fremont, Calif. 94538, USA, and the selected results are listed in Table 4.

TABLE 4

Binding constants (Kds) of selected examples

| Example # | Kd (nM) | |
|---|---|---|
| | KDR (h) | c-Met (h) |
| Ex. 8 | 3.2 | 2.4 |
| Ex. 10 | 450 | 200 |
| Ex. 11 | 6.3 | 0.5 |
| Ex. 16 | 2.9 | 0.21 |

The compounds disclosed herein exhibited potent activities in the c-Met (h), and KDR (h) assays.

Cellular Phosphorylation Assays

Generally, cells are preincubated with test compounds to allow thorough target binding. The autophosphorylation level was determined Sandwich-ELISA technique. IC$_{50}$ values are determined by testing 8 compound concentrations in semi-logarithmic steps (each concentration in duplicates). The cellular phosphorylation assays described herein can be performed at ProQinase GmbH, Breisacher Straße 117 D-79106, Freiburg, Germany.

c-Met Phosphorylation Assay:

The human gastric adenocarcinoma cell line MKN45 is known to overexpress c-Met. c-Met overexpression results in a constitutive, ligand-independent autophosphorylation of the kinase. By adding SU11274 phospho-MET levels are largely decreased and thus the dynamic behavior to determine inhibitory potentials of compounds was achieved. Phospho-MET signal is subsequently quantified by Sandwich-ELISA technique. The assay is validated based on known inhibitors of MET kinase activity.

VEGF-R2 Phosphorylation Assay:

Immortalized human umbilical vein endothelial cells (HUE) are known to overexpress human VEGF-R2. Stimulation of these cells with its physiological ligand VEGF-A results in a robust receptor autophosphorylation. Compounds are preincubated before cell stimulation to allow thorough target binding. Stimulation conditions are optimized to determine dose-related inhibition of the phospho-VEGF-R2 signal, which is subsequently quantified by Sandwich-ELISA technique. The assay is validated based on known inhibitors of VEGF-R2 kinase activity.

Axl Phosphorylation Assay:

Cellular AXL phosphorylation assay was generated on a mouse embryonal fibroblast (MEF) background. Cells were transfected to express a full-length AXL protein. After clonal selection a transformed cell line with a high level of auto-phosphorylated AXL was obtained. By adding Staurosporine phospho-AXL levels are largely decreased and thus the dynamic behavior to determine inhibitory potentials of compounds was achieved. PhosphoAXL levels are quantified by Sandwich-ELISA technique.

Tumor Xenograft Models

The efficacy of compounds disclosed herein was evaluated in a standard murine model of tumorigenesis. Human tumor cells (U87MG glioblastoma cells from ATCC) were expended in culture, harvested, and injected subcutaneously onto the rear flank of 6-7 week old female athymic nude mice (BALB/cA nu/nu, Hunan SLAC Laboratory Animal, Co.) (n=6-10 for vehicle group and for each dosing group). When tumors reached a volume of 100-250 mm$^3$, animals were randomly divided into vehicle control (for example, 5% DMSO+70% Captisol® (30%), 7% HCl (pH1), 18% Captisol® (30%); or 7% DMSO, 7% HCl (pH1), 70% Captisol® (30%), 16% Captisol® (30%), or the like) and compound groups. Subsequent administration of compound by oral gavage begins anywhere from day 0 to day 15 post tumor cell challenge and generally continues with once a day for the duration of the experiment.

Tumor Growth Inhibition (TGI) Analysis

Progression of tumor growth is assessed by tumor volumes and recorded as a function of time. The long (L) and short (W) axes of the subcutaneous tumors were measured with calipers twice weekly, and the tumor volume (TV) calculated as (L×W$^2$)/2). TGI was calculated from the difference between the median tumor volumes of vehicle-treated and drug-treated mice, expressed as a percentage of the median tumor volume of the vehicle-treated control group, by the following relation:

$$\% \; TGI = \left( \frac{\text{Median Tumor } Volume_{control} - \text{Median Tumor } Volume_{drug\text{-}treated}}{\text{Median Tumor } Volume_{control}} \right) \times 100$$

Initial statistical analysis is done by repeated measures analysis of variance (RMANOVA), followed by Scheffe psot hoc testing for multiple comparisons. Vehicle alone (5% DMSO+ 70% Captisol® (30%), 7% HCl (pH1), 18% Captisol® (30%); or 7% DMSO, 7% HCl (pH1), 70% Captisol® (30%), 16% Captisol® (30%), or the like) is the negative control.

TABLE 5

Selected results from tumor xenograft model studies

| TGI % (on last day of dosing) | U87MG Xenograft models | |
| --- | --- | --- |
| | 6 mg/kg | 30 mg/kg |
| Ex. 8 (12 days) | 32 | 78 |
| Ex. 11 (12 days) | 56 | 97 |

Finally, it should be noted that there are alternative ways of implementing the present invention. Accordingly, the present embodiments are to be considered as illustrative and not restrictive and the invention is not be limited to the details given herein, but may be modified within the scope and equivalents of the appended claims. All publications and patents cited herein are incorporated by reference.

What is claimed is:

1. A method of inhibiting or modulating the activity of a protein kinase in a biological sample comprising contacting a biological sample with a compound of Formula (I):

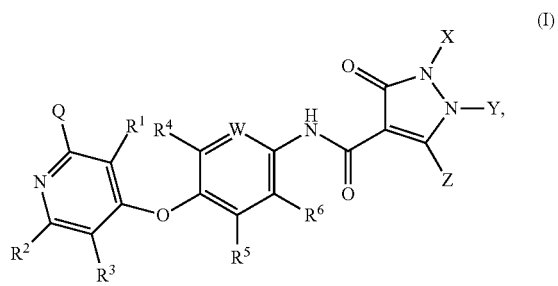

or a stereoisomer, a geometric isomer, a tautomer, an N-oxide, a hydrate, a solvate, a metabolite, or a pharmaceutically acceptable salt thereof, wherein:

Q is D, —N(R$^c$)C(=O)NR$^a$R$^b$, —N(R$^c$)C(=O)R$^d$, —C(=O)NR$^a$R$^b$, —N(R$^c$)S(=O)NR$^a$R$^b$, —N(R$^c$)S(=O)R$^a$, —N(R$^c$)S(=O)$_2$NR$^a$R$^b$ or —N(R$^c$)S(=O)$_2$R$^a$;

W is CR$^7$ or N;

each of X, Y and Z is independently H, D, (C$_1$-C$_6$)alkyl, (C$_3$-C$_8$)cycloalkyl, —(C$_1$-C$_4$)alkylene-(C$_3$-C$_8$)cycloalkyl, (C$_3$-C$_7$)heterocyclyl, —(C$_1$-C$_4$)alkylene-(C$_3$-C$_7$)heterocyclyl, (C$_6$-C$_{10}$)aryl, 5-10 membered heteroaryl comprising 1, 2, 3 or 4 heteroatoms independently selected from O, S and N, —(C$_1$-C$_4$)alkylene-(C$_6$-C$_{10}$)aryl or —(C$_1$-C$_4$)alkylene-(5-10 membered heteroaryl), wherein each of the (C$_1$-C$_6$)alkyl, (C$_3$-C$_8$)cycloalkyl, —(C$_1$-C$_4$)alkylene-(C$_3$-C$_8$)cycloalkyl, (C$_3$-C$_7$)heterocyclyl, —(C$_1$-C$_4$)alkylene-(C$_3$-C$_7$)heterocyclyl, (C$_6$-C$_{10}$)aryl, 5-10 membered heteroaryl, —(C$_1$-C$_4$)alkylene-(C$_6$-C$_{10}$)aryl and —(C$_1$-C$_4$)alkylene-(5-10 membered heteroaryl) is unsubstituted or optionally substituted with 1, 2, 3, 4 or 5 substituents independently selected from D, F, Cl, Br, CN, (C$_2$-C$_6$)alkenyl, (C$_2$-C$_6$)alkynyl, OR$^a$, NR$^a$R$^b$, —(C$_1$-C$_4$)alkylene-OR$^a$ and —(C$_1$-C$_4$)alkylene-NR$^a$R$^b$;

each of R$^1$, R$^2$, R$^3$, R$^4$, R$^5$, R$^6$ and R$^7$ is independently H, D, F, Cl, Br, CN, N$_3$, OR$^a$, (C$_1$-C$_6$)alkyl, (C$_1$-C$_6$)haloalkyl, (C$_2$-C$_6$)alkenyl or (C$_2$-C$_6$)alkynyl;

each of R$^a$, R$^b$ and R$^c$ is independently H, (C$_1$-C$_6$)aliphatic, (C$_1$-C$_6$)haloalkyl, (C$_3$-C$_6$)cycloalkyl, —(C$_1$-C$_4$)alkylene-(C$_3$-C$_6$)cycloalkyl, (C$_3$-C$_6$)heterocyclyl, —(C$_1$-C$_4$)alkylene-(C$_3$-C$_6$)heterocyclyl, (C$_6$-C$_{10}$)aryl, 5-10 membered heteroaryl comprising 1, 2, 3 or 4 heteroatoms independently selected from O, S and N, —(C$_1$-C$_4$)alkylene-(C$_6$-C$_{10}$)aryl or —(C$_1$-C$_4$)alkylene-(5-10 membered heteroaryl), wherein each of the (C$_1$-C$_6$)aliphatic, (C$_1$-C$_6$)haloalkyl, (C$_3$-C$_6$)cycloalkyl, —(C$_1$-C$_4$)alkylene-(C$_3$-C$_6$)cycloalkyl, (C$_3$-C$_6$)heterocyclyl, —(C$_1$-C$_4$)alkylene-(C$_3$-C$_6$)heterocyclyl, (C$_6$-C$_{10}$)aryl, 5-10 membered heteroaryl, —(C$_1$-C$_4$)alkylene-(C$_6$-C$_{10}$)aryl and —(C$_1$-C$_4$)alkylene-(5-10 membered heteroaryl) is unsubstituted or optionally substituted with 1, 2, 3 or 4 substituents independently selected from D, F, Cl, CN, N$_3$, OH, NH$_2$, (C$_1$-C$_6$)haloalkyl, (C$_1$-C$_6$)alkoxy and (C$_1$-C$_6$)alkylamino; and R$^d$ is D, (C$_3$-C$_8$)cycloalkyl, —(C$_1$-C$_4$)alkylene-(C$_6$-C$_{10}$)aryl, 5-10 membered heteroaryl comprising 1, 2, 3 or 4 heteroatoms independently selected from O, S and N or —(C$_1$-C$_4$)alkylene-(5-10 membered heteroaryl), wherein each of the (C$_3$-C$_8$)cycloalkyl, —(C$_1$-C$_4$)alkylene-(C$_6$-C$_{10}$)aryl, 5-10 membered heteroaryl and —(C$_1$-C$_4$)alkylene-(5-10 membered heteroaryl) is unsubstituted or optionally substituted with 1, 2, 3 or 4 substitutents independently selected from D, F, Cl, Br, CN, $OR^a$, $NR^aR^b$, $(C_1-C_6)$alkyl, $(C_2-C_6)$alkenyl, $(C_2-C_6)$alkynyl, —$(C_1-C_4)$alkylene-$OR^a$ and —$(C_1-C_4)$alkylene-$NR^aR^b$.

2. The method of claim 1, wherein the protein kinase is a receptor tyrosine kinase.

3. The method of claim 2, wherein the receptor tyrosine kinase is VEGFR, c-Met, Ron, Axl or a combination thereof.

4. A method of inhibiting or modulating the activity of a protein kinase in a biological sample comprising contacting a biological sample with a pharmaceutical composition comprising a compound of Formula (I):

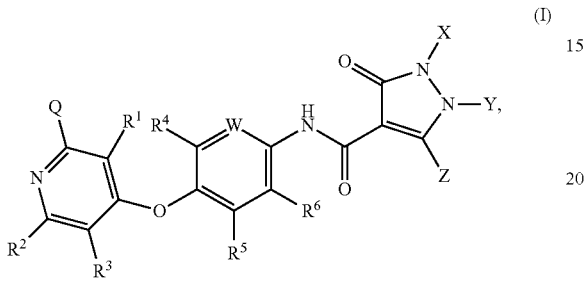

(I)

or a stereoisomer, a geometric isomer, a tautomer, an N-oxide, a hydrate, a solvate, a metabolite, or a pharmaceutically acceptable salt thereof, wherein:

Q is D, —$N(R^c)C(=O)NR^aR^b$, —$N(R^c)C(=O)R^d$, —$C(=O)NR^aR^b$, —$N(R^c)S(=O)NR^aR^b$, —$N(R^c)S(=O)R^a$, —$N(R^c)S(=O)_2NR^aR^b$ or —$N(R^c)S(=O)_2R^a$;

W is $CR^7$ or N;

each of X, Y and Z is independently H, D, $(C_1-C_6)$alkyl, $(C_3-C_8)$cycloalkyl, —$(C_1-C_4)$alkylene-$(C_3-C_8)$cycloalkyl, $(C_3-C_7)$heterocyclyl, —$(C_1-C_4)$alkylene-$(C_3-C_7)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$alkyl, $(C_3-C_8)$cycloalkyl, —$(C_1-C_4)$alkylene-$(C_3-C_8)$cycloalkyl, $(C_3-C_7)$heterocyclyl, —$(C_1-C_4)$alkylene-$(C_3-C_7)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3, 4 or 5 substituents independently selected from D, F, Cl, Br, CN, $(C_2-C_6)$alkenyl, $(C_2-C_6)$alkynyl, $OR^a$, $NR^aR^b$, —$(C_1-C_4)$alkylene-$OR^a$ and —$(C_1-C_4)$alkylene-$NR^aR^b$;

each of $R^1$, $R^2$, $R^3$, $R^4$, $R^5$, $R^6$ and $R^7$ is independently H, D, F, Cl, Br, CN, $N_3$, $OR^a$, $(C_1-C_6)$alkyl, $(C_1-C_6)$haloalkyl, $(C_2-C_6)$alkenyl or $(C_2-C_6)$alkynyl;

each of $R^a$, $R^b$ and $R^c$ is independently H, $(C_1-C_6)$aliphatic, $(C_1-C_6)$haloalkyl, $(C_3-C_6)$cycloalkyl, —$(C_1-C_4)$alkylene-$(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl or —$(C_1-C_4)$alkylene-(5-10 membered heteroaryl), wherein each of the $(C_1-C_6)$aliphatic, $(C_1-C_6)$haloalkyl, $(C_3-C_6)$cycloalkyl, —$(C_1-C_4)$alkylene-$(C_3-C_6)$cycloalkyl, $(C_3-C_6)$heterocyclyl, —$(C_1-C_4)$alkylene-$(C_3-C_6)$heterocyclyl, $(C_6-C_{10})$aryl, 5-10 membered heteroaryl, —$(C_1-C_4)$alkylene-$(C_6-C_{10})$aryl and —$(C_1-C_4)$alkylene-(5-10 membered heteroaryl) is unsubstituted or optionally substituted with 1, 2, 3 or 4 substitutents independently selected from D, F, Cl, CN, $N_3$, OH, $NH_2$, $(C_1-C_6)$haloalkyl, $(C_1-C_6)$alkoxy and $(C_1-C_6)$alkylamino; and $R^d$ is D, $(C_3-C_8)$cycloalkyl, —$(C_1-C_4)$alkylene-$(C_6-C_{10})$aryl, 5-10 membered heteroaryl comprising 1, 2, 3 or 4 heteroatoms independently selected from O, S and N or —$(C_1-C_4)$alkylene-(5-10 membered heteroaryl), wherein each of the $(C_3-C_8)$cycloalkyl, —$(C_1-C_4)$alkylene-$(C_6-C_{10})$aryl, 5-10 membered heteroaryl and —$(C_1-C_4)$alkylene-(5-10 membered heteroaryl) is unsubstituted or optionally substituted with 1, 2, 3 or 4 substitutents independently selected from D, F, Cl, Br, CN, $OR^a$, $NR^aR^b$, $(C_1-C_6)$alkyl, $(C_2-C_6)$alkenyl, $(C_2-C_6)$alkynyl, —$(C_1-C_4)$alkylene-$OR^a$ and —$(C_1-C_4)$alkylene-$NR^aR^b$;

and a pharmaceutically acceptable carrier, excipient, diluent, adjuvant, vehicle or a combination thereof.

5. The method of claim 4, wherein the protein kinase is receptor tyrosine kinase.

6. The method of claim 5, wherein the receptor tyrosine kinase is VEGFR, c-Met, Ron, Axl or a combination thereof.

\* \* \* \* \*